(12) United States Patent
Schaefer et al.

(10) Patent No.: US 8,628,862 B2
(45) Date of Patent: Jan. 14, 2014

(54) ELECTROLUMINESCENT DEVICE

(75) Inventors: Thomas Schaefer, Liestal (CH); Colin Morton, Derby (GB); Peter Murer, Oberwil (CH); Frederique Wendeborn, Ranspach-le-Haut (FR); Beat Schmidhalter, Bubendorf (CH); Kristina Bardon, Waldshut (DE)

(73) Assignee: BASF SE, Ludwigshafen (DE)

( * ) Notice: Subject to any disclaimer, the term of this patent is extended or adjusted under 35 U.S.C. 154(b) by 714 days.

(21) Appl. No.: 12/678,382

(22) PCT Filed: Sep. 10, 2008

(86) PCT No.: PCT/EP2008/061952
§ 371 (c)(1),
(2), (4) Date: Jun. 22, 2010

(87) PCT Pub. No.: WO2009/037155
PCT Pub. Date: Mar. 26, 2009

(65) Prior Publication Data
US 2010/0277060 A1   Nov. 4, 2010

(30) Foreign Application Priority Data

Sep. 20, 2007 (EP) .................................... 07116824

(51) Int. Cl.
*H01L 51/54* (2006.01)
*C09K 11/06* (2006.01)

(52) U.S. Cl.
USPC ........... 428/690; 428/917; 313/504; 313/506; 252/301.16; 257/40; 257/103; 585/25; 585/26

(58) Field of Classification Search
None
See application file for complete search history.

(56) References Cited

U.S. PATENT DOCUMENTS

| | | | |
|---|---|---|---|
| 3,180,730 A | 4/1965 | Klupfel et al. |
| 3,567,450 A | 3/1971 | Brantly et al. |
| 3,658,520 A | 4/1972 | Brantly et al. |
| 4,356,429 A | 10/1982 | Tang |
| 4,539,507 A | 9/1985 | VanSlyke et al. |
| 4,720,432 A | 1/1988 | VanSlyke et al. |
| 4,768,292 A | 9/1988 | Manzei |
| 4,769,292 A | 9/1988 | Tang et al. |
| 4,885,211 A | 12/1989 | Tang et al. |
| 4,885,221 A | 12/1989 | Tsuneeda |
| 5,059,861 A | 10/1991 | Littman et al. |
| 5,059,862 A | 10/1991 | VanSlyke et al. |
| 5,061,569 A | 10/1991 | VanSlyke et al. |
| 5,141,671 A | 8/1992 | Bryan et al. |
| 5,150,006 A | 9/1992 | Van Slyke et al. |
| 5,151,629 A | 9/1992 | VanSlyke |
| 5,247,190 A | 9/1993 | Friend et al. |
| 5,276,380 A | 1/1994 | Tang |
| 5,294,870 A | 3/1994 | Tang et al. |
| 5,405,709 A | 4/1995 | Littman et al. |
| 5,484,922 A | 1/1996 | Moore et al. |
| 5,554,450 A | 9/1996 | Shi et al. |
| 5,593,788 A | 1/1997 | Shi et al. |
| 5,608,287 A | 3/1997 | Hung et al. |
| 5,645,948 A | 7/1997 | Shi et al. |
| 5,677,572 A | 10/1997 | Hung et al. |
| 5,683,823 A | 11/1997 | Shi et al. |
| 5,688,551 A | 11/1997 | Littman et al. |
| 5,703,436 A | 12/1997 | Forrest et al. |
| 5,714,838 A | 2/1998 | Haight et al. |
| 5,739,545 A | 4/1998 | Guha et al. |
| 5,755,999 A | 5/1998 | Shi et al. |
| 5,776,622 A | 7/1998 | Hung et al. |
| 5,776,623 A | 7/1998 | Hung et al. |
| 5,837,391 A | 11/1998 | Utsugi |
| 5,851,709 A | 12/1998 | Grande et al. |
| 5,928,802 A | 7/1999 | Shi et al. |
| 5,935,720 A | 8/1999 | Chen et al. |
| 5,935,721 A | 8/1999 | Shi et al. |
| 5,969,474 A | 10/1999 | Arai |
| 5,981,306 A | 11/1999 | Burrows et al. |
| 6,020,078 A | 2/2000 | Chen et al. |
| 6,066,357 A | 5/2000 | Tang et al. |
| 6,097,147 A | 8/2000 | Baldo et al. |
| 6,137,223 A | 10/2000 | Hung et al. |
| 6,140,763 A | 10/2000 | Hung et al. |
| 6,172,459 B1 | 1/2001 | Hung et al. |
| 6,208,075 B1 | 3/2001 | Hung et al. |

(Continued)

FOREIGN PATENT DOCUMENTS

| | | |
|---|---|---|
| DE | 100 58 578 | 6/2002 |
| EP | 0 731 625 | 9/1996 |

(Continued)

OTHER PUBLICATIONS

English language machine translation of KR 10-2007-0079680 A, 2007.*
English language translation of KR 10-2007-0102243 A, 2007.*
U.S. Appl. No. 13/315,687, filed Dec. 9, 2011, Schaefer, et al.

*Primary Examiner* — Michael H Wilson
(74) *Attorney, Agent, or Firm* — Oblon, Spivak, McClelland, Maier & Neustadt, L.L.P.

(57) ABSTRACT

The present invention relates to an electronic device, especially an electroluminescent devices, comprising a compound of Formula (I), especially as host for phosphorescent compounds. The hosts may function with phosphorescent materials to provide improved efficiency, stability, manufacturability, or spectral characteristics of electroluminescent devices.

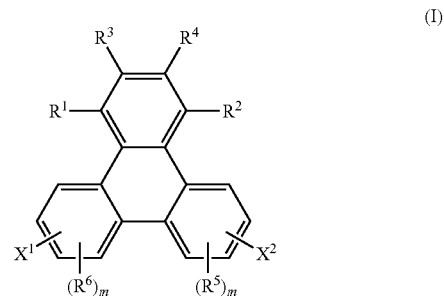

(I)

6 Claims, No Drawings

(56) References Cited

U.S. PATENT DOCUMENTS

| | | |
|---|---|---|
| 6,226,890 B1 | 5/2001 | Boroson et al. |
| 6,278,236 B1 | 8/2001 | Madathil et al. |
| 6,284,393 B1 | 9/2001 | Hosokawa et al. |
| 6,337,102 B1 | 1/2002 | Forrest et al. |
| 6,413,656 B1 | 7/2002 | Thompson et al. |
| 6,451,415 B1 | 9/2002 | Forrest et al. |
| 6,451,455 B1 | 9/2002 | Thompson et al. |
| 6,458,475 B1 | 10/2002 | Adachi et al. |
| 6,492,041 B2 | 12/2002 | Ishiskawa et al. |
| 6,515,298 B2 | 2/2003 | Forrest et al. |
| 6,573,651 B2 | 6/2003 | Adachi et al. |
| 7,090,930 B2 | 8/2006 | Robello et al. |
| 2002/0064679 A1 | 5/2002 | Ishiskawa et al. |
| 2002/0100906 A1 | 8/2002 | Takiguchi et al. |
| 2002/0117662 A1 | 8/2002 | Nii |
| 2002/0121638 A1 | 9/2002 | Grushin et al. |
| 2002/0197511 A1 | 12/2002 | D'Andrade et al. |
| 2003/0017361 A1 | 1/2003 | Thompson et al. |
| 2003/0040627 A1 | 2/2003 | Fujii |
| 2003/0054198 A1 | 3/2003 | Tsuboyama et al. |
| 2003/0059646 A1 | 3/2003 | Kamatani et al. |
| 2003/0068526 A1 | 4/2003 | Kamatani et al. |
| 2003/0068528 A1 | 4/2003 | Thompson et al. |
| 2003/0068535 A1 | 4/2003 | Takiguchi et al. |
| 2003/0072964 A1 | 4/2003 | Kwong et al. |
| 2003/0124381 A1 | 7/2003 | Thompson et al. |
| 2003/0141809 A1 | 7/2003 | Furugori et al. |
| 2003/0175553 A1 | 9/2003 | Thompson et al. |
| 2005/0025993 A1 | 2/2005 | Thompson et al. |
| 2005/0048318 A1 | 3/2005 | Suzuki et al. |
| 2005/0175857 A1 | 8/2005 | Coggan et al. |
| 2006/0088728 A1 | 4/2006 | Kwong et al. |
| 2006/0280965 A1* | 12/2006 | Kwong et al. ............... 428/690 |
| 2007/0087223 A1 | 4/2007 | Sakamoto et al. |
| 2007/0191583 A1 | 8/2007 | Jacob et al. |
| 2009/0105447 A1 | 4/2009 | Schafer et al. |
| 2009/0203866 A1 | 8/2009 | Schafer et al. |
| 2010/0039024 A1 | 2/2010 | Wendeborn et al. |

FOREIGN PATENT DOCUMENTS

| | | | |
|---|---|---|---|
| EP | 0 732 868 | 9/1996 | |
| EP | 0 891 121 | 1/1999 | |
| EP | 1 009 041 | 6/2000 | |
| EP | 1 029 909 | 8/2000 | |
| EP | 1 076 368 | 2/2001 | |
| EP | 1 238 981 | 9/2002 | |
| EP | 1 239 526 | 9/2002 | |
| EP | 1 244 155 | 9/2002 | |
| JP | 3 234963 | 10/1991 | |
| JP | 11 92420 | 4/1999 | |
| JP | 11 251063 | 9/1999 | |
| JP | 2003 59667 | 2/2003 | |
| JP | 2003 73387 | 3/2003 | |
| JP | 2003 73388 | 3/2003 | |
| JP | 2003 73665 | 3/2003 | |
| JP | 2005 259472 | 9/2005 | |
| JP | 2006 104124 | 4/2006 | |
| JP | 2006 143845 | 6/2006 | |
| JP | 2007 223921 | 9/2007 | |
| KR | 2006 0107720 | 10/2006 | |
| KR | 10-2007-0079680 A * | 8/2007 | ............. C09K 11/06 |
| KR | 2007 0102243 | 10/2007 | |
| WO | 00 57676 | 9/2000 | |
| WO | 00 70655 | 11/2000 | |
| WO | 01 39234 | 5/2001 | |
| WO | 01 41512 | 6/2001 | |
| WO | 01 93642 | 12/2001 | |
| WO | 02 15645 | 2/2002 | |
| WO | 02 071813 | 9/2002 | |
| WO | 02 074015 | 9/2002 | |
| WO | 2006 000544 | 1/2006 | |
| WO | 2006 038709 | 4/2006 | |
| WO | 2006 047119 | 5/2006 | |
| WO | 2006 130598 | 12/2006 | |
| WO | 2007 123254 | 11/2007 | |
| WO | 2008 012250 | 1/2008 | |
| WO | 2008 101842 | 8/2008 | |
| WO | 2008 119666 | 10/2008 | |

* cited by examiner

ELECTROLUMINESCENT DEVICE

This application is a 371 of PCT/EP08/61952 filed Sep. 10, 2008.

The present invention relates to an electronic device, especially an electroluminescent devices, comprising a compound of the formula

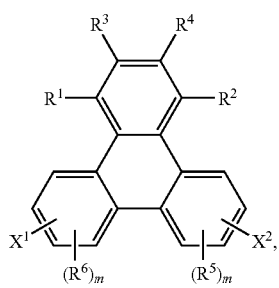

(I)

especially as host for phosphorescent compounds. The hosts may function with phosphorescent materials to provide improved efficiency, stability, manufacturability, or spectral characteristics of electroluminescent devices.

JP2007223921 relates to compounds of formula

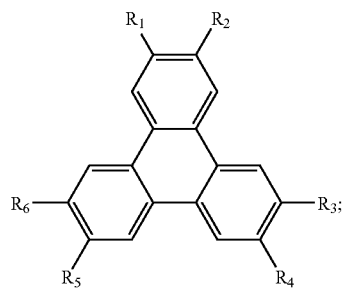

Q=

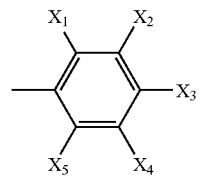

($R_1$-$R_6$=H, Q≥1 of $R_1$-$R_6$=Q; $X_1$-$X_5$=H, $C_{1-10}$alkyl, aryl, SiRaRbRc≥1 of $X_1$-$X_5$=SiRaRbRc; Ra, Rb, Rc=H, OH, $C_{1-10}$alkyl, alkoxy, aryl), which are useful as electron-transporting layer, host materials, etc., for org. electroluminescent devices.

KR2007102243 is directed to triphenylene derivs. of formula

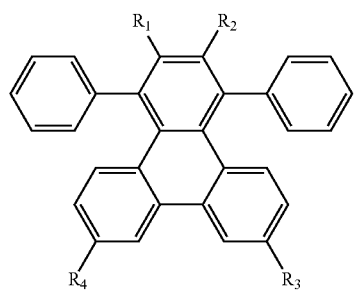

($R_1$-$R_4$ are H, $C_1$-$C_{10}$alkyl or alkoxyl, halogen, cyano group, nitro group, etc.). The triphenylene derivs. have high glass transition temp., and can be used as luminous materials of org. light-emitting diode.

KR2006107720 relates to a triphenylene derivative which has a high glass transition temperature and is excellent in thermal stability, and an organic light emitting diode containing the triphenylene derivative as a hole injection material, a hole transfer material or a light emitting layer material. The triphenylene derivative is represented by the formula

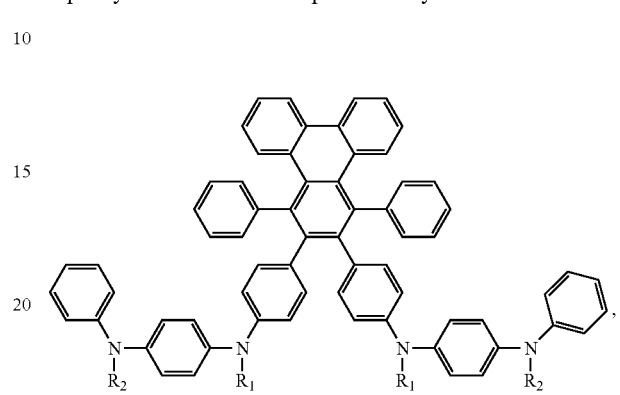

wherein $R_1$ and $R_2$ are a substituted or unsubstituted $C_6$-$C_{14}$aryl group.

JP11092420 relates to triphenylene derivatives of the formula

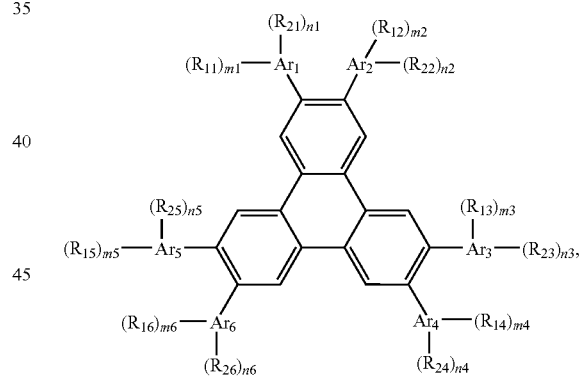

wherein $Ar_1$ to $Ar_6$ are each an aryl or the like; $R_{11}$ to $R_{16}$ are each formula

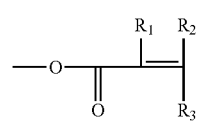

($R_1$ to $R_3$ are each, for example, H); $R_{21}$ to $R_{26}$ are each, for example, an alkyl; m1-m6 are each 0 or 1; n1-n6 are each 0, 1, or 2, which are useful as a liquid crystalline material. The following compounds are explicitly disclosed:

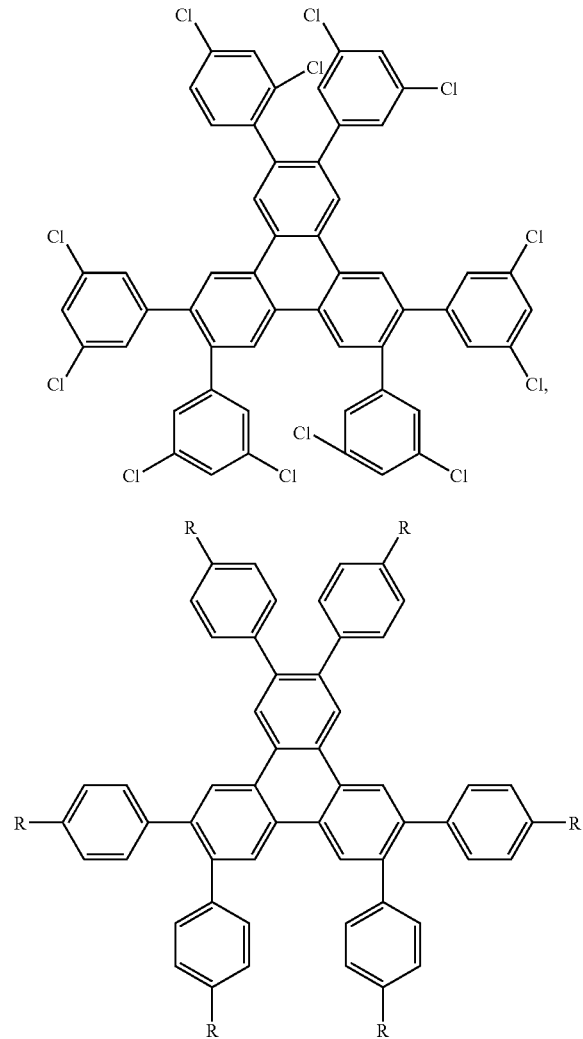

R=Cl, Br, or F.

JP11251063 discloses triphenylene compounds expressed by the formula

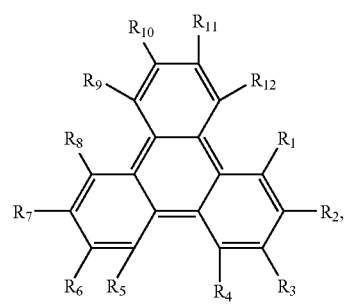

such as, for example,

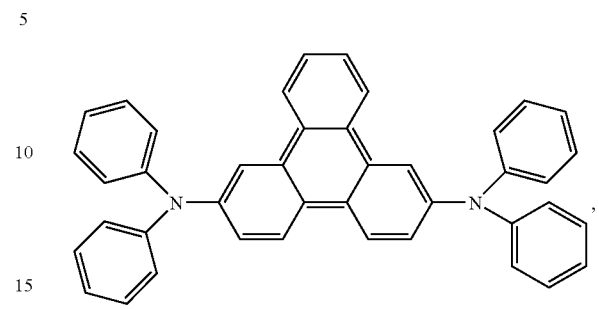

which are used as a component material of an organic EL element. In the formula, $R_1$ to $R_{12}$ each independently represent an hydrogen atom, a halogen atom, a hydroxyl group, a substituted or unsubstituted amino group, a nitro group, a cyano group, a substituted or unsubstituted alkyl group, a substituted or unsubstituted alkenyl group, a substituted or unsubstituted cycloalkyl group, a substituted or unsubstituted alkoxy group, a substituted or unsubstituted aromatic hydrocarbon group, a substituted or unsubstituted aromatic heterocycle group, a substituted or unsubstituted aralkyl group, a substituted or unsubstituted aryloxy group, a substituted or unsubstituted alkoxycarbonyl group, or a carboxyl group. $R_1$ to $R_{12}$ may form two rings out of them.

JP2005259472 relates to an organic electroluminescent element which has an organic layer including a mutually adjoining luminous layer and a block layer between a pair of electrodes and contains a phosphorescent material in the luminous layer, and contains triphenylene compound in the block layer.

Explicitly disclosed examples of the triphenylene compound, such as

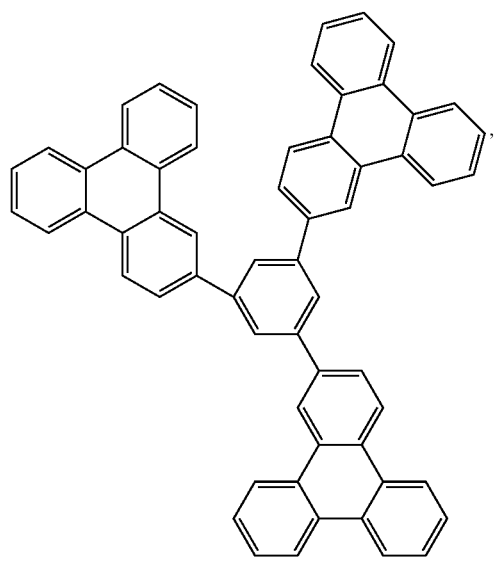

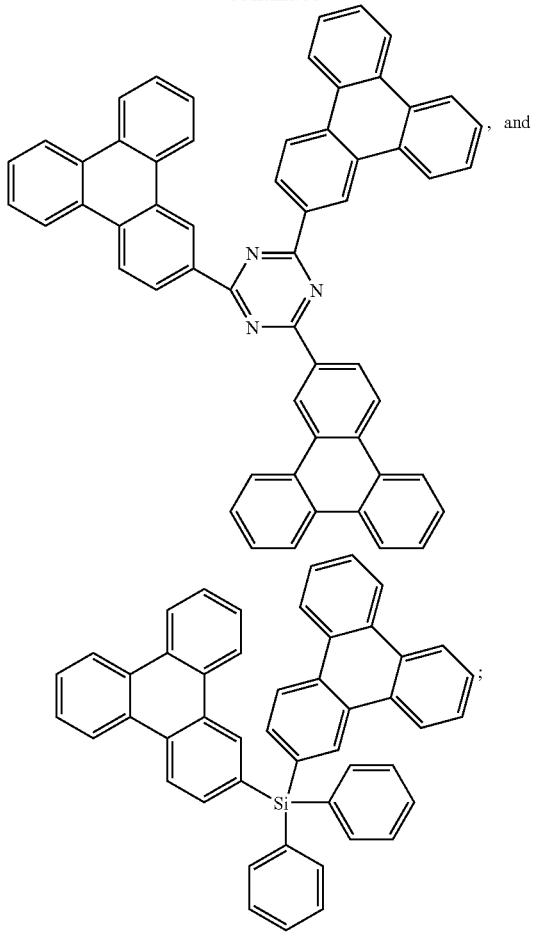

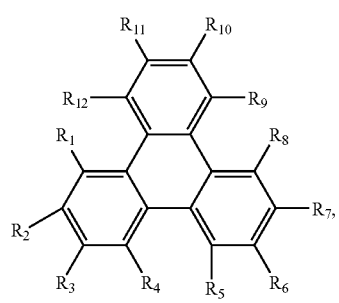

include at least two triphenyl groups, which are unsubstituted.

U.S. Pat. No. 6,492,041 relates to an organic electroluminescent (EL) device comprising an anode, a cathode and at least one organic thin-film layer disposed between said anode and said cathode, said one or more than one organic thin-film layers include a luminescent layer, said one or at least one of said more than one organic thin-film layers include a compound expressed by general formula [1]:

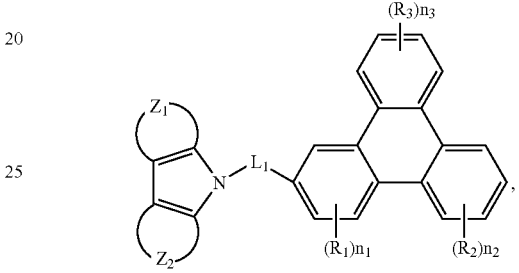

wherein each of $R_1$ to $R_{12}$ independently represents hydrogen atom, halogen atom, hydroxyl group, substituted or non-substituted amino group, nitro group, cyano group, substituted or non-substituted alkyl group, substituted or non-substituted alkenyl group, substituted or non-substituted cycloalkyl group, substituted or non-substituted alkoxy group, substituted or non-substituted aromatic hydrocarbon, substituted or non-substituted aromatic heterocyclic group, substituted or non-substituted aralkyl group, substituted or non-substituted aryloxy group, substituted or non-substituted alkoxycarbonyl group, or carboxyl group, and wherein each of $R_1$ to $R_{12}$ may be a ring formed by two of said atoms and groups and at least one of $R_1$ to $R_{12}$ is a diarylamino group expressed by —$NAr_1Ar_2$, each of $Ar_1$ and $Ar_2$ independently representing an aryl group having 6-20 carbons, one of $Ar_1$ and $Ar_2$ having a substituted or non-substituted styryl group as a substituent group and the other of the $Ar_1$ and $Ar_2$ having no substituted or non-substituted styryl group as a substituent group. The compounds of general formula [1] are used as hole transport material.

JP2006143845 relates to compounds of formula

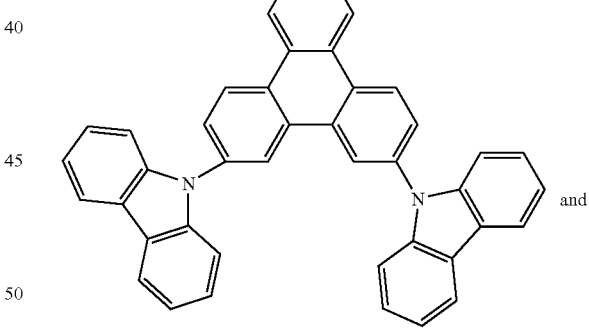

wherein $Z_1$, $Z_2$ are an aromatic hydrocarbon ring, aromatic heterocyclic ring; $R_1$ to $R_3$ are H, or substituent; n1=0 to 3; n2, n3=0 to 4; L1=linkage group, single bond), such as, for example,

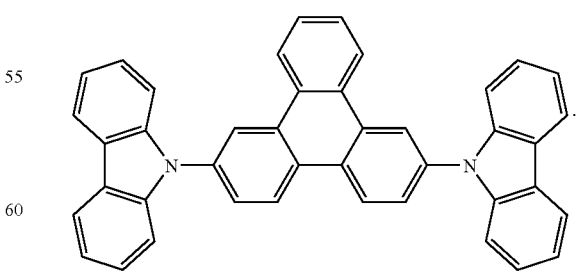

The compounds show high luminescence efficiency and long life.

WO2006038709 compounds represented by the general formula

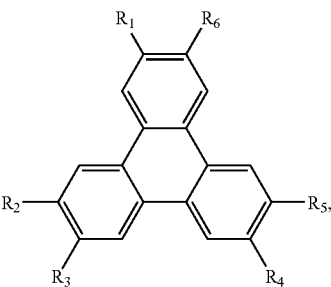

wherein $R_1$ to $R_6$ are each independently hydrogen or substituent represented by the general formula —C≡CSiRaRbRc, with the proviso that at least one of $R_1$ to $R_6$ is a substituent represented by the general formula —C≡SiRaRbRc, wherein Ra, Rb, Rc are each independently an $C_1$-$C_{10}$ aliphatic hydrocarbon group or aromatic hydrocarbon group. The compounds are prepared by coupling of halogenated triphenylene compds.

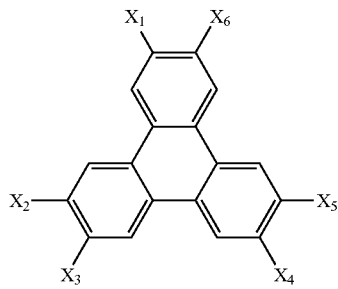

($X_1$ to $X_6$ are each independently H, Br, or iodo, with the proviso that at least one of X1-X6 is Br or iodo) with a silylacetylene of general formula HC≡C SiRaRbRc (Ra, Rb, Rc=same as above). An organic electroluminescent device comprising a luminescent layer containing at least one of compounds of formula

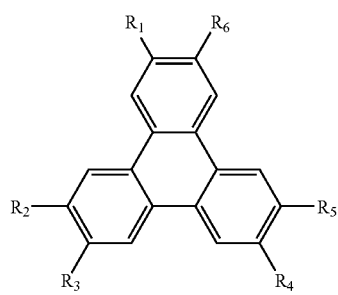

and a phosphorescent dopant is also disclosed. A compound of formula

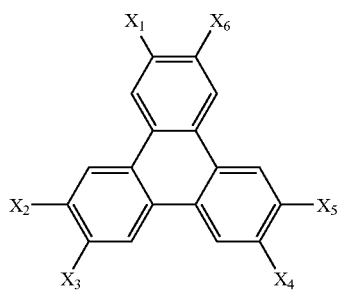

is explicitly disclosed, wherein $X_1$ to $X_6$ are each Br.

US2005025993 relates to electroluminescent devices which comprise an anode; a cathode; a first organic layer disposed between the anode and the cathode, where the first organic layer comprises a material that produces phosphorescent emission when a voltage is applied between the anode and the cathode; and a second organic layer disposed between the first organic layer and the cathode, where the second organic layer is in direct contact with the first organic layer, and where the second organic layer comprises a non-heterocyclic aromatic hydrocarbon material, such as, for example,

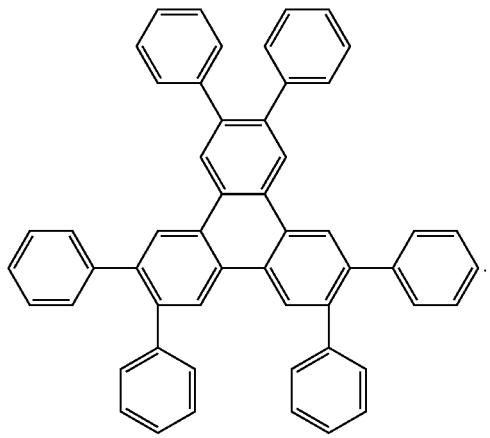 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1]

JP2006104124 relates to compounds represented by the general formula (I)

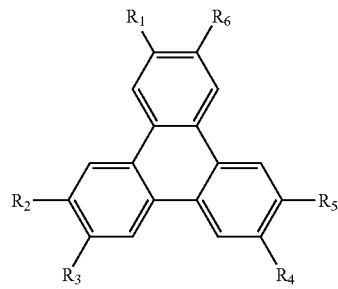

wherein $R_1$-$R_6$ are each independently hydrogen or substituent represented by the general formula —C≡CSiRaRbRc, with the proviso that at least one of $R_1$-$R_6$ is a substituent represented by the general formula —C≡CSiRaRbRc, wherein Ra, Rb, Rc are each independently $C_{1-10}$ aliphatic hydrocarbon group or aromatic hydrocarbon group. An organic electroluminescent device possessing a luminescent layer containing at least one of compounds I and a phosphorescent dopant is also disclosed.

WO2006047119 (US2006/0088728) relates to a device, comprising: an anode; a cathode; an emissive layer disposed between the anode and the cathode, wherein the emissive layer comprises a host and a dopant, and wherein the host material is selected from the group consisting of:

Compound III

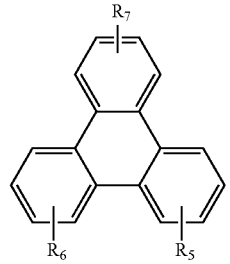

wherein each R represent no substitution, mono-, di-, or trisubstitution, and wherein the substituents are the same or different, and each is selected from the group consisting of alkyl, alkenyl, alkynyl, aryl, thioalkoxy, halo, haloalkyl, cyano, carbonyl, carboxyl, heteroaryl and substituted aryl, and wherein at least one R for each Compounds I, II, III, or IV includes a carbazole group.

The following compounds are explicitly disclosed in WO2006047119:

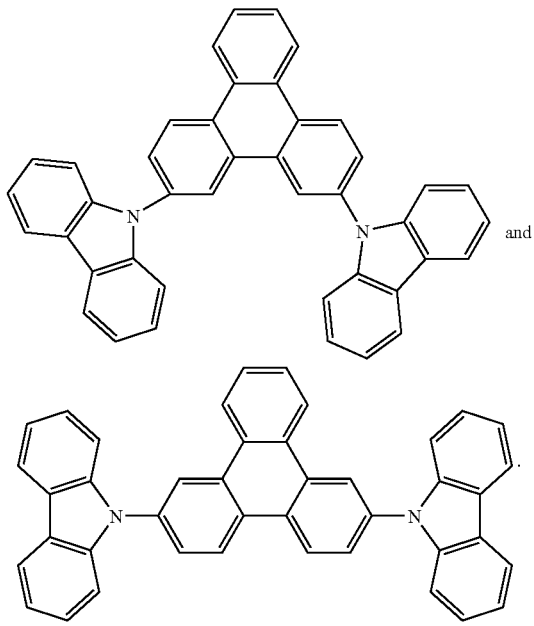

and

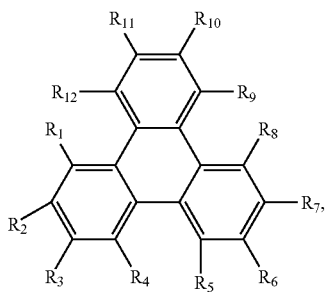

WO2006130598 relates to an emissive layer comprising a phosphorescent material and a triphenylene compound having the formula

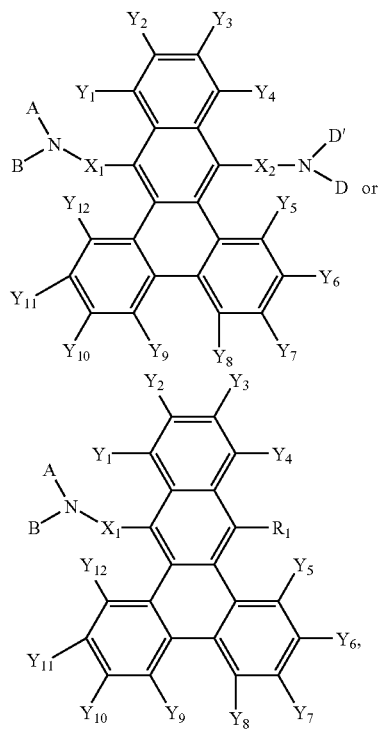

wherein $R_1$, $R_2$, $R_3$, $R_4$, $R_5$, $R_6$, $R_7$, $R_8$, $R_9$, $R_{10}$, $R_{11}$ and $R_{12}$ is each independently H or a substituent selected from the group consisting of aryl, substituted aryl, heteroaryl, substituted heteroaryl, alkyl, arylkyl, heteroalkyl, alkenyl, and alkynyl; and wherein the triphenylene compound has at least two substituents and a molecular weight of less than 1400. In the compounds, which are preferred and which are explicitly disclosed by means of examples, at least one of $R^9$ and $R^{12}$ is hydrogen.

US2007087223 relates to dibenzoanthracene derivatives substituted by an amino compound group at least one of 9-position and 14-position of a dibenzo[a,c]anthracene skeleton and represented by the following formula (1) or (2):

wherein:

$X^1$, $X^2$ and X each independently represents a substituted or unsubstituted arylene group or a substituted or unsubstituted divalent heterocyclic group;

A, B, D and D' each independently represents a substituted or unsubstituted alkyl group, a substituted or unsubstituted aryl group or a substituted or unsubstituted heterocyclic group, and between the adjacent groups, may be fused together to form rings; and $Y^1$ to $Y^{12}$ and $R^1$ each independently represents a hydrogen atom, a halogen atom, a substituted or unsubstituted alkyl group, an alkoxy group, a substituted or unsubstituted aryl group, or a substituted or unsubstituted heterocyclic group, and, when $Y^1$ to $Y^{12}$ and $R^1$ are other than a hydrogen atom or a halogen atom, $Y^1$ to $Y^{12}$ and $R^1$ may be fused together between the adjacent groups to form rings. The dibenzoanthracene derivatives are used as light-emitting material.

Notwithstanding these developments, there remains a need for EL devices comprising new host materials, and especially hosts that will function with phosphorescent materials to provide improved efficiency, stability, manufacturability, and/or spectral characteristics of electroluminescent devices.

Accordingly, the present invention provides an electronic device, especially an EL device, comprising a compound of the formula

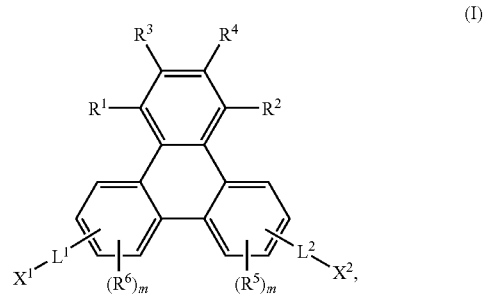

(I)

especially

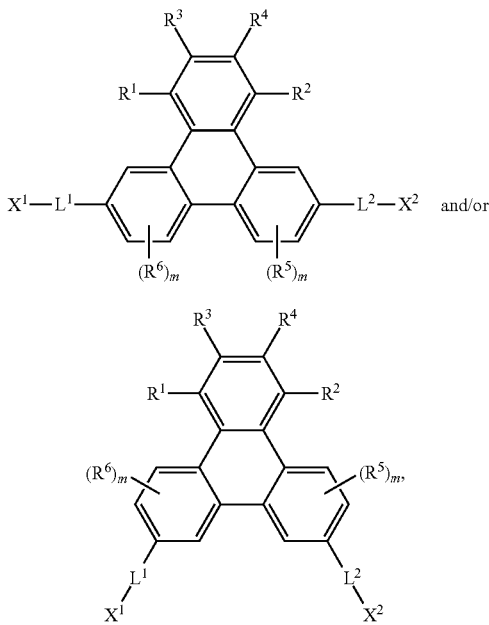

wherein R¹ and R² are independently of each other a $C_6$-$C_{24}$aryl group, or a $C_2$-$C_{30}$heteroaryl group, which can optionally be substituted, R³ and R⁴ are independently of each other hydrogen, a $C_1$-$C_{25}$alkyl group, a $C_6$-$C_{24}$aryl group, or a $C_2$-$C_{30}$heteroaryl group, which can optionally be substituted, X¹ is

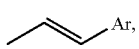

—NA¹A¹', —P(=O)A⁴A⁴', —SiA⁶A⁷A⁸, a $C_{10}$-$C_{28}$aryl group, which can optionally be substituted, or a $C_2$-$C_{30}$heteroaryl group, especially an electron deficient heteroaryl group, which can optionally be substituted, X² is

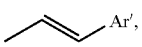

—NA²A²', —P(=O)A⁵A⁵', or —SiA⁶'A⁷'A⁸', a $C_{10}$-$C_{28}$aryl group, which can optionally be substituted, or a $C_2$-$C_{30}$heteroaryl group, especially an electron deficient heteroaryl group, which can optionally be substituted, Ar and Ar' are independently of each other $C_6$-$C_{14}$aryl, such as phenyl, or naphthyl, which may optionally be substituted by one or more groups selected from $C_1$-$C_{25}$alkyl, which may optionally be interrupted by —O—, or $C_1$-$C_{25}$alkoxy, L¹ and L² are independently of each other a single bond, or a bridging unit BU, such as

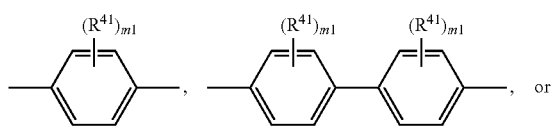

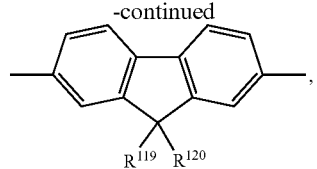

R⁵ and R⁶ are independently of each other halogen, or an organic substituent, or R⁵ and R⁶, which are adjacent to each other, together form an aromatic, or heteroaromatic ring, or ring system, which can optionally be substituted, A¹, A², A¹' and A²' are independently of each other a $C_6$-$C_{24}$aryl group, a $C_2$-$C_{30}$heteroaryl group, which can optionally be substituted, or A¹ and A¹' or A² and A²' or A³ and A³' together with the nitrogen atom to which they are bonded form a heteroaromatic ring, or ring system, such as

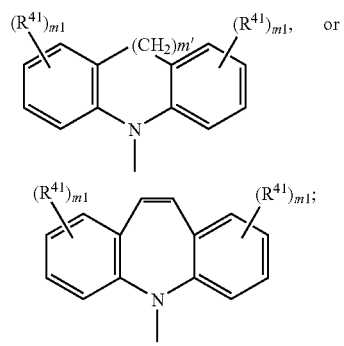

m' is 0, 1, or 2;

A⁴, A⁴', A⁶, A⁷, A⁸, A⁵, A⁵', A⁶', A⁷', and A⁸' are independently of each other a $C_6$-$C_{24}$aryl group, or a $C_2$-$C_{30}$heteroaryl group, which can optionally be substituted, m1 can be the same or different at each occurrence and is 0, 1, 2, 3, or 4, especially 0, 1, or 2, very especially 0 or 1, R¹¹⁹ and R¹²⁰ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or R¹¹⁹ and R¹²⁰ together form a group of formula =CR¹²¹R¹²², wherein R¹²¹ and R¹²² are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or R¹¹⁹ and R¹²⁰ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—R¹²⁷, and R¹²⁷ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, D is —CO—, —COO—, —S—, —SO—, —SO₂—, —O—, —NR⁶⁵—, —SiR⁷⁰R⁷¹—, —POR⁷²—, —CR⁶³=CR⁶⁴—, or —C≡C—, and E is —OR$^{69}$, —SR$^{69}$, —NR$^{65}$R$^{66}$, —COR$^{68}$, —COOR$^{67}$, —CONR$^{65}$R$^{66}$, —CN, or halogen, G is E, or C$_1$-C$_{18}$alkyl, R$^{63}$ and R$^{64}$ are independently of each other C$_6$-C$_{18}$aryl; C$_6$-C$_{18}$aryl which is substituted by C$_1$-C$_{18}$alkyl, C$_1$-C$_{18}$alkoxy; C$_1$-C$_{18}$alkyl; or C$_1$-C$_{18}$alkyl which is interrupted by —O—; or R$^{65}$, R$^{65'}$ and R$^{66}$ are independently of each other C$_6$-C$_{18}$aryl; C$_6$-C$_{18}$aryl which is substituted by C$_1$-C$_{18}$alkyl, C$_1$-C$_{18}$alkoxy; C$_1$-C$_{18}$alkyl; or C$_1$-C$_{18}$alkyl which is interrupted by —O—; or R$^{65}$ and R$^{66}$ together form a five or six membered ring, R$^{67}$ is C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R$^{68}$ is H; C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R$^{69}$ is C$_6$-C$_{18}$aryl; C$_6$-C$_{18}$aryl, which is substituted by C$_1$-C$_{18}$alkyl, C$_1$-C$_{18}$alkoxy; C$_1$-C$_{18}$alkyl; or C$_1$-C$_{18}$alkyl which is interrupted by —O—, R$^{70}$ and R$^{71}$ are independently of each other C$_1$-C$_{18}$alkyl, C$_6$-C$_{18}$aryl, or C$_6$-C$_{18}$aryl, which is substituted by C$_1$-C$_{18}$alkyl, and R$^{72}$ is C$_1$-C$_{18}$alkyl, C$_6$-C$_{18}$aryl, or C$_6$-C$_{18}$aryl, which is substituted by C$_1$-C$_{18}$alkyl;

R$^{41}$ can be the same or different at each occurrence and is Cl, F, CN, NR$^{45}$R$^{45'}$, a C$_1$-C$_{25}$alkyl group, a C$_4$-C$_{18}$cycloalkyl group, a C$_1$-C$_{25}$alkoxy group, in which one or more carbon atoms which are not in neighbourhood to each other could be replaced by —NR$^{45}$—, —O—, —S—, —C(═O)—O—, or —O—C(═O)—O—, and/or wherein one or more hydrogen atoms can be replaced by F, a C$_6$-C$_{24}$aryl group, or a C$_6$-C$_{24}$aryloxy group, wherein one or more carbon atoms can be replaced by O, S, or N, and/or which can be substituted by one or more non-aromatic groups R$^{41}$, or two or more groups R$^{41}$ form a ring system;

R$^{45}$ and R$^{45'}$ are independently of each other a C$_1$-C$_{25}$alkyl group, a C$_4$-C$_{18}$cycloalkyl group, in which one or more carbon atoms which are not in neighbourhood to each other could be replaced by —NR$^{45''}$—, —O—, —S—, —C(═O)—O—, or, —O—C(═O)—O—, and/or wherein one or more hydrogen atoms can be replaced by F, a C$_6$-C$_{24}$aryl group, or a C$_6$-C$_{24}$aryloxy group, wherein one or more carbon atoms can be replaced by O, S, or N, and/or which can be substituted by one or more non-aromatic groups R$^{41}$, R$^{45''}$ is a C$_1$-C$_{25}$alkyl group, or a C$_4$-C$_{18}$cycloalkyl group, and m can be the same or different at each occurrence and is 0, 1, 2, or 3, especially 0, 1, or 2, very especially 0 or 1.

In addition, the present invention relates to compounds of the formula

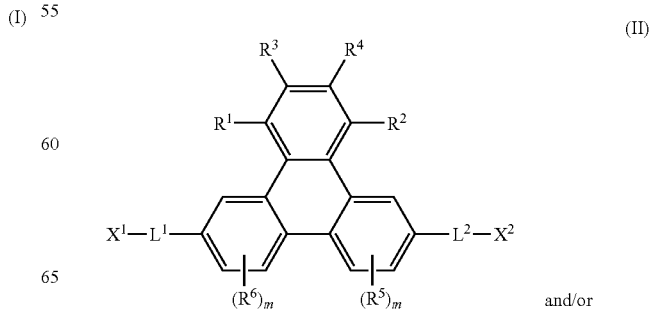

(I)

especially

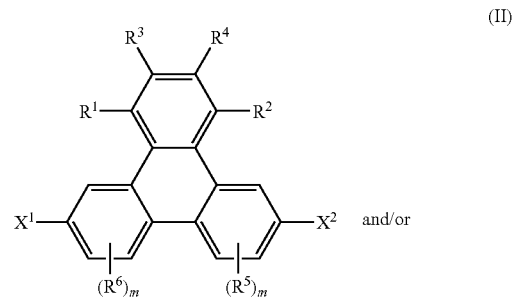

(II) and/or

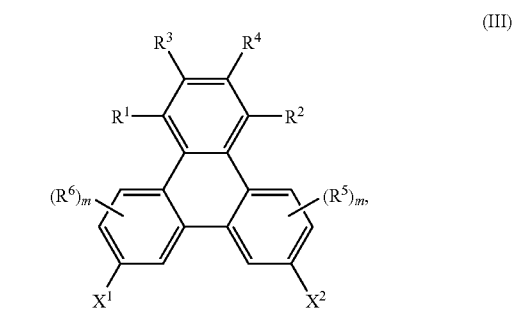

(III)

wherein X$^1$, X$^2$, R$^1$, R$^2$, R$^3$, R$^4$, R$^5$, R$^6$ and m are as defined above.

The compounds the present invention tend to be amorphous in solid state and, hence, can be processed either by sublimation, or from solution.

The electronic device of the present invention is preferably an electroluminescent (EL) device. The compounds of formula I can be used in organic light emitting diodes (OLEDs) as hosts for phosphorescent compounds. Accordingly, the present invention also provides electroluminescent devices comprising the compounds of formula I, especially an electroluminescent device comprising a cathode, an anode, and therebetween a light emitting layer containing a host material and a phosphorescent light-emitting material wherein the host material is a compound of formula I. In addition, the compounds of formula I may be used as hole, or electron blocking material and/or hole, or electron transport material.

Preferably, the compound of formula I is a compound of formula:

-continued

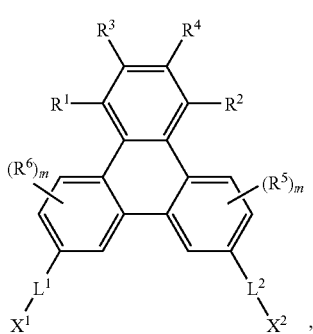

especially a compound according of formula

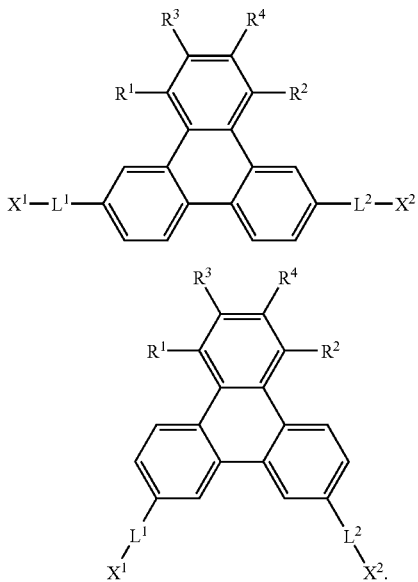

The compounds of the present invention are characterized in that $R^1$ and $R^2$ are a $C_6$-$C_{24}$aryl group, or a $C_2$-$C_{30}$heteroaryl group, which can optionally be substituted. Preferably, $R^1$ and $R^2$ area $C_6$-$C_{24}$aryl group, which can optionally be substituted, such as

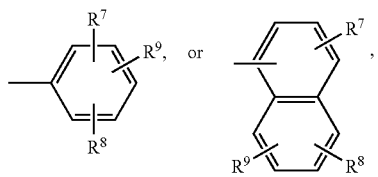

wherein $R^7$, $R^8$ and $R^9$ are independently of each other H, $C_1$-$C_{18}$alkyl, $C_1$-$C_{18}$alkoxy, or $C_1$-$C_{18}$alkyl which is interrupted by O.

In a preferred embodiment of the present invention $R^1$ and $R^2$ are a $C_6$-$C_{24}$aryl group, which can optionally be substituted, and $R^3$ is hydrogen and $R^4$ is a $C_1$-$C_{25}$alkyl group, or a $C_6$-$C_{24}$aryl group, which can optionally be substituted, or $R^3$ and $R^4$ are a $C_6$-$C_{24}$aryl group, which can optionally be substituted. Examples of a $C_6$-$C_{24}$aryl group, which can optionally be substituted, are

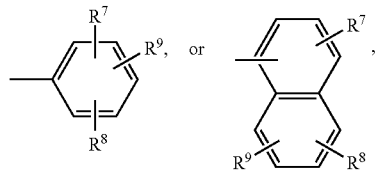

wherein $R^7$, $R^8$ and $R^9$ are as defined above.

In another preferred embodiment of the present invention $R^1$ and $R^2$ are a $C_2$-$C_{30}$heteroaryl group, which can optionally be substituted, and $R^3$ is hydrogen and $R^4$ is a $C_2$-$C_{30}$heteroaryl group, which can optionally be substituted, or $R^3$ and $R^4$ are a $C_2$-$C_{30}$heteroaryl group, which can optionally be substituted. Examples of a $C_2$-$C_{30}$heteroaryl group, which can optionally be substituted, are compounds of formula

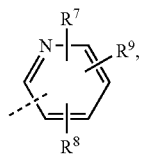

wherein $R^7$, $R^8$ and $R^9$ are as defined above.

Examples of $L^1$ and $L^2$ are a single bond, —(CR$^{47}$=CR$^{48}$)$_{m2}$—, -(Ar$^3$)$_{m3}$—, —[Ar$^3$(Y$^1$)$_{m5}$]$_{m4}$—, —[(Y$^1$)$_{m5}$Ar$^3$]$_{m4}$—, or —[Ar$^3$(Y$^2$)$_{m5}$Ar$^4$]$_{m4}$—, wherein Y$^1$, Y$^2$, R$^{47}$, R$^{48}$, Ar$^3$, Ar$^4$, m2, m3, m4 and m5 are as defined below. Preferably, $L^1$ and $L^2$ are a single bond, or a bridging unit BU of formula

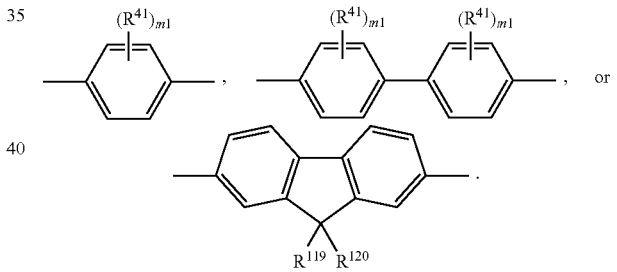

Examples of -$L^1$-$X^1$ and -$L^2$-$X^2$ are

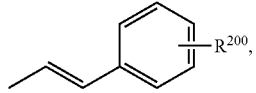

wherein $R^{200}$ is $C_1$-$C_{25}$alkyl, which may optionally be interrupted by —O—, or $C_1$-$C_{25}$alkoxy;

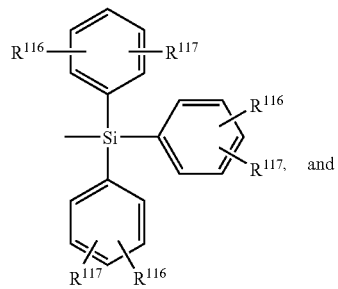

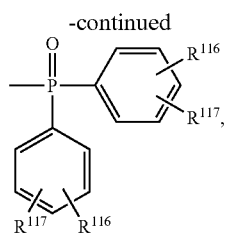

wherein $R^{116}$ and $R^{117}$ are as defined below. -$L^1$-$X^1$ is preferably a group

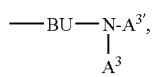

or —$NA^1A^{1'}$. -$L^2$-$X^2$ is preferably a group

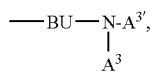

or —$NA^2A^{2'}$. $X^1$ and $X^2$ may be different, but are preferably the same.

In a preferred embodiment -$L^1$-$X^1$ and -$L^2$-$X^2$ are independently of each other a group of formula

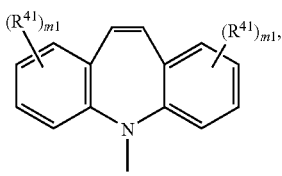

—$NA^1A^{1'}$, or a group

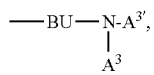

wherein $A^1$, $A^{1'}$, $A^3$ and $A^{3'}$ are independently of each other a $C_6$-$C_{24}$aryl group, or a $C_2$-$C_{30}$heteroaryl group, which can optionally be substituted, especially phenyl, naphthyl, anthryl, biphenylyl, 2-fluorenyl, phenanthryl, or perylenyl, which can optionally be substituted, such as

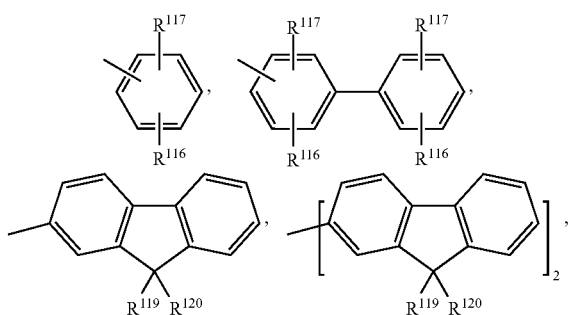

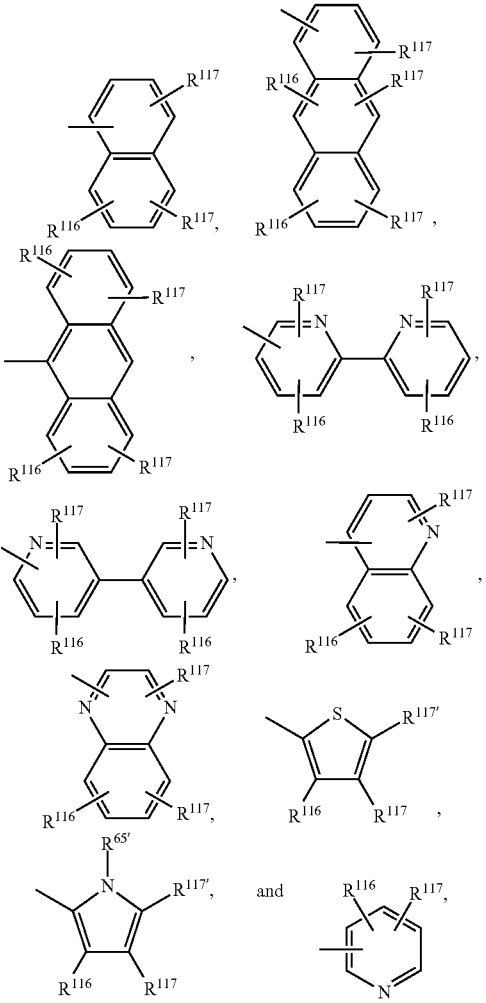

or $A^1$ and $A^{1'}$, or $A^3$ and $A^{3'}$ together with the nitrogen atom to which they are bonded form a heteroaromatic ring, or ring system, such as

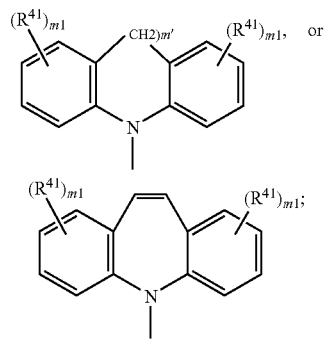

m' is 0, 1, or 2;

m1 can be the same or different at each occurrence and is 0, 1, 2, 3, or 4, especially 0, 1, or 2, very especially 0 or 1;

$R^{116}$, $R^{117}$ and $R^{117'}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{127}$, —C(=O)O$R^{127}$, or —C(=O)N$R^{127}R^{126}$, or substituents $R^{116}$, $R^{117}$ and $R^{117'}$, which are adjacent to each other, can form a ring, $R^{119}$ and $R^{120}$ are as defined above, $R^{126}$ and $R^{127}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, BU is

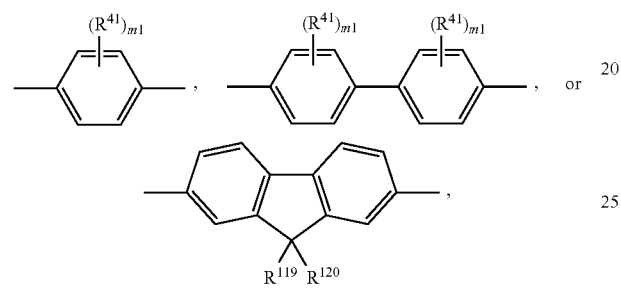

wherein $R^{41}$ is as defined above and m1 is as defined above; or -$L^1$-$X^1$ and -$L^2$-$X^2$ are independently of each other a group

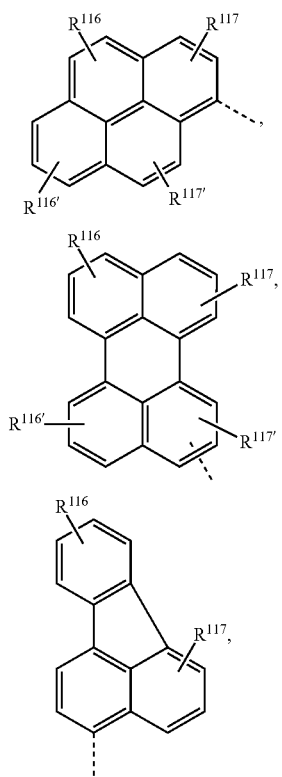

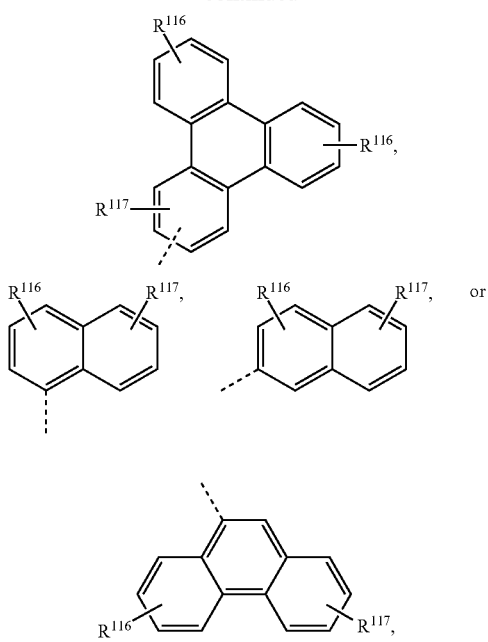

wherein $R^{116}$, $R^{116'}$, $R^{117}$ and $R^{117'}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{127}$, —C(=O)O$R^{127}$, or —C(=O)N$R^{127}R^{126}$, or substituents $R^{116}$, $R^{116'}$, $R^{117}$ and $R^{117'}$, which are adjacent to each other, can form a ring, $R^{126}$ and $R^{127}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, and D, E and G are as defined above; or -$L^1$-$X^1$ and -$L^2$-$X^2$ are independently of each other a group

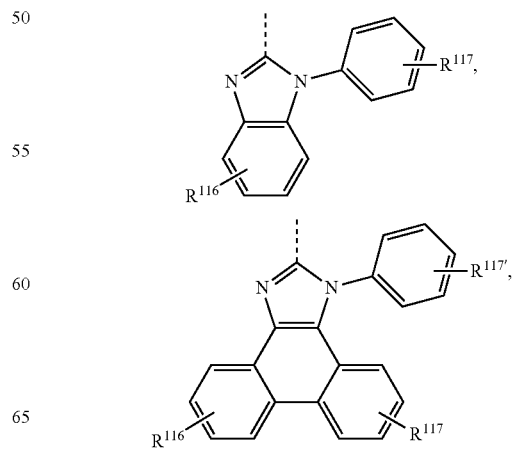

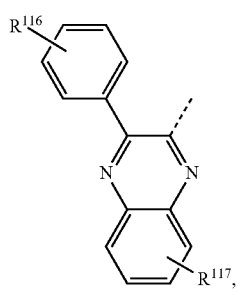
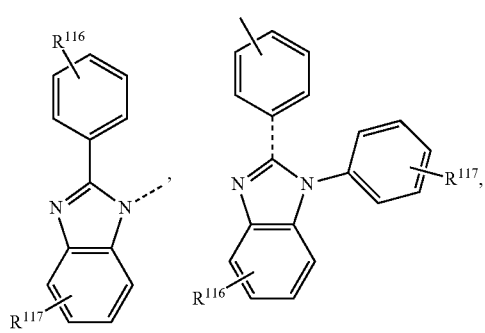
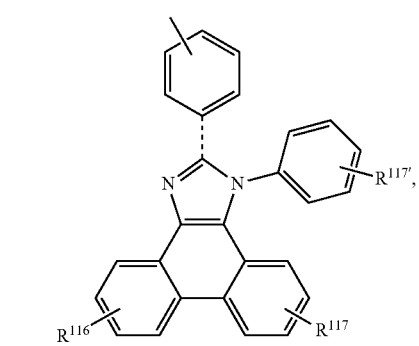
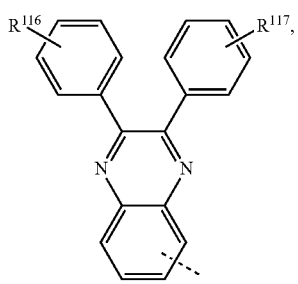
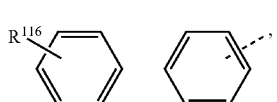
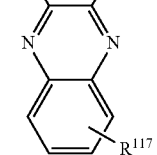
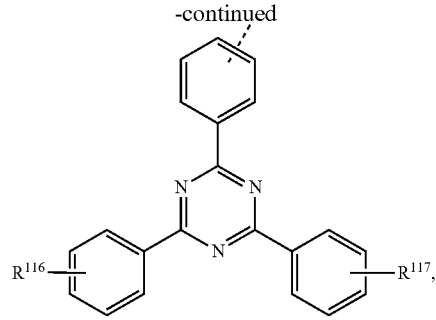
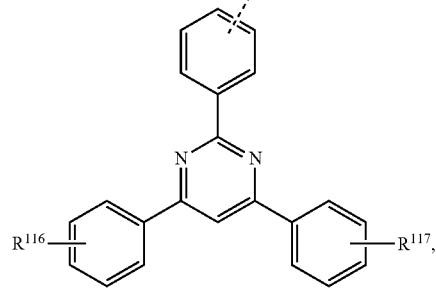
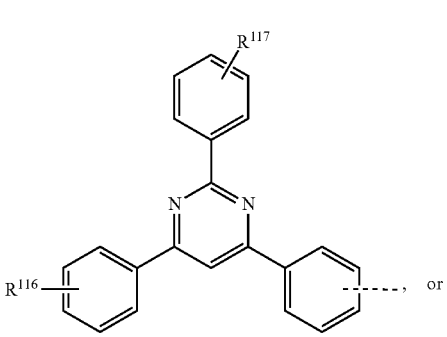
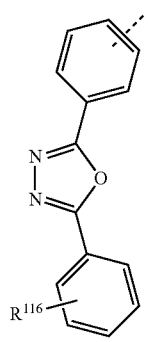
wherein $R^{116}$, $R^{117}$ and $R^{117'}$ are as defined above.
Even more preferred are compounds of the formula (I), wherein -$L^1$-$X^1$ and -$L^2$-$X^2$ are independently of each other a group of formula
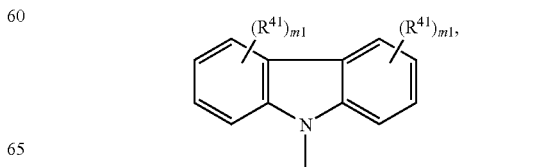

—NA¹A¹', or a group

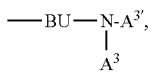

wherein

A¹, A¹', A³ and A³' are independently of each other

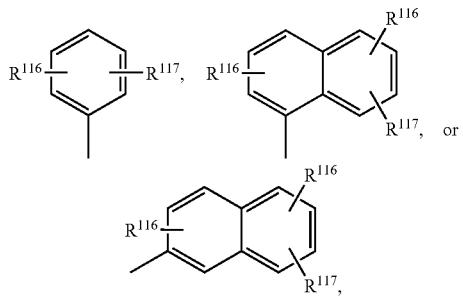

or A³ and A³' together with the nitrogen atom to which they are bonded form a group of formula

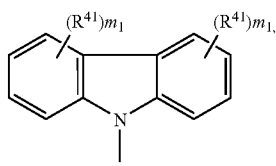

$R^{116}$ and $R^{117}$ are independently of each other $C_1$-$C_{25}$alkyl, which may optionally be interrupted by —O—, or $C_1$-$C_{25}$alkoxy;

BU is

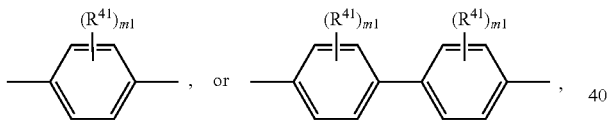

wherein $R^{41}$ can be the same or different at each occurrence and is $C_1$-$C_{25}$alkyl, which may optionally be interrupted by —O—, or $C_1$-$C_{25}$alkoxy; m1 is 0, 1, or 2.

Preferably, $R^{116}$, $R^{116'}$, $R^{117}$ and $R^{117'}$ are independently of each other H, $C_1$-$C_{12}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, or n-heptyl, $C_1$-$C_{12}$alkyl which is substituted by E and/or interrupted by D, such as —CH$_2$OCH$_3$, —CH$_2$OCH$_2$CH$_3$, —CH$_2$OCH$_2$CH$_2$OCH$_3$, or —CH$_2$OCH$_2$CH$_2$OCH$_2$CH$_3$, $C_6$-$C_{14}$aryl, such as phenyl, naphthyl, or biphenylyl, $C_5$-$C_{12}$cycloalkyl, such as cyclohexyl, $C_6$-$C_{14}$aryl which is substituted by G, such as —$C_6H_4$OCH$_3$, —$C_6H_4$OCH$_2$CH$_3$, —$C_6H_3$(OCH$_3$)$_2$, or —$C_6H_3$(OCH$_2$CH$_3$)$_2$, —$C_6H_4$CH$_3$, —$C_6H_3$(CH$_3$)$_2$, —$C_6H_2$(CH$_3$)$_3$, or —$C_6H_4$tBu.

Preferably, $R^{119}$ and $R^{120}$ are independently of each other $C_1$-$C_{12}$alkyl, such as methyl, ethyl, n-propyl, iso-propyl, n-butyl, sec-butyl, hexyl, octyl, or 2-ethyl-hexyl, $C_1$-$C_{12}$alkyl which is substituted by E and/or interrupted by D, such as —CH$_2$(OCH$_2$CH$_2$)$_w$OCH$_3$, w=1, 2, 3, or 4, $C_6$-$C_{14}$aryl, such as phenyl, naphthyl, or biphenylyl, $C_6$-$C_{14}$aryl which is substituted by G, such as —$C_6H_4$OCH$_3$, —$C_6H_4$OCH$_2$CH$_3$, —$C_6H_3$(OCH$_3$)$_2$, —$C_6H_3$(OCH$_2$CH$_3$)$_2$, —$C_6H_4$CH$_3$, —$C_6H_3$(CH$_3$)$_2$, —$C_6H_2$(CH$_3$)$_3$, or —$C_6H_4$tBu, or $R^{119}$ and $R^{120}$ together form a 4 to 8 membered ring, especially a 5 or 6 membered ring, such as cyclohexyl, or cyclopentyl, which can optionally be substituted by $C_1$-$C_8$alkyl.

D is preferably —CO—, —COO—, —S—, —SO—, —SO$_2$—, —O—, —NR$^{65}$—, wherein R$^{65}$ is $C_1$-$C_{12}$alkyl, such as methyl, ethyl, n-propyl, iso-propyl, n-butyl, isobutyl, or sec-butyl, or $C_6$-$C_{14}$aryl, such as phenyl, naphthyl, or biphenylyl.

E is preferably —OR$^{69}$; —SR$^{69}$; —NR$^{65}$R$^{65}$; —COR$^{68}$; —COOR$^{67}$; —CONR$^{65}$R$^{65}$; or —CN; wherein R$^{65}$, R$^{67}$, R$^{68}$ and R$^{69}$ are independently of each other $C_1$-$C_{12}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, naphthyl, or biphenylyl, which may optionally be substituted.

G has the same preferences as E, or is $C_1$-$C_{18}$alkyl, especially $C_1$-$C_{12}$alkyl, such as methyl, ethyl, n-propyl, iso-propyl, n-butyl, isobutyl, sec-butyl, hexyl, octyl, or 2-ethyl-hexyl.

Examples of

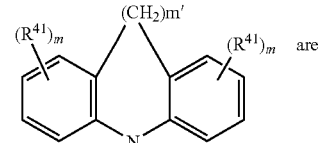

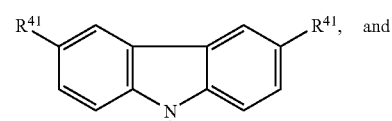

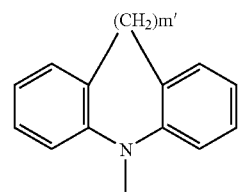

(m'=2), wherein $R^{41}$ is H, or $C_1$-$C_{18}$alkyl.

Examples of groups

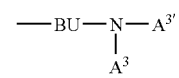

are shown below:

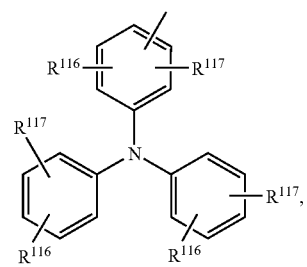

-continued

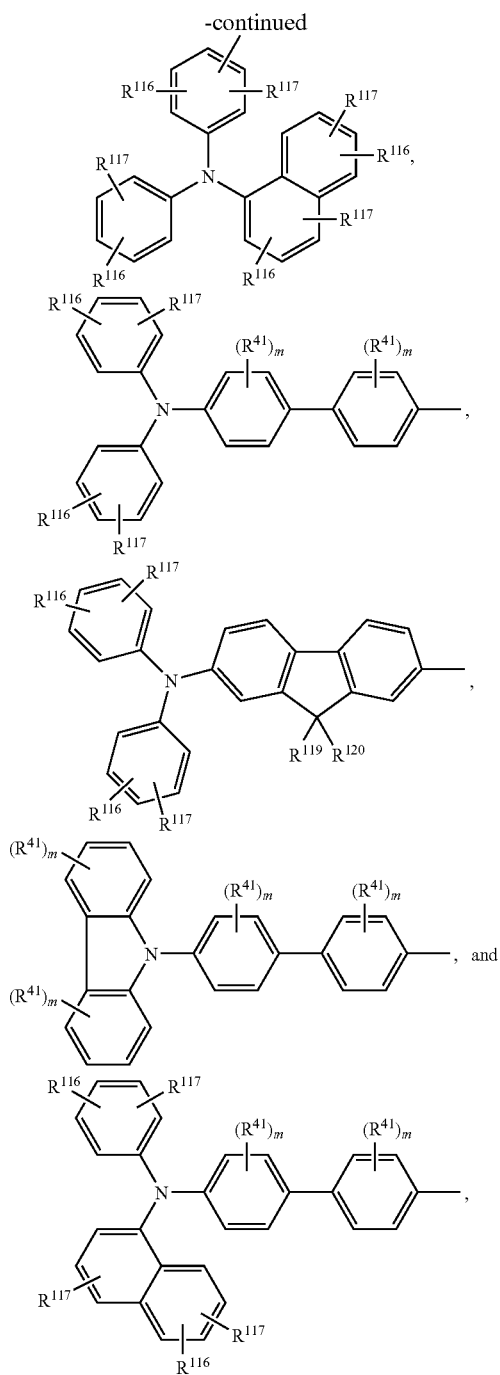

wherein $R^{41}$, $R^{116}$, $R^{117}$, $R^{119}$, $R^{120}$ and m are as defined above.

In another preferred embodiment of the present invention $X^1$ and $X^2$ are an electron deficient heteroaryl group.

The term "electron deficient heteroaryl group" means a group in which the isolated (unconnected) electron deficient heteroaryl unit has a HOMO of −5.3 eV or lower. Preferably at least one of $X^1$ and $X^2$, more preferably both of $X^1$ and $X^2$ are an electron deficient heteroaryl group.

The HOMO and LUMO energy levels for organic materials to be used in OLEDs have been estimated in several ways. The two common methods for estimating HOMO levels are solution electrochemistry and ultraviolet photoelectron spectroscopy (UPS). The most common method for determining oxidation and reduction potentials is cyclic voltametry, whereas the analyte or compound which corresponds to the group is dissolved with a high concentration of electrolyte. Electrodes are inserted and the voltage scanned in either the positive or negative direction (depending on whether an oxidation or reduction is performed). The presence of a redox reaction is indicated by current flowing through the cell. The voltage scan is then reversed and the redox reaction is reversed. If the areas of the two redox waves are the same the process is reversible. The potential at which these events occur give the value of the reduction or oxidation potential relative to a reference. The reference can be an external one, such as Ag/AgCl or SCE, or it can be an internal one, such as ferrocene, which has a known oxidation potential.

Although this is a solution process, in contrast to the solid state OLED, and the reference may be hard to adjust to give values relative to vacuum, the method is good for giving relative numbers. One useful parameter that may come from the electrochemical measurement is the carrier gap. If both the reduction and oxidation are reversible, one can determine the energy difference between the hole and the electron. This value is important to determine the LUMO energy from a well defined HOMO energy.

The preferred method to estimate HOMO energies in the solid state is UPS. This is a photoelectric measurement, where the solid is irradiated with UV photons. The energy of the photons is gradually increased until photo-generated electrons are evolved. The onset of ejected electrons gives the energy of the HOMO. The best accepted method for determining HOMO energies is UPS, which gives values in eV relative to vacuum. This is the binding energy for the electron.

A first energy level (HOMO or LUMO) is considered "less than" or "lower" than a second energy level if it is lower on a conventional energy level diagram, which means that the first energy level would have a value that is more negative than the second energy level.

Examples of such groups $-L^1-X^1$ and $-L^2-X^2$ are

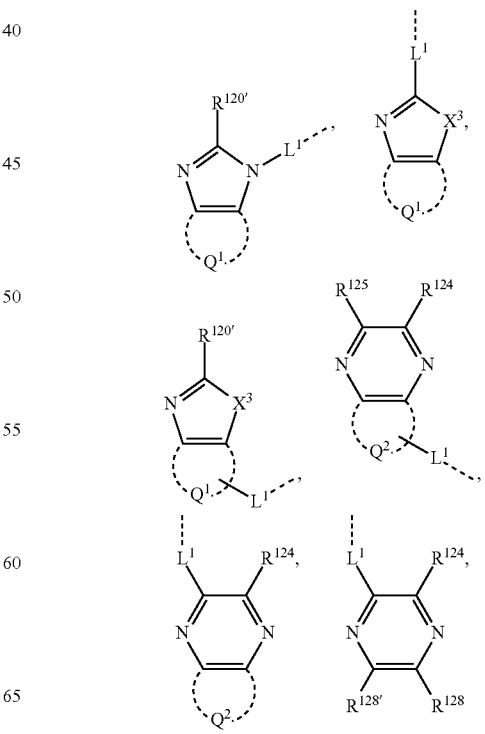

-continued

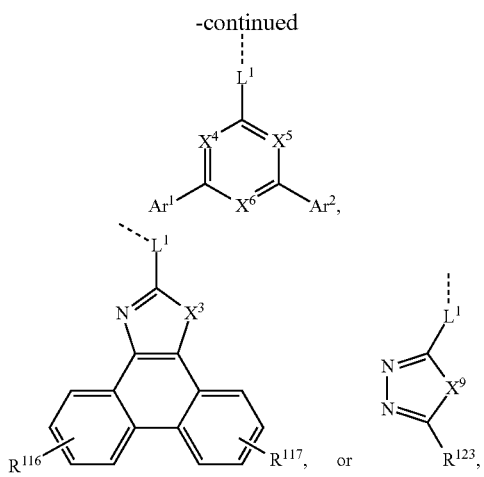

wherein
$X^3$ represents O, S or N—$R^{121'}$, especially N—$R^{121'}$,
$X^9$ represents O, S or N—$R^{121'}$, especially O,
$Q^1$ and $Q^2$ represents atoms necessary for forming a carbocyclic aromatic, or heterocyclic aromatic ring, which can optionally be condensed with other ring(s) to form a condensed ring, and/or can optionally be substituted by G,
$R^{116}$ and $R^{117}$ are as defined above,
$R^{121'}$ is H; $C_6$-$C_{18}$aryl; or $C_2$-$C_{20}$heteroaryl; which can optionally be substituted by $C_1$-$C_{18}$alkyl, $C_1$-$C_{18}$perfluoroalkyl, or $C_1$-$C_{18}$alkoxy; $C_1$-$C_{18}$alkyl; or $C_1$-$C_{18}$alkyl which is interrupted by —O—;
$R^{120'}$, $R^{123}$, $R^{124}$ and $R^{125}$ are independently of each other H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, which can optionally be substituted by G, $C_2$-$C_{20}$heteroaryl, which can optionally be substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl,
$R^{128}$ and $R^{128'}$ are independently of each other H, CN, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, which can optionally be substituted by G, $C_2$-$C_{20}$heteroaryl, which can optionally be substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl,
$L^1$ is a single bond, —$(CR^{47}$=$CR^{48})_{m2}$—, -$(Ar^3)_{m3}$—, —$[Ar^3(Y^1)_{m5}]_{m4}$—, —$[(Y^1)_{m5}Ar^4]_{m4}$—, or —$[Ar^3(Y^2)_{m5}Ar^4]_{m4}$—, wherein
$Y^1$ is —$(CR^{47}$=$CR^{48})$—,
$Y^2$ is $NR^{49}$, O, S, C=O, C(=O)O, wherein $R^{49}$ is $C_6$-$C_{18}$aryl which can optionally be substituted by $C_1$-$C_{18}$alkyl, or $C_1$-$C_{18}$alkoxy; $C_1$-$C_{18}$alkyl; or $C_1$-$C_{18}$alkyl which is interrupted by —O—;
$R^{47}$ and $R^{48}$ are independently of each other hydrogen, $C_1$-$C_{20}$alkyl, or $C_6$-$C_{24}$aryl, which can optionally be substituted by G,
m5 is an integer of 1 to 10, m2 is an integer of 1 to 10, m3 is an integer of 1 to 5, m4 is an integer of 1 to 5,
$Ar^3$ and $Ar^4$ are independently of each other arylen, or heteroarylen, which can optionally be substituted.
$X^4$, $X^5$ and $X^6$ are independently of each other N, or CH, with the proviso that at least one, preferably at least two of the substituents $X^4$, $X^5$ and $X^6$ are N, and
$Ar^1$ and $Ar^2$ are independently of each other $C_6$-$C_{24}$aryl, which can optionally be substituted by G, or $C_2$-$C_{20}$heteroaryl, which can optionally be substituted by G, wherein D, E and G are as defined above.
$R^{128}$ and $R^{128'}$ are preferably independently of each other H, CN, $C_1$-$C_{10}$alkyl, $C_1$-$C_{10}$alkyl which is substituted by E and/or interrupted by D, $C_1$-$C_{18}$perfluoroalkyl, $C_6$-$C_{24}$aryl, which can optionally be substituted by G, $C_2$-$C_{20}$heteroaryl, which can optionally be substituted by G, or $C_7$-$C_{25}$aralkyl.
$R^{120'}$, $R^{123}$, $R^{124}$ and $R^{125}$ are preferably independently of each other H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, which can optionally be substituted by G, or $C_2$-$C_{20}$heteroaryl, which can optionally be substituted by G, Specific examples of the aromatic heterocyclic ring formed by $Q^1$, or $Q^2$ include pyridine, pyrazine, pyrimidine, pyridazine and triazine. Preferred are pyridine, pyrazine, pyrimidine and pyridazine, with pyridine and pyrazine being more preferred, and pyridine being still more preferred. The (6-membered) aromatic heterocyclic ring formed by $Q^1$, or $Q^2$ may be condensed with other ring(s) to form a condensed ring, or may have a substituent G.

In this aspect of the present invention, more specific examples of the groups -$L^1$-$X^1$ and -$L^1$-$X^2$ are the following groups:

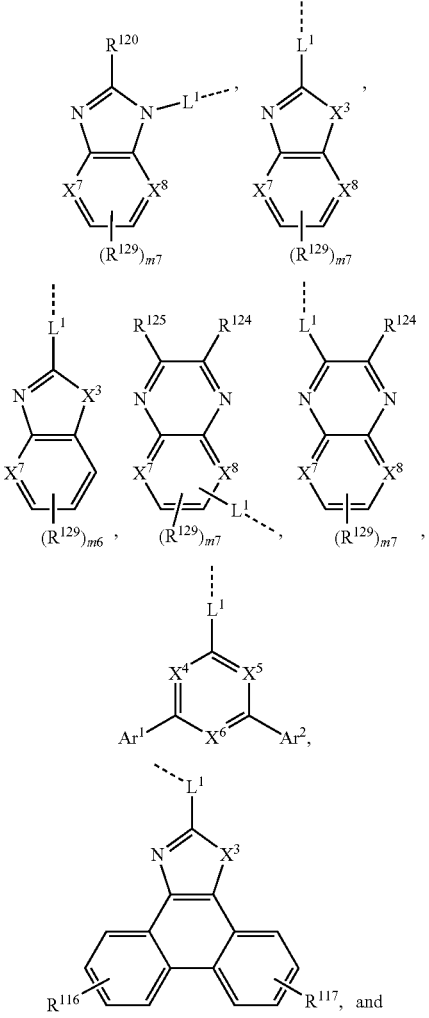

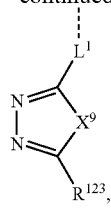

wherein m6 is 0, or an integer 1 to 3,
m7 is 0, 1, or 2,
$R^{116}$ and $R^{117}$ are as defined above,
$R^{123}$, $Ar^1$ and $Ar^2$ are independently of each other phenyl or 1- or 2-naphthyl which can be substituted one to three times with $C_1$-$C_{18}$alkyl, $C_1$-$C_{18}$alkyl, which can optionally be interrupted by O; or $C_1$-$C_{18}$alkoxy, which can optionally be interrupted by O,
$R^{129}$ can be the same or different at each occurrence and is F, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{130}$, —C(=O)O$R^{130'}$, or —C(=O)N$R^{131}R^{131'}$, or substituents $R^{129}$, which are adjacent to each other, can form a ring,
$R^{131}$ and $R^{131'}$ are independently of each other H; $C_6$-$C_{18}$aryl; or $C_2$-$C_{20}$heteroaryl; which can optionally be substituted by $C_1$-$C_{18}$alkyl, $C_1$-$C_{18}$perfluoroalkyl, or $C_1$-$C_{18}$alkoxy; $C_1$-$C_{18}$alkyl; or $C_1$-$C_{18}$alkyl which is interrupted by —O—;
$R^{130}$ and $R^{130'}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—,
$X^7$ and $X^8$ are independently of each other N, or $CR^{127''}$, wherein $R^{127''}$ has the meaning of $R^{126}$, and $R^{120'}$, $R^{124}$, $R^{125}$, $X^3$, $X^4$, $X^5$, $X^6$, $X^9$ and $L^1$ are as defined above.

Among the above groups -$L^1$-$X^1$ and -$L^1$-$X^2$ the following groups are even more preferred:

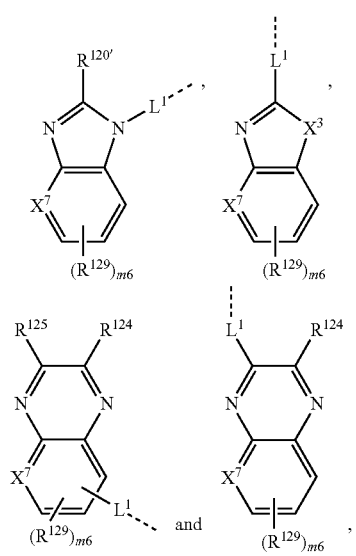

wherein the following groups are most preferred:

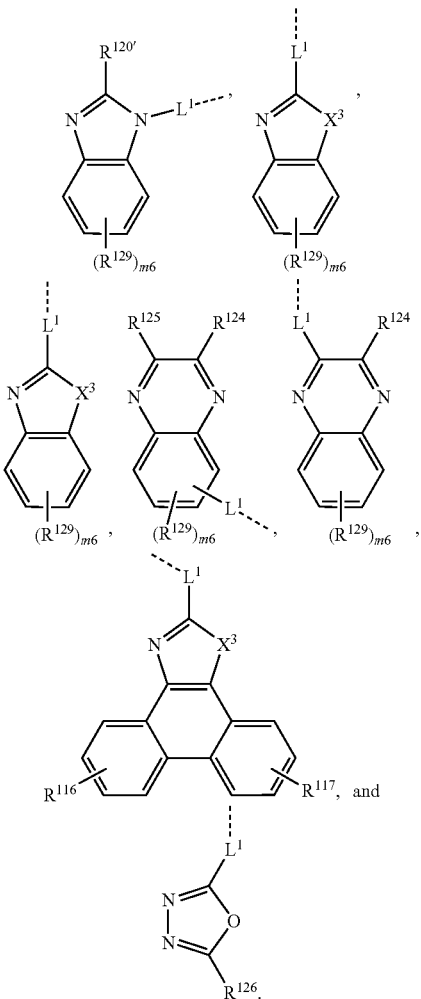

$L^1$ is preferably a single bond, or a group

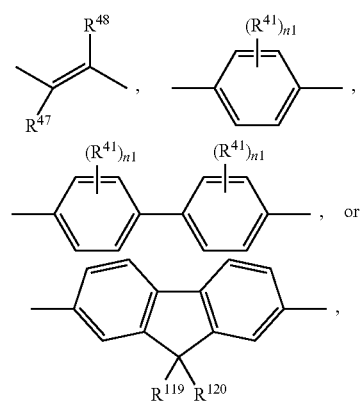

wherein $R^{41}$ can be the same or different at each occurrence and is F, CN, N($R^{45}$)$_2$, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by —N$R^{45}$—, —O—, —S—, —C(=O)—O—, or —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, or two or more groups $R^{41}$ form a ring system;

$R^{45}$ is a $C_1$-$C_{25}$alkyl group, a $C_4$-$C_{18}$cycloalkyl group, in which one or more carbon atoms which are not in neighbourhood to each other could be replaced by —$NR^{45''}$—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, and $R^{45''}$ is a $C_1$-$C_{25}$alkyl group, or a $C_4$-$C_{18}$cycloalkyl group, n1 is 0, or an integer 1 to 3, and $R^{47}$, $R^{48}$, $R^{119}$ and $R^{120}$ are as defined above. Most preferred for $L^1$ are a single bond, or a group

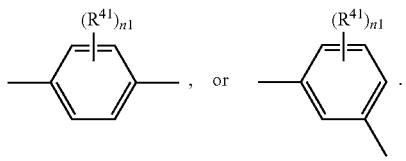

In a particularly preferred embodiment of the present invention -$L^1$-$X^1$ and -$L^2$-$X^2$ are independently of each other a group

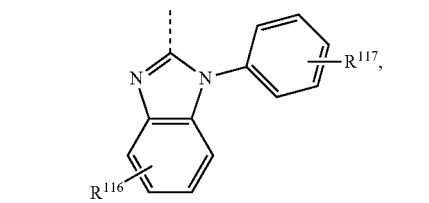

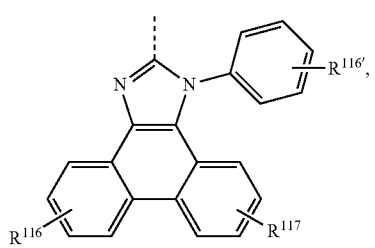

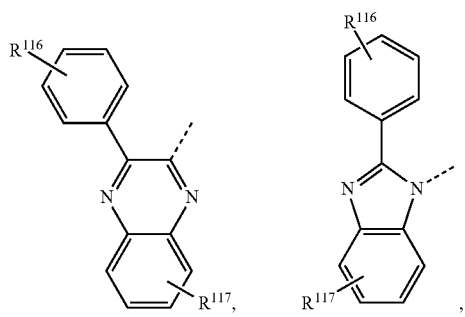

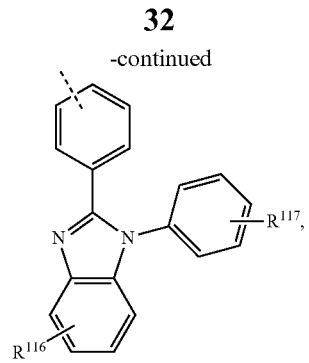

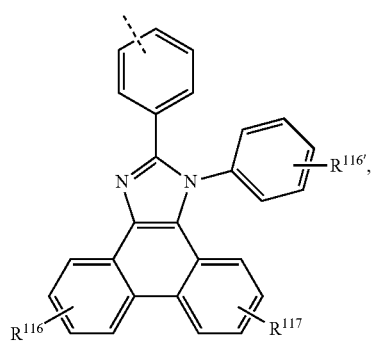

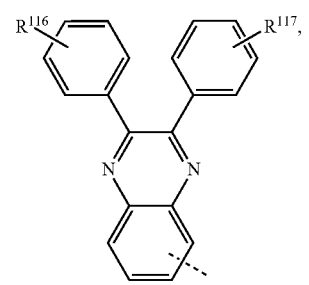

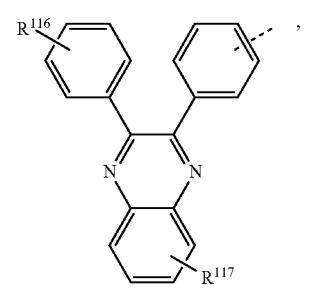

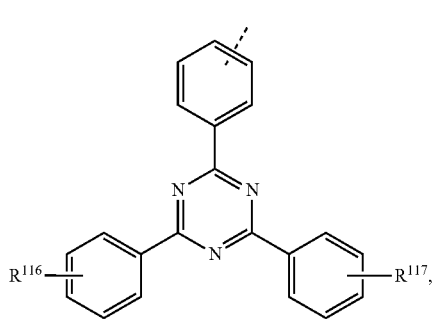

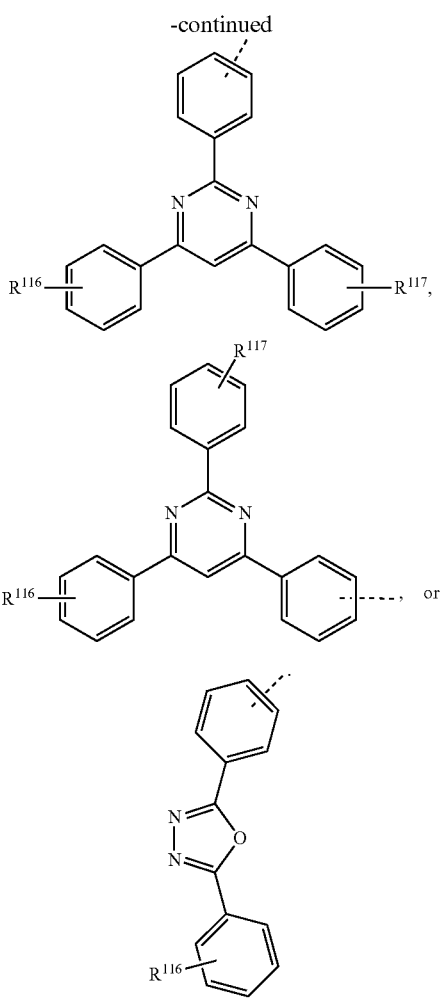

In another preferred embodiment of the present invention -L$^1$-X$^1$ and -L$^2$-X$^2$ are independently of each other a group

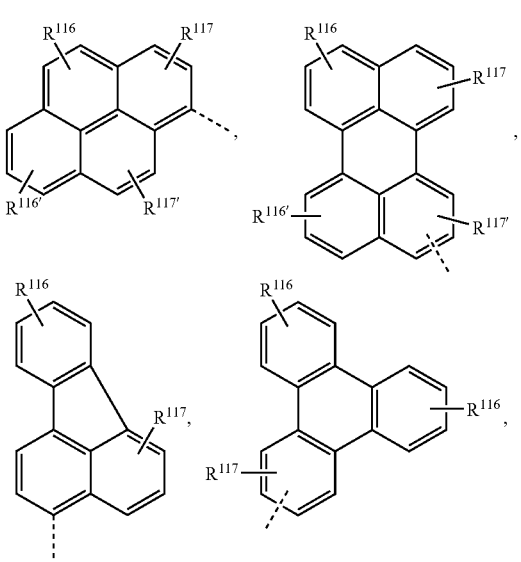

wherein

R$^{116}$, R$^{116'}$, R$^{117}$ and R$^{117'}$ are independently of each other H, halogen, —CN, C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, C$_7$-C$_{25}$aralkyl, —C(=O)—R$^{127'}$, —C(=O)OR$^{127'}$, or —C(=O)NR$^{127'}$R$^{126'}$, or substituents R$^{116}$, R$^{116'}$, R$^{117}$ and R$^{117'}$, which are adjacent to each other, can form a ring, R$^{126'}$ and R$^{127'}$ are independently of each other H; C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, D, E and G are as defined above.

Preferably, R$^{116}$, R$^{116'}$, R$^{117}$ and R$^{117'}$ are independently of each other H, F, —CN, C$_1$-C$_{18}$alkyl, C$_1$-C$_{18}$alkyl which is substituted by E and/or interrupted by D, C$_1$-C$_{18}$alkoxy, C$_1$-C$_{18}$alkoxy, which is substituted by E and/or interrupted by D, C$_6$-C$_{24}$aryl, C$_6$-C$_{24}$aryl which is substituted by G, D is —O—; —NR$^{65}$—; and E is —OR$^{69}$; —NR$^{65}$R$^{66}$; —CN; or F;

G is E, C$_1$-C$_{18}$alkyl, C$_1$-C$_{18}$alkyl which is interrupted by O, C$_1$-C$_{18}$alkoxy, or C$_1$-C$_{18}$alkoxy which interrupted by O, wherein R$^{65}$ and R$^{66}$ are independently of each other C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—; or R$^{65}$ and R$^{66}$ together form a five or six membered ring, and R$^{69}$ is C$_6$-C$_{18}$aryl; C$_6$-C$_{18}$aryl, which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—.

Examples of particularly preferred compounds are compounds A1-A21, B1-B21, C1-C21, and D1-D21, which are shown in claim 7.

The compounds of the formula I, wherein -L$^1$-X$^1$ and -L$^2$-X$^2$ are independently of each other —NA$^1$A$^{1'}$,

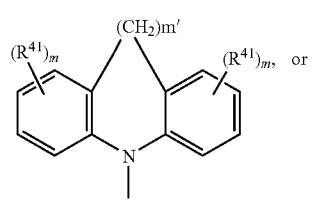

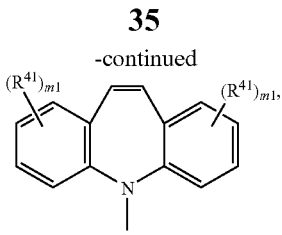

can, for example, be prepared according to a process, which comprises reacting a compound of formula

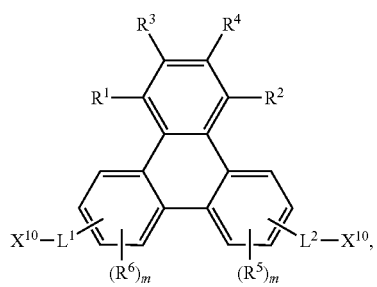

(XX)

wherein $X^{10}$ stands for halogen, such as bromo or iodo, with a compound of formula $HNA^1A^{1'}$,

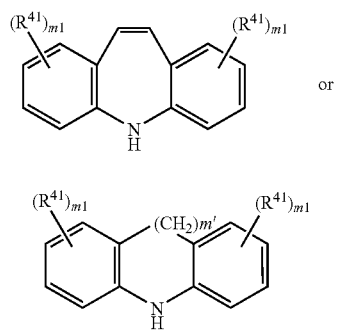

or in the presence of a base, such as sodium hydride, potassium carbonate, or sodium carbonate, and a catalyst, such as copper (0) or copper (I) (such as copper, copper-bronze, copper bromide iodide, or copper bromide), in a solvent, such as toluene, dimethyl formamide, or dimethyl sulfoxide, wherein $A^1$, $A^{1'}$, $L^1$, $L^2$, $R^1$, $R^2$, $R^3$, $R^4$, $R^5$, $R^6$, $R^{41}$, m1 and m are as defined above.

This reaction, referred to as an Ullmann condensation, is described by Yamamoto & Kurata, Chem. and Industry, 737-738 (1981), J. Mater. Chem. 14 (2004) 2516, H. B. Goodbrand et al., J. Org. Chem. 64 (1999) 670 and k. D. Belfield et al., J. Org. Chem. 65 (2000) 4475 using copper as catalyst. Additionally palladium catalysts can be used for the coupling of aryl halogen compounds with amines, as described in M. D. Charles et al., Organic Lett. 7 (2005) 3965, A. F. Littke et. al., Angew. Chem. Int. Ed. 41 (2002) 4176 and literature cited therein.

The compounds of formula XX are known from WO08/012250, or can be prepared according, or in analogy to the methods described therein.

The compounds, wherein $X^1$ and $X^2$ are a group

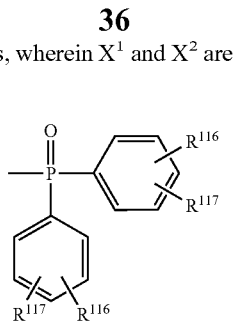

can be prepared according to P. A. Vecchi et al., Org. Lett. 8 (2006) 4211-4214.

The compounds, wherein $X^1$ and $X^2$ are a group

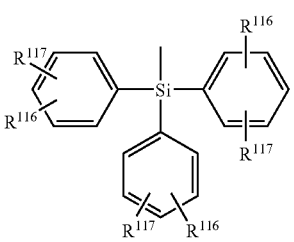

can be prepared according to example IV of US2005/0175857.

Halogen is fluorine, chlorine, bromine and iodine.

$C_1$-$C_{25}$alkyl is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

$C_2$-$C_{25}$alkenyl groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-24}$alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_1$-$C_{18}$perfluoroalkyl, especially $C_1$-$C_4$perfluoroalkyl, is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

The terms "haloalkyl, haloalkenyl and haloalkynyl" mean groups given by partially or wholly substituting the abovementioned alkyl group, alkenyl group and alkynyl group with halogen, such as trifluoromethyl etc. The "aldehyde group, ketone group, ester group, carbamoyl group and amino group" include those substituted by an alkyl group, a cycloalkyl group, an aryl group, an aralkyl group or a heterocyclic group, wherein the alkyl group, the cycloalkyl group, the aryl group, the aralkyl group and the heterocyclic group may be unsubstituted or substituted. The term "silyl group" means a group of formula —$SiR^{62'}R^{63'}R^{64'}$, wherein $R^{62'}$, $R^{63'}$ and $R^{64'}$ are independently of each other a $C_1$-$C_8$alkyl group, in particular a $C_1$-$C_4$alkyl group, a $C_6$-$C_{24}$aryl group or a $C_7$-$C_{12}$aralkyl group, such as a trimethylsilyl group. The term "siloxanyl group" means a group of formula —O—$SiR^{62'}R^{63'}R^{64'}$, wherein $R^{62'}$, $R^{63'}$ and $R^{64'}$ are as defined above, such as a trimethylsiloxanyl group.

The term "cycloalkyl group" is typically $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The term "cycloalkenyl group" means an unsaturated alicyclic hydrocarbon group containing one or more double bonds, such as cyclopentenyl, cyclopentadienyl, cyclohexenyl and the like, which may be unsubstituted or substituted. The cycloalkyl group, in particular a cyclohexyl group, can be condensed one or two times by phenyl which can be substituted one to three times with $C_1$-$C_4$-alkyl, halogen and cyano. Examples of such condensed cyclohexyl groups are:

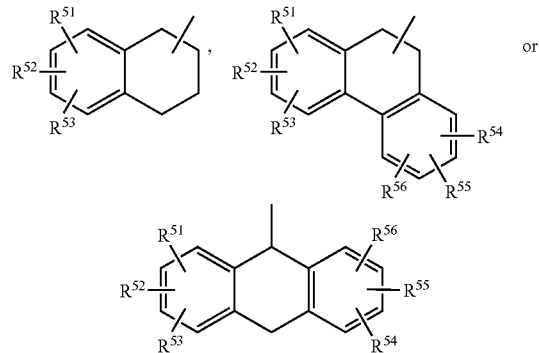

in particular

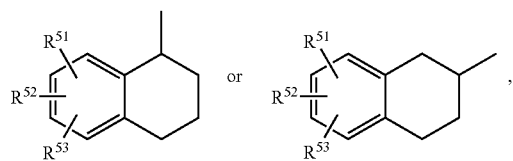

wherein $R^{51}$, $R^{52}$, $R^{53}$, $R^{54}$, $R^{55}$ and $R^{56}$ are independently of each other $C_1$-$C_8$-alkyl, $C_1$-$C_8$-alkoxy, halogen and cyano, in particular hydrogen.

Aryl is usually $C_6$-$C_{30}$aryl, preferably $C_6$-$C_{24}$aryl, which optionally can be substituted, such as, for example, phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, anthryl, tetracyl, pentacyl, hexacyl, or quaderphenylyl, which may be unsubstituted or substituted.

The term "aralkyl group" is typically $C_7$-$C_{24}$aralkyl, such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted.

The term "aryl ether group" is typically a $C_{6-24}$aryloxy group, that is to say O—$C_{6-24}$aryl, such as, for example, phenoxy or 4-methoxyphenyl. The term "aryl thioether group" is typically a $C_{6-24}$arylthio group, that is to say S—$C_{6-24}$aryl, such as, for example, phenylthio or 4-methoxyphenylthio. The term "carbamoyl group" is typically a $C_{1-18}$carbamoyl radical, preferably $C_{1-8}$carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

The terms "aryl" and "alkyl" in alkylamino groups, dialkylamino groups, alkylarylamino groups, arylamino groups and diaryl groups are typically $C_1$-$C_{25}$alkyl and $C_6$-$C_{24}$aryl, respectively.

Alkylaryl refers to alkyl-substituted aryl radicals, especially $C_7$-$C_{12}$alkylaryl. Examples are tolyl, such as 3-methyl-, or 4-methylphenyl, or xylyl, such as 3,4-dimethylphenyl, or 3,5-dimethylphenyl.

Heteroaryl is typically $C_2$-$C_{26}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

Examples of a five or six membered ring formed by, for example, $R^{65}$ and $R^{66}$, respectively are heterocycloalkanes or heterocycloalkenes having from 3 to 5 carbon atoms which can have one additional hetero atom selected from nitrogen, oxygen and sulfur, for example

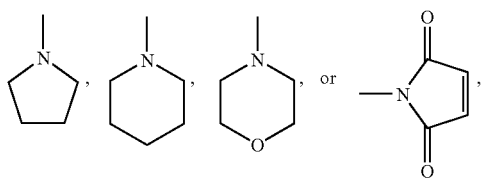

which can be part of a bicyclic system, for example

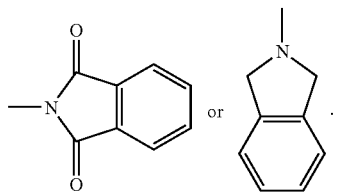

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group, wherein $C_1$-$C_8$alkyl, $C_1$-$C_8$alkoxy, a cyano group, or a silyl group are preferred.

If a substituent, such as, for example $R^6$ occurs more than one time in a group, it can be different in each occurrence.

The wording "substituted by G" means that one, or more, especially one to three substituents G might be present.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl or alkylaryl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—CH($C_2H_5$)$C_4H_9$), $CH_2$—CH(OR$^{y'}$)—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H;

$C_1$-$C_8$alkylene-COO—$R^z$, e.g. $CH_2COOR_z$, $CH(CH_3)CO$-$OR^z$, $C(CH_3)_2COOR^z$, where $R^z$ is H, $C_1$-$C_{18}$alkyl, $(CH_2CH_2O)_{1-9}$—$R^x$, and $R^x$ embraces the definitions indicated above; $CH_2CH_2$—O—CO—CH=$CH_2$; $CH_2CH(OH)$ $CH_2$—O—CO—C($CH_3$)=$CH_2$.

Preferred arylene radicals are 1,4-phenylene, 2,5-tolylene, 1,4-naphthylene, 1,9-antracylene, 2,7-phenantrylene and 2,7-dihydrophenantrylene.

Preferred heteroarylene radicals are 2,5-pyrazinylene, 3,6-pyridazinylene, 2,5-pyridinylene, 2,5-pyrimidinylene, 1,3,4-thiadiazol-2,5-ylene, 1,3-thiazol-2,4-ylene, 1,3-thiazol-2,5-ylene, 2,4-thiophenylene, 2,5-thiophenylene, 1,3-oxazol-2,4-ylene, 1,3-oxazol-2,5-ylene and 1,3,4-oxadiazol-2,5-ylene, 2,5-indenylene and 2,6-indenylene.

The electronic device of the present invention is preferably an electroluminescent (EL) device. The compounds of formula I can be used in organic light emitting diodes (OLEDs) as hosts for phosphorescent compounds. Accordingly, the present invention also relates to an electroluminescent device, comprising a compound of formula I. In a preferred embodiment the electroluminescent device comprising a cathode, an anode, and therebetween a light emitting layer containing a host material and a phosphorescent light-emitting material wherein the host material is a compound of formula I.

Suitably, the light-emitting layer of the OLED device comprises a host material and one or more guest materials for emitting light. At least one of the host materials is a compound comprising a compound of formula I. The light-emitting guest material(s) is usually present in an amount less than the amount of host materials and is typically present in an amount of up to 15 wt % of the host, more typically from 0.1 to 10 wt % of the host, and commonly from 2 to 8% of the host. For convenience, the phosphorescent complex guest material may be referred to herein as a phosphorescent material. The emissive layer may comprise a single material, that combines transport and emissive properties. Whether the emissive material is a dopant or a major constituent, emissive layer may comprise other materials, such as dopants that tune the emission of the emissive layer. The emissive layer may include a plurality of emissive materials capable of, in combination, emitting a desired spectrum of light.

Other Host Materials for Phosphorescent Materials

The host material useful in the invention may be used alone or in combination with other host materials. Other host materials should be selected so that the triplet exciton can be transferred efficiently from the host material to the phosphorescent material. Suitable host materials are described in WO00/70655; 01/39234; 01/93642; 02/074015; 02/15645, and US20020117662. Suitable hosts include certain aryl amines, triazoles, indoles and carbazole compounds. Examples of hosts are 4,4'-N,N'-dicarbazole-biphenyl (CBP), 2,2'-dimethyl-4,4'-N,N'-dicarbazole-biphenyl, m-(N,N'-dicarbazole)benzene, and poly(N-vinylcarbazole), including their derivatives.

Desirable host materials are capable of forming a continuous film. The light-emitting layer may contain more than one host material in order to improve the device's film morphology, electrical properties, light emission efficiency, and lifetime. The light emitting layer may contain a first host material that has good hole-transporting properties, and a second host material that has good electron-transporting properties.

Phosphorescent Materials

Phosphorescent materials may be used alone or, in certain cases, in combination with each other, either in the same or different layers. Examples of phosphorescent and related materials are described in WO00/57676, WO00/70655, WO01/41512, WO02/15645, US2003/0017361, WO01/93642, WO01/39234, U.S. Pat. No. 6,458,475, WO02/071813, U.S. Pat. No. 6,573,651, US2002/0197511, WO02/074015, U.S. Pat. No. 6,451,455, US2003/0072964, US2003/0068528, U.S. Pat. Nos. 6,413,656, 6,515,298, 6,451,415, 6,097,147, US2003/0124381, US2003/0059646, US2003/0054198, EP1239526, EP1238981, EP1244155, US2002/0100906, US2003/0068526, US2003/0068535, JP2003073387, JP2003073388, US2003/0141809, US2003/0040627, JP2003059667, JP2003073665 and US2002/0121638.

The emission wavelengths of cyclometallated Ir(III) complexes of the type IrL$_3$ and IrL$_2$L', such as the green-emitting fac-tris(2-phenylpyridinato-N,$C^{2'}$)iridium(III) and bis(2-phenylpyridinato-N,$C^{2'}$)Iridium(III) (acetylacetonate) may be shifted by substitution of electron donating or withdrawing groups at appropriate positions on the cyclometallating ligand L, or by choice of different heterocycles for the cyclometallating ligand L. The emission wavelengths may also be shifted by choice of the ancillary ligand L'. Examples of red emitters are bis(1-(phenyl)isoquinoline)iridium (III) acetylanetonate, (acetylanetonato)bis-(2,3,5-triphenylpyrazinato) iridium(III), bis(2-(2'-benzothienyl)pyridinato-N,$C^{3'}$)iridium(III)-(acetylacetonate) and tris(1-phenylisoquinolinato-N,C)iridium(III). A blue-emitting example is bis(2-(4,6-diflourophenyl)-pyridinato-N,$C^{2'}$)Iridium(III)(picolinate).

Red electrophosphorescence has been reported, using bis (2-(2'-benzo[4,5-a]thienyl)pyridinato-N,$C^3$)iridium(acetylacetonate)[Btp₂Ir(acac)] as the phosphorescent material (Adachi, C., Lamansky, S., Baldo, M. A., Kwong, R. C., Thompson, M. E., and Forrest, S. R., App. Phys. Lett., 78, 1622 1624 (2001)).

Other important phosphorescent materials include cyclo-metallated Pt(II) complexes such as cis-bis(2-phenylpyridi-nato-N,C$^{2'}$)platinum(II), cis-bis(2-(2'-thienyl)pyridinato-N, C$^{3'}$)platinum(II), cis-bis(2-(2'-thienyl)quinolinato-N,C$^{5'}$) platinum(II), or (2-(4,6-diflourophenyl)pyridinato-NC2') platinum(II)acetylacetonate. Pt(II)porphyrin complexes such as 2,3,7,8,12,13,17,18-octaethyl-21H,23H-porphine platinum(H) are also useful phosphorescent materials.

Still other examples of useful phosphorescent materials include coordination complexes of the trivalent lanthanides such as Th$^{3+}$ and Eu$^{3+}$ (J. Kido et al, Appl. Phys. Lett., 65, 2124 (1994)).

Other important phosphorescent materials are described in WO06/000544 and PCT/EP2008/051702.

Examples of phosphorescent materials are compounds A-1 to B-234, B-1 to B-234, C-1 to C-44 and D-1 to D-234, which are described in PCT/EP2008/051702:

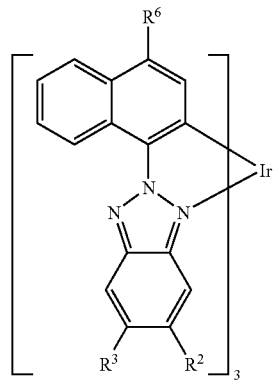

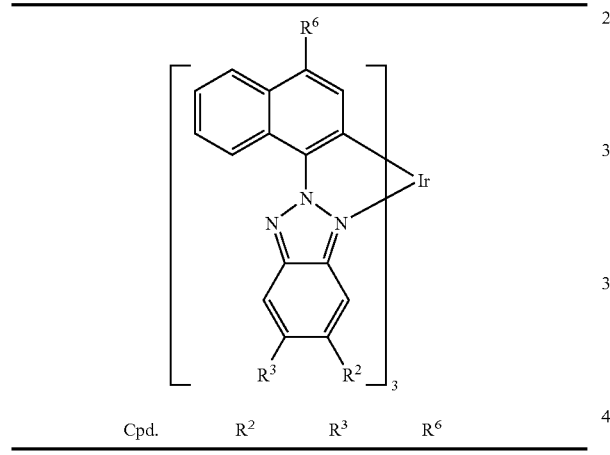

| Cpd. | R² | R³ | R⁶ |
|---|---|---|---|
| A-1 | H | H | H |
| A-2 | H | H | OCH₃ |
| A-3 | H | H | OCH₂CH₃ |
| A-4 | H | H | O-n-butyl |
| A-5 | H | H | O-iso-butyl |
| A-6 | H | H | O-2-butyl |
| A-7 | H | H | O-2-ethylhexyl |
| A-8 | H | H | N(CH₃)₂ |
| A-9 | H | H | NPh₂ |
| A-10 | H | CF₃ | H |
| A-11 | CF₃ | H | H |
| A-12 | H | CF₃ | OCH₃ |
| A-13 | CF₃ | H | OCH₃ |
| A-14 | H | CF₃ | OCH₂CH₃ |
| A-15 | CF₃ | H | OCH₂CH₃ |
| A-16 | H | CF₃ | O-n-butyl |
| A-17 | CF₃ | H | O-n-butyl |
| A-18 | H | CF₃ | O-iso-butyl |
| A-19 | CF₃ | H | O-iso-butyl |
| A-20 | H | CF₃ | O-2-butyl |
| A-21 | CF₃ | H | O-2-butyl |
| A-22 | H | CF₃ | O-2-ethylhexyl |
| A-23 | CF₃ | H | O-2-ethylhexyl |
| A-24 | H | CF₃ | N(CH₃)₂ |
| A-25 | CF₃ | H | N(CH₃)₂ |
| A-26 | H | CF₃ | NPh₂ |
| A-27 | CF₃ | H | NPh₂ |
| A-28 | H | CN | H |
| A-29 | CN | H | H |
| A-30 | H | CN | OCH₃ |
| A-31 | CN | H | OCH₂CH₃ |
| A-32 | H | CN | OCH₂CH₃ |
| A-33 | CN | H | O-n-butyl |
| A-34 | H | CN | O-n-butyl |
| A-35 | CN | H | O-iso-butyl |
| A-36 | H | CN | O-iso-butyl |
| A-37 | CN | H | O-2-butyl |
| A-38 | H | CN | O-2-butyl |
| A-39 | CN | H | O-2-ethylhexyl |
| A-40 | H | CN | O-2-ethylhexyl |
| A-41 | CN | H | N(CH₃)₂ |
| A-42 | H | CN | N(CH₃)₂ |
| A-43 | CN | H | NPh₂ |
| A-44 | H | CN | NPh₂ |

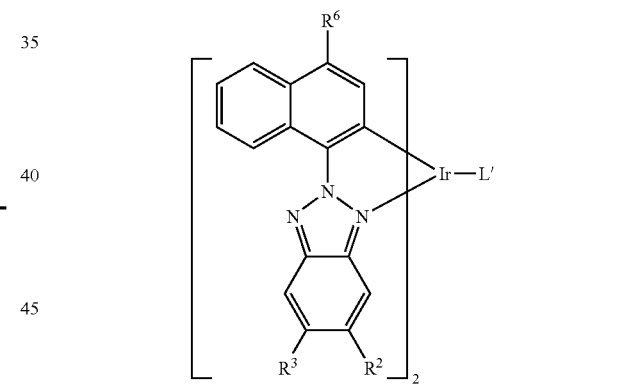

| Cpd. | L' | R² | R³ | R⁶ |
|---|---|---|---|---|
| B-1 | A¹⁾ | H | H | H |
| B-2 | A¹⁾ | H | H | OCH₃ |
| B-3 | A¹⁾ | H | H | OCH₂CH₃ |
| B-4 | A¹⁾ | H | H | O-n-butyl |
| B-5 | A¹⁾ | H | H | O-iso-butyl |
| B-6 | A¹⁾ | H | H | O-2-butyl |
| B-7 | A¹⁾ | H | H | O-2-ethylhexyl |
| B-8 | A¹⁾ | H | H | N(CH₃)₂ |
| B-9 | A¹⁾ | H | H | NPh₂ |
| B-10 | A¹⁾ | H | CF₃ | H |
| B-11 | A¹⁾ | CF₃ | H | H |
| B-12 | A¹⁾ | H | CF₃ | OCH₃ |
| B-13 | A¹⁾ | CF₃ | H | OCH₃ |
| B-14 | A¹⁾ | H | CF₃ | OCH₂CH₃ |
| B-15 | A¹⁾ | CF₃ | H | OCH₂CH₃ |
| B-16 | A¹⁾ | H | CF₃ | O-n-butyl |
| B-17 | A¹⁾ | CF₃ | H | O-n-butyl |
| B-18 | A¹⁾ | H | CF₃ | O-iso-butyl |
| B-19 | A¹⁾ | CF₃ | H | O-iso-butyl |
| B-20 | A¹⁾ | H | CF₃ | O-2-butyl |

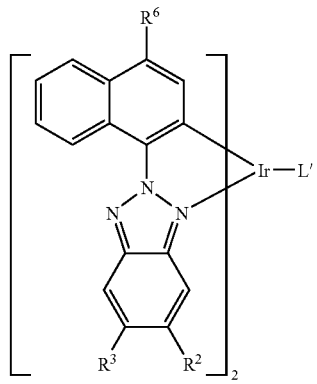

| Cpd. | L' | R² | R³ | R⁶ |
|---|---|---|---|---|
| B-21 | A¹⁾ | CF₃ | H | O-2-butyl |
| B-22 | A¹⁾ | H | CF₃ | O-2-ethylhexyl |
| B-23 | A¹⁾ | CF₃ | H | O-2-ethylhexyl |
| B-24 | A¹⁾ | H | CF₃ | N(CH₃)₂ |
| B-25 | A¹⁾ | CF₃ | H | N(CH₃)₂ |
| B-26 | A¹⁾ | H | CF₃ | NPh₂ |
| B-27 | A¹⁾ | CF₃ | H | NPh₂ |
| B-28 | A¹⁾ | H | CN | H |
| B-29 | A¹⁾ | CN | H | H |
| B-30 | A¹⁾ | CN | H | OCH₃ |
| B-31 | A¹⁾ | H | CN | OCH₃ |
| B-32 | A¹⁾ | CN | H | OCH₂CH₃ |
| B-33 | A¹⁾ | H | CN | OCH₂CH₃ |
| B-34 | A¹⁾ | CN | H | O-n-butyl |
| B-35 | A¹⁾ | H | CN | O-n-butyl |
| B-36 | A¹⁾ | CN | H | O-iso-butyl |
| B-37 | A¹⁾ | H | CN | O-iso-butyl |
| B-38 | A¹⁾ | CN | H | O-2-butyl |
| B-39 | A¹⁾ | H | CN | O-2-butyl |
| B-40 | A¹⁾ | CN | H | O-2-ethylhexyl |
| B-41 | A¹⁾ | H | CN | O-2-ethylhexyl |
| B-42 | A¹⁾ | CN | H | N(CH₃)₂ |
| B-43 | A¹⁾ | H | CN | N(CH₃)₂ |
| B-44 | A¹⁾ | CN | H | NPh₂ |
| B-45 | A¹⁾ | H | CN | NPh₂ |
| B-46 | B¹⁾ | H | H | H |
| B-47 | B¹⁾ | H | H | OCH₃ |
| B-48 | B¹⁾ | H | H | OCH₂CH₃ |
| B-49 | B¹⁾ | H | H | O-n-butyl |
| B-50 | B¹⁾ | H | H | O-iso-butyl |
| B-51 | B¹⁾ | H | H | O-2-butyl |
| B-52 | B¹⁾ | H | H | O-2-ethylhexyl |
| B-53 | B¹⁾ | H | H | N(CH₃)₂ |
| B-54 | B¹⁾ | H | H | NPh₂ |
| B-55 | B¹⁾ | H | CF₃ | H |
| B-56 | B¹⁾ | CF₃ | H | H |
| B-57 | B¹⁾ | H | CF₃ | OCH₃ |
| B-58 | B¹⁾ | CF₃ | H | OCH₃ |
| B-59 | B¹⁾ | H | CF₃ | OCH₂CH₃ |
| B-60 | B¹⁾ | CF₃ | H | OCH₂CH₃ |
| B-61 | B¹⁾ | H | CF₃ | O-n-butyl |
| B-62 | B¹⁾ | CF₃ | H | O-n-butyl |
| B-63 | B¹⁾ | H | CF₃ | O-iso-butyl |
| B-64 | B¹⁾ | CF₃ | H | O-iso-butyl |
| B-65 | B¹⁾ | H | CF₃ | O-2-butyl |
| B-66 | B¹⁾ | CF₃ | H | O-2-butyl |
| B-67 | B¹⁾ | H | CF₃ | O-2-ethylhexyl |
| B-68 | B¹⁾ | CF₃ | H | O-2-ethylhexyl |
| B-69 | B¹⁾ | H | CF₃ | N(CH₃)₂ |
| B-70 | B¹⁾ | CF₃ | H | N(CH₃)₂ |
| B-71 | B¹⁾ | H | CF₃ | NPh₂ |
| B-72 | B¹⁾ | CF₃ | H | NPh₂ |
| B-73 | B¹⁾ | H | CN | H |
| B-74 | B¹⁾ | CN | H | H |
| B-75 | B¹⁾ | CN | H | OCH₃ |
| B-76 | B¹⁾ | H | CN | OCH₃ |
| B-77 | B¹⁾ | CN | H | OCH₂CH₃ |
| B-78 | B¹⁾ | H | CN | OCH₂CH₃ |
| B-79 | B¹⁾ | CN | H | O-n-butyl |

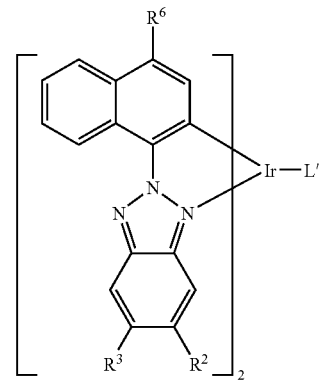

| Cpd. | L' | R² | R³ | R⁶ |
|---|---|---|---|---|
| B-80 | B¹⁾ | H | CN | O-n-butyl |
| B-81 | B¹⁾ | CN | H | O-iso-butyl |
| B-82 | B¹⁾ | H | CN | O-iso-butyl |
| B-83 | B¹⁾ | CN | H | O-2-butyl |
| B-84 | B¹⁾ | H | CN | O-2-butyl |
| B-85 | B¹⁾ | CN | H | O-2-ethylhexyl |
| B-86 | B¹⁾ | H | CN | O-2-ethylhexyl |
| B-87 | B¹⁾ | CN | H | N(CH₃)₂ |
| B-88 | B¹⁾ | H | CN | N(CH₃)₂ |
| B-89 | B¹⁾ | CN | H | NPh₂ |
| B-99 | B¹⁾ | H | CN | NPh₂ |
| B-100 | C¹⁾ | H | H | H |
| B-101 | C¹⁾ | H | H | OCH₃ |
| B-102 | C¹⁾ | H | H | OCH₂CH₃ |
| B-103 | C¹⁾ | H | H | O-n-butyl |
| B-104 | C¹⁾ | H | H | O-iso-butyl |
| B-105 | C¹⁾ | H | H | O-2-butyl |
| B-106 | C¹⁾ | H | H | O-2-ethylhexyl |
| B-107 | C¹⁾ | H | H | N(CH₃)₂ |
| B-108 | C¹⁾ | H | H | NPh₂ |
| B-109 | C¹⁾ | H | CF₃ | H |
| B-110 | C¹⁾ | CF₃ | H | H |
| B-111 | C¹⁾ | H | CF₃ | OCH₃ |
| B-112 | C¹⁾ | CF₃ | H | OCH₃ |
| B-113 | C¹⁾ | H | CF₃ | OCH₂CH₃ |
| B-114 | C¹⁾ | CF₃ | H | OCH₂CH₃ |
| B-115 | C¹⁾ | H | CF₃ | O-n-butyl |
| B-116 | C¹⁾ | CF₃ | H | O-n-butyl |
| B-117 | C¹⁾ | H | CF₃ | O-iso-butyl |
| B-118 | C¹⁾ | CF₃ | H | O-iso-butyl |
| B-119 | C¹⁾ | H | CF₃ | O-2-butyl |
| B-120 | C¹⁾ | CF₃ | H | O-2-butyl |
| B-121 | C¹⁾ | H | CF₃ | O-2-ethylhexyl |
| B-122 | C¹⁾ | CF₃ | H | O-2-ethylhexyl |
| B-123 | C¹⁾ | H | CF₃ | N(CH₃)₂ |
| B-124 | C¹⁾ | CF₃ | H | N(CH₃)₂ |
| B-125 | C¹⁾ | H | CF₃ | NPh₂ |
| B-126 | C¹⁾ | CF₃ | H | NPh₂ |
| B-127 | C¹⁾ | H | CN | H |
| B-128 | C¹⁾ | CN | H | H |
| B-129 | C¹⁾ | CN | H | OCH₃ |
| B-130 | C¹⁾ | H | CN | OCH₃ |
| B-131 | C¹⁾ | CN | H | OCH₂CH₃ |
| B-132 | C¹⁾ | H | CN | OCH₂CH₃ |
| B-133 | C¹⁾ | CN | H | O-n-butyl |
| B-134 | C¹⁾ | H | CN | O-n-butyl |
| B-135 | C¹⁾ | CN | H | O-iso-butyl |
| B-136 | C¹⁾ | H | CN | O-iso-butyl |
| B-137 | C¹⁾ | CN | H | O-2-butyl |
| B-138 | C¹⁾ | H | CN | O-2-butyl |
| B-139 | C¹⁾ | CN | H | O-2-ethylhexyl |
| B-140 | C¹⁾ | H | CN | O-2-ethylhexyl |
| B-141 | C¹⁾ | CN | H | N(CH₃)₂ |
| B-142 | C¹⁾ | H | CN | N(CH₃)₂ |
| B-143 | C¹⁾ | CN | H | NPh₂ |
| B-144 | C¹⁾ | H | CN | NPh₂ |
| B-145 | D¹⁾ | H | H | H |
| B-146 | D¹⁾ | H | H | OCH₃ |
| B-147 | D¹⁾ | H | H | OCH₂CH₃ |

-continued

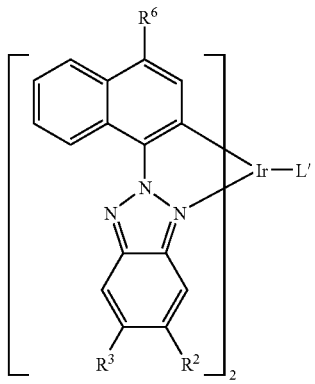

| Cpd. | L' | R² | R³ | R⁶ |
|---|---|---|---|---|
| B-148 | D¹⁾ | H | H | O-n-butyl |
| B-149 | D¹⁾ | H | H | O-iso-butyl |
| B-150 | D¹⁾ | H | H | O-2-butyl |
| B-151 | D¹⁾ | H | H | O-2-ethylhexyl |
| B-152 | D¹⁾ | H | H | N(CH₃)₂ |
| B-153 | D¹⁾ | H | H | NPh₂ |
| B-154 | D¹⁾ | H | CF₃ | H |
| B-155 | D¹⁾ | CF₃ | H | H |
| B-156 | D¹⁾ | H | CF₃ | OCH₃ |
| B-157 | D¹⁾ | CF₃ | H | OCH₃ |
| B-158 | D¹⁾ | H | CF₃ | OCH₂CH₃ |
| B-159 | D¹⁾ | CF₃ | H | OCH₂CH₃ |
| B-160 | D¹⁾ | H | CF₃ | O-n-butyl |
| B-161 | D¹⁾ | CF₃ | H | O-n-butyl |
| B-162 | D¹⁾ | H | CF₃ | O-iso-butyl |
| B-163 | D¹⁾ | CF₃ | H | O-iso-butyl |
| B-164 | D¹⁾ | H | CF₃ | O-2-butyl |
| B-165 | D¹⁾ | CF₃ | H | O-2-butyl |
| B-166 | D¹⁾ | H | CF₃ | O-2-ethylhexyl |
| B-167 | D¹⁾ | CF₃ | H | O-2-ethylhexyl |
| B-168 | D¹⁾ | H | CF₃ | N(CH₃)₂ |
| B-169 | D¹⁾ | CF₃ | H | N(CH₃)₂ |
| B-170 | D¹⁾ | H | CF₃ | NPh₂ |
| B-171 | D¹⁾ | CF₃ | H | NPh₂ |
| B-172 | D¹⁾ | H | CN | H |
| B-173 | D¹⁾ | CN | H | H |
| B-174 | D¹⁾ | CN | H | OCH₃ |
| B-175 | D¹⁾ | H | CN | OCH₃ |
| B-176 | D¹⁾ | CN | H | OCH₂CH₃ |
| B-177 | D¹⁾ | H | CN | OCH₂CH₃ |
| B-178 | D¹⁾ | CN | H | O-n-butyl |
| B-179 | D¹⁾ | H | CN | O-n-butyl |
| B-180 | D¹⁾ | CN | H | O-iso-butyl |
| B-181 | D¹⁾ | H | CN | O-iso-butyl |
| B-182 | D¹⁾ | CN | H | O-2-butyl |
| B-183 | D¹⁾ | H | CN | O-2-butyl |
| B-184 | D¹⁾ | CN | H | O-2-ethylhexyl |
| B-185 | D¹⁾ | H | CN | O-2-ethylhexyl |
| B-186 | D¹⁾ | CN | H | N(CH₃)₂ |
| B-187 | D¹⁾ | H | CN | N(CH₃)₂ |
| B-188 | D¹⁾ | CN | H | NPh₂ |
| B-189 | D¹⁾ | H | CN | NPh₂ |
| B-190 | E¹⁾ | H | H | H |
| B-191 | E¹⁾ | H | H | OCH₃ |
| B-192 | E¹⁾ | H | H | OCH₂CH₃ |
| B-193 | E¹⁾ | H | H | O-n-butyl |
| B-194 | E¹⁾ | H | H | O-iso-butyl |
| B-195 | E¹⁾ | H | H | O-2-butyl |
| B-196 | E¹⁾ | H | H | O-2-ethylhexyl |
| B-197 | E¹⁾ | H | H | N(CH₃)₂ |
| B-198 | E¹⁾ | H | H | NPh₂ |
| B-199 | E¹⁾ | H | CF₃ | H |
| B-200 | E¹⁾ | CF₃ | H | H |
| B-201 | E¹⁾ | H | CF₃ | OCH₃ |
| B-202 | E¹⁾ | CF₃ | H | OCH₃ |
| B-203 | E¹⁾ | H | CF₃ | OCH₂CH₃ |
| B-204 | E¹⁾ | CF₃ | H | OCH₂CH₃ |
| B-205 | E¹⁾ | H | CF₃ | O-n-butyl |
| B-206 | E¹⁾ | CF₃ | H | O-n-butyl |

-continued

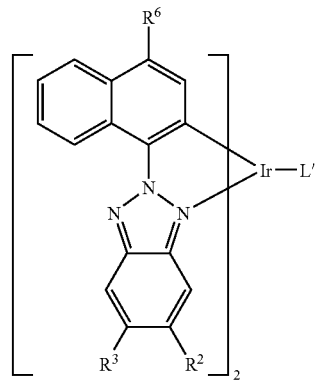

| Cpd. | L' | R² | R³ | R⁶ |
|---|---|---|---|---|
| B-207 | E¹⁾ | H | CF₃ | O-iso-butyl |
| B-208 | E¹⁾ | CF₃ | H | O-iso-butyl |
| B-209 | E¹⁾ | H | CF₃ | O-2-butyl |
| B-210 | E¹⁾ | CF₃ | H | O-2-butyl |
| B-211 | E¹⁾ | H | CF₃ | O-2-ethylhexyl |
| B-212 | E¹⁾ | CF₃ | H | O-2-ethylhexyl |
| B-213 | E¹⁾ | H | CF₃ | N(CH₃)₂ |
| B-214 | E¹⁾ | CF₃ | H | N(CH₃)₂ |
| B-215 | E¹⁾ | H | CF₃ | NPh₂ |
| B-216 | E¹⁾ | CF₃ | H | NPh₂ |
| B-217 | E¹⁾ | H | CN | H |
| B-218 | E¹⁾ | CN | H | H |
| B-219 | E¹⁾ | CN | H | OCH₃ |
| B-220 | E¹⁾ | H | CN | OCH₃ |
| B-221 | E¹⁾ | CN | H | OCH₂CH₃ |
| B-222 | E¹⁾ | H | CN | OCH₂CH₃ |
| B-223 | E¹⁾ | CN | H | O-n-butyl |
| B-224 | E¹⁾ | H | CN | O-n-butyl |
| B-225 | E¹⁾ | CN | H | O-iso-butyl |
| B-226 | E¹⁾ | H | CN | O-iso-butyl |
| B-227 | E¹⁾ | CN | H | O-2-butyl |
| B-228 | E¹⁾ | H | CN | O-2-butyl |
| B-229 | E¹⁾ | CN | H | O-2-ethylhexyl |
| B-230 | E¹⁾ | H | CN | O-2-ethylhexyl |
| B-231 | E¹⁾ | CN | H | N(CH₃)₂ |
| B-232 | E¹⁾ | H | CN | N(CH₃)₂ |
| B-233 | E¹⁾ | CN | H | NPh₂ |
| B-234 | E¹⁾ | H | CN | NPh₂ |

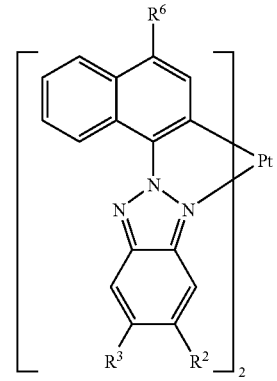

| Cpd. | R² | R³ | R⁶ |
|---|---|---|---|
| C-1 | H | H | H |
| C-2 | H | H | OCH₃ |
| C-3 | H | H | OCH₂CH₃ |
| C-4 | H | H | O-n-butyl |
| C-5 | H | H | O-iso-butyl |
| C-6 | H | H | O-2-butyl |

-continued

| Cpd. | | | |
|---|---|---|---|
| C-7 | H | H | O-2-ethylhexyl |
| C-8 | H | H | N(CH₃)₂ |
| C-9 | H | H | NPh₂ |
| C-10 | H | CF₃ | H |
| C-11 | CF₃ | H | H |
| C-12 | H | CF₃ | OCH₃ |
| C-13 | CF₃ | H | OCH₃ |
| C-14 | H | CF₃ | OCH₂CH₃ |
| C-15 | CF₃ | H | OCH₂CH₃ |
| C-16 | H | CF₃ | O-n-butyl |
| C-17 | CF₃ | H | O-n-butyl |
| C-18 | H | CF₃ | O-iso-butyl |
| C-19 | CF₃ | H | O-iso-butyl |
| C-20 | H | CF₃ | O-2-butyl |
| C-21 | CF₃ | H | O-2-butyl |
| C-22 | H | CF₃ | O-2-ethylhexyl |
| C-23 | CF₃ | H | O-2-ethylhexyl |
| C-24 | H | CF₃ | N(CH₃)₂ |
| C-25 | CF₃ | H | N(CH₃)₂ |
| C-26 | H | CF₃ | NPh₂ |
| C-27 | CF₃ | H | NPh₂ |
| C-28 | H | CN | H |
| C-29 | CN | H | H |
| C-30 | H | CN | OCH₃ |
| C-31 | CN | H | OCH₂CH₃ |
| C-32 | H | CN | OCH₂CH₃ |
| C-33 | CN | H | O-n-butyl |
| C-34 | H | CN | O-n-butyl |
| C-35 | CN | H | O-iso-butyl |
| C-36 | H | CN | O-iso-butyl |
| C-37 | CN | H | O-2-butyl |
| C-38 | H | CN | O-2-butyl |
| C-39 | CN | H | O-2-ethylhexyl |
| C-40 | H | CN | O-2-ethylhexyl |
| C-41 | CN | H | N(CH₃)₂ |
| C-42 | H | CN | N(CH₃)₂ |
| C-43 | CN | H | NPh₂ |
| C-44 | H | CN | NPh₂ |

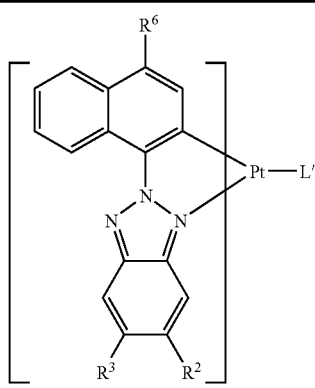

| Cpd. | L' | R² | R³ | R⁶ |
|---|---|---|---|---|
| D-1 | A¹⁾ | H | H | H |
| D-2 | A¹⁾ | H | H | OCH₃ |
| D-3 | A¹⁾ | H | H | OCH₂CH₃ |
| D-4 | A¹⁾ | H | H | O-n-butyl |
| D-5 | A¹⁾ | H | H | O-iso-butyl |
| D-6 | A¹⁾ | H | H | O-2-butyl |
| D-7 | A¹⁾ | H | H | O-2-ethylhexyl |
| D-8 | A¹⁾ | H | H | N(CH₃)₂ |
| D-9 | A¹⁾ | H | H | NPh₂ |
| D-10 | A¹⁾ | H | CF₃ | H |
| D-11 | A¹⁾ | CF₃ | H | H |
| D-12 | A¹⁾ | H | CF₃ | OCH₃ |
| D-13 | A¹⁾ | CF₃ | H | OCH₃ |
| D-14 | A¹⁾ | H | CF₃ | OCH₂CH₃ |
| D-15 | A¹⁾ | CF₃ | H | OCH₂CH₃ |
| D-16 | A¹⁾ | H | CF₃ | O-n-butyl |

-continued

| Cpd. | L' | R² | R³ | R⁶ |
|---|---|---|---|---|
| D-17 | A¹⁾ | CF₃ | H | O-n-butyl |
| D-18 | A¹⁾ | H | CF₃ | O-iso-butyl |
| D-19 | A¹⁾ | CF₃ | H | O-iso-butyl |
| D-20 | A¹⁾ | H | CF₃ | O-2-butyl |
| D-21 | A¹⁾ | CF₃ | H | O-2-butyl |
| D-22 | A¹⁾ | H | CF₃ | O-2-ethylhexyl |
| D-23 | A¹⁾ | CF₃ | H | O-2-ethylhexyl |
| D-24 | A¹⁾ | H | CF₃ | N(CH₃)₂ |
| D-25 | A¹⁾ | CF₃ | H | N(CH₃)₂ |
| D-26 | A¹⁾ | H | CF₃ | NPh₂ |
| D-27 | A¹⁾ | CF₃ | H | NPh₂ |
| D-28 | A¹⁾ | H | CN | H |
| D-29 | A¹⁾ | CN | H | H |
| D-30 | A¹⁾ | CN | H | OCH₃ |
| D-31 | A¹⁾ | H | CN | OCH₃ |
| D-32 | A¹⁾ | CN | H | OCH₂CH₃ |
| D-33 | A¹⁾ | H | CN | OCH₂CH₃ |
| D-34 | A¹⁾ | CN | H | O-n-butyl |
| D-35 | A¹⁾ | H | CN | O-n-butyl |
| D-36 | A¹⁾ | CN | H | O-iso-butyl |
| D-37 | A¹⁾ | H | CN | O-iso-butyl |
| D-38 | A¹⁾ | CN | H | O-2-butyl |
| D-39 | A¹⁾ | H | CN | O-2-butyl |
| D-40 | A¹⁾ | CN | H | O-2-ethylhexyl |
| D-41 | A¹⁾ | H | CN | O-2-ethylhexyl |
| D-42 | A¹⁾ | CN | H | N(CH₃)₂ |
| D-43 | A¹⁾ | H | CN | N(CH₃)₂ |
| D-44 | A¹⁾ | CN | H | NPh₂ |
| D-45 | A¹⁾ | H | CN | NPh₂ |
| D-46 | B¹⁾ | H | H | H |
| D-47 | B¹⁾ | H | H | OCH₃ |
| D-48 | B¹⁾ | H | H | OCH₂CH₃ |
| D-49 | B¹⁾ | H | H | O-n-butyl |
| D-50 | B¹⁾ | H | H | O-iso-butyl |
| D-51 | B¹⁾ | H | H | O-2-butyl |
| D-52 | B¹⁾ | H | H | O-2-ethylhexyl |
| D-53 | B¹⁾ | H | H | N(CH₃)₂ |
| D-54 | B¹⁾ | H | H | NPh₂ |
| D-55 | B¹⁾ | H | CF₃ | H |
| D-56 | B¹⁾ | CF₃ | H | H |
| D-57 | B¹⁾ | H | CF₃ | OCH₃ |
| D-58 | B¹⁾ | CF₃ | H | OCH₃ |
| D-59 | B¹⁾ | H | CF₃ | OCH₂CH₃ |
| D-60 | B¹⁾ | CF₃ | H | OCH₂CH₃ |
| D-61 | B¹⁾ | H | CF₃ | O-n-butyl |
| D-62 | B¹⁾ | CF₃ | H | O-n-butyl |
| D-63 | B¹⁾ | H | CF₃ | O-iso-butyl |
| D-64 | B¹⁾ | CF₃ | H | O-iso-butyl |
| D-65 | B¹⁾ | H | CF₃ | O-2-butyl |
| D-66 | B¹⁾ | CF₃ | H | O-2-butyl |
| D-67 | B¹⁾ | H | CF₃ | O-2-ethylhexyl |
| D-68 | B¹⁾ | CF₃ | H | O-2-ethylhexyl |
| D-69 | B¹⁾ | H | CF₃ | N(CH₃)₂ |
| D-70 | B¹⁾ | CF₃ | H | N(CH₃)₂ |
| D-71 | B¹⁾ | H | CF₃ | NPh₂ |
| D-72 | B¹⁾ | CF₃ | H | NPh₂ |
| D-73 | B¹⁾ | H | CN | H |
| D-74 | B¹⁾ | CN | H | H |
| D-75 | B¹⁾ | CN | H | OCH₃ |

-continued

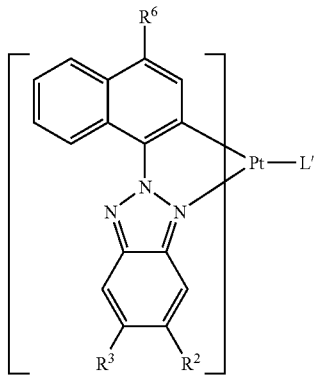

| Cpd. | L' | R² | R³ | R⁶ |
|---|---|---|---|---|
| D-76 | B[1] | H | CN | OCH₃ |
| D-77 | B[1] | CN | H | OCH₂CH₃ |
| D-78 | B[1] | H | CN | OCH₂CH₃ |
| D-79 | B[1] | CN | H | O-n-butyl |
| D-80 | B[1] | H | CN | O-n-butyl |
| D-81 | B[1] | CN | H | O-iso-butyl |
| D-82 | B[1] | H | CN | O-iso-butyl |
| D-83 | B[1] | CN | H | O-2-butyl |
| D-84 | B[1] | H | CN | O-2-butyl |
| D-85 | B[1] | CN | H | O-2-ethylhexyl |
| D-86 | B[1] | H | CN | O-2-ethylhexyl |
| D-87 | B[1] | CN | H | N(CH₃)₂ |
| D-88 | B[1] | H | CN | N(CH₃)₂ |
| D-89 | B[1] | CN | H | NPh₂ |
| D-99 | B[1] | H | CN | NPh₂ |
| D-100 | C[1] | H | H | H |
| D-101 | C[1] | H | H | OCH₃ |
| D-102 | C[1] | H | H | OCH₂CH₃ |
| D-103 | C[1] | H | H | O-n-butyl |
| D-104 | C[1] | H | H | O-iso-butyl |
| D-105 | C[1] | H | H | O-2-butyl |
| D-106 | C[1] | H | H | O-2-ethylhexyl |
| D-107 | C[1] | H | H | N(CH₃)₂ |
| D-108 | C[1] | H | H | NPh₂ |
| D-109 | C[1] | H | CF₃ | H |
| D-110 | C[1] | CF₃ | H | H |
| D-111 | C[1] | H | CF₃ | OCH₃ |
| D-112 | C[1] | CF₃ | H | OCH₃ |
| D-113 | C[1] | H | CF₃ | OCH₂CH₃ |
| D-114 | C[1] | CF₃ | H | OCH₂CH₃ |
| D-115 | C[1] | H | CF₃ | O-n-butyl |
| D-116 | C[1] | CF₃ | H | O-n-butyl |
| D-117 | C[1] | H | CF₃ | O-iso-butyl |
| D-118 | C[1] | CF₃ | H | O-iso-butyl |
| D-119 | C[1] | H | CF₃ | O-2-butyl |
| D-120 | C[1] | CF₃ | H | O-2-butyl |
| D-121 | C[1] | H | CF₃ | O-2-ethylhexyl |
| D-122 | C[1] | CF₃ | H | O-2-ethylhexyl |
| D-123 | C[1] | H | CF₃ | N(CH₃)₂ |
| D-124 | C[1] | CF₃ | H | N(CH₃)₂ |
| D-125 | C[1] | H | CF₃ | NPh₂ |
| D-126 | C[1] | CF₃ | H | NPh₂ |
| D-127 | C[1] | H | CN | H |
| D-128 | C[1] | CN | H | H |
| D-129 | C[1] | CN | H | OCH₃ |
| D-130 | C[1] | H | CN | OCH₃ |
| D-131 | C[1] | CN | H | OCH₂CH₃ |
| D-132 | C[1] | H | CN | OCH₂CH₃ |
| D-133 | C[1] | CN | H | O-n-butyl |
| D-134 | C[1] | H | CN | O-n-butyl |
| D-135 | C[1] | CN | H | O-iso-butyl |
| D-136 | C[1] | H | CN | O-iso-butyl |
| D-137 | C[1] | CN | H | O-2-butyl |
| D-138 | C[1] | H | CN | O-2-butyl |
| D-139 | C[1] | CN | H | O-2-ethylhexyl |
| D-140 | C[1] | H | CN | O-2-ethylhexyl |
| D-141 | C[1] | CN | H | N(CH₃)₂ |
| D-142 | C[1] | H | CN | N(CH₃)₂ |
| D-143 | C[1] | CN | H | NPh₂ |

-continued

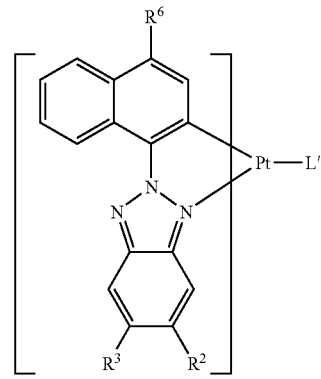

| Cpd. | L' | R² | R³ | R⁶ |
|---|---|---|---|---|
| D-144 | C[1] | H | CN | NPh₂ |
| D-145 | D[1] | H | H | H |
| D-146 | D[1] | H | H | OCH₃ |
| D-147 | D[1] | H | H | OCH₂CH₃ |
| D-148 | D[1] | H | H | O-n-butyl |
| D-149 | D[1] | H | H | O-iso-butyl |
| D-150 | D[1] | H | H | O-2-butyl |
| D-151 | D[1] | H | H | O-2-ethylhexyl |
| D-152 | D[1] | H | H | N(CH₃)₂ |
| D-153 | D[1] | H | H | NPh₂ |
| D-154 | D[1] | H | CF₃ | H |
| D-155 | D[1] | CF₃ | H | H |
| D-156 | D[1] | H | CF₃ | OCH₃ |
| D-157 | D[1] | CF₃ | H | OCH₃ |
| D-158 | D[1] | H | CF₃ | OCH₂CH₃ |
| D-159 | D[1] | CF₃ | H | OCH₂CH₃ |
| D-160 | D[1] | H | CF₃ | O-n-butyl |
| D-161 | D[1] | CF₃ | H | O-n-butyl |
| D-162 | D[1] | H | CF₃ | O-iso-butyl |
| D-163 | D[1] | CF₃ | H | O-iso-butyl |
| D-164 | D[1] | H | CF₃ | O-2-butyl |
| D-165 | D[1] | CF₃ | H | O-2-butyl |
| D-166 | D[1] | H | CF₃ | O-2-ethylhexyl |
| D-167 | D[1] | CF₃ | H | O-2-ethylhexyl |
| D-168 | D[1] | H | CF₃ | N(CH₃)₂ |
| D-169 | D[1] | CF₃ | H | N(CH₃)₂ |
| D-170 | D[1] | H | CF₃ | NPh₂ |
| D-171 | D[1] | CF₃ | H | NPh₂ |
| D-172 | D[1] | H | CN | H |
| D-173 | D[1] | CN | H | H |
| D-174 | D[1] | CN | H | OCH₃ |
| D-175 | D[1] | H | CN | OCH₃ |
| D-176 | D[1] | CN | H | OCH₂CH₃ |
| D-177 | D[1] | H | CN | OCH₂CH₃ |
| D-178 | D[1] | CN | H | O-n-butyl |
| D-179 | D[1] | H | CN | O-n-butyl |
| D-180 | D[1] | CN | H | O-iso-butyl |
| D-181 | D[1] | H | CN | O-iso-butyl |
| D-182 | D[1] | CN | H | O-2-butyl |
| D-183 | D[1] | H | CN | O-2-butyl |
| D-184 | D[1] | CN | H | O-2-ethylhexyl |
| D-185 | D[1] | H | CN | O-2-ethylhexyl |
| D-186 | D[1] | CN | H | N(CH₃)₂ |
| D-187 | D[1] | H | CN | N(CH₃)₂ |
| D-188 | D[1] | CN | H | NPh₂ |
| D-189 | D[1] | H | CN | NPh₂ |
| D-190 | F[1] | H | H | H |
| D-191 | F[1] | H | H | OCH₃ |
| D-192 | F[1] | H | H | OCH₂CH₃ |
| D-193 | F[1] | H | H | O-n-butyl |
| D-194 | F[1] | H | H | O-iso-butyl |
| D-195 | F[1] | H | H | O-2-butyl |
| D-196 | F[1] | H | H | O-2-ethylhexyl |
| D-197 | F[1] | H | H | N(CH₃)₂ |
| D-198 | F[1] | H | H | NPh₂ |
| D-199 | F[1] | H | CF₃ | H |
| D-200 | F[1] | CF₃ | H | H |
| D-201 | F[1] | H | CF₃ | OCH₃ |
| D-202 | F[1] | CF₃ | H | OCH₃ |

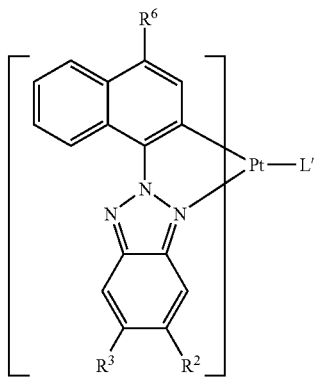

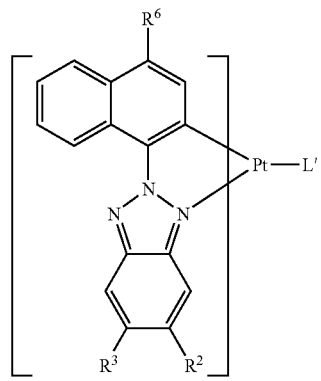

| Cpd. | L' | R² | R³ | R⁶ |
|---|---|---|---|---|
| D-203 | F¹⁾ | H | CF₃ | OCH₂CH₃ |
| D-204 | F¹⁾ | CF₃ | H | OCH₂CH₃ |
| D-205 | F¹⁾ | H | CF₃ | O-n-butyl |
| D-206 | F¹⁾ | CF₃ | H | O-n-butyl |
| D-207 | F¹⁾ | H | CF₃ | O-iso-butyl |
| D-208 | F¹⁾ | CF₃ | H | O-iso-butyl |
| D-209 | F¹⁾ | H | CF₃ | O-2-butyl |
| D-210 | F¹⁾ | CF₃ | H | O-2-butyl |
| D-211 | F¹⁾ | H | CF₃ | O-2-ethylhexyl |
| D-212 | F¹⁾ | CF₃ | H | O-2-ethylhexyl |
| D-213 | F¹⁾ | H | CF₃ | N(CH₃)₂ |
| D-214 | F¹⁾ | CF₃ | H | N(CH₃)₂ |
| D-215 | F¹⁾ | H | CF₃ | NPh₂ |
| D-216 | F¹⁾ | CF₃ | H | NPh₂ |
| D-217 | F¹⁾ | H | CN | H |
| D-218 | F¹⁾ | CN | H | H |
| D-219 | F¹⁾ | CN | H | OCH₃ |
| D-220 | F¹⁾ | H | CN | OCH₃ |
| D-221 | F¹⁾ | CN | H | OCH₂CH₃ |
| D-222 | F¹⁾ | H | CN | OCH₂CH₃ |
| D-223 | F¹⁾ | CN | H | O-n-butyl |
| D-224 | F¹⁾ | H | CN | O-n-butyl |
| D-225 | F¹⁾ | CN | H | O-iso-butyl |
| D-226 | F¹⁾ | H | CN | O-iso-butyl |
| D-227 | F¹⁾ | CN | H | O-2-butyl |
| D-228 | F¹⁾ | H | CN | O-2-butyl |
| D-229 | F¹⁾ | CN | H | O-2-ethylhexyl |
| D-230 | F¹⁾ | H | CN | O-2-ethylhexyl |
| D-231 | F¹⁾ | CN | H | N(CH₃)₂ |
| D-232 | F¹⁾ | H | CN | N(CH₃)₂ |
| D-233 | F¹⁾ | CN | H | NPh₂ |
| D-234 | F¹⁾ | H | CN | NPh₂ |
| D-235 | E¹⁾ | H | H | H |
| D-236 | E¹⁾ | H | H | OCH₃ |
| D-237 | E¹⁾ | H | H | OCH₂CH₃ |
| D-238 | E¹⁾ | H | H | O-n-butyl |
| D-239 | E¹⁾ | H | H | O-iso-butyl |
| D-240 | E¹⁾ | H | H | O-2-butyl |
| D-241 | E¹⁾ | H | H | O-2-ethylhexyl |
| D-242 | E¹⁾ | H | H | N(CH₃)₂ |
| D-243 | E¹⁾ | H | H | NPh₂ |
| D-244 | E¹⁾ | H | CF₃ | H |
| D-245 | E¹⁾ | CF₃ | H | H |
| D-246 | E¹⁾ | H | CF₃ | OCH₃ |
| D-247 | E¹⁾ | CF₃ | H | OCH₃ |
| D-248 | E¹⁾ | H | CF₃ | OCH₂CH₃ |
| D-249 | E¹⁾ | CF₃ | H | OCH₂CH₃ |
| D-250 | E¹⁾ | H | CF₃ | O-n-butyl |
| D-251 | E¹⁾ | CF₃ | H | O-n-butyl |
| D-252 | E¹⁾ | H | CF₃ | O-iso-butyl |
| D-253 | E¹⁾ | CF₃ | H | O-iso-butyl |
| D-254 | E¹⁾ | H | CF₃ | O-2-butyl |
| D-255 | E¹⁾ | CF₃ | H | O-2-butyl |
| D-256 | E¹⁾ | H | CF₃ | O-2-ethylhexyl |
| D-257 | E¹⁾ | CF₃ | H | O-2-ethylhexyl |
| D-258 | E¹⁾ | H | CF₃ | N(CH₃)₂ |
| D-259 | E¹⁾ | CF₃ | H | N(CH₃)₂ |
| D-260 | E¹⁾ | H | CF₃ | NPh₂ |
| D-261 | E¹⁾ | CF₃ | H | NPh₂ |
| D-262 | E¹⁾ | H | CN | H |
| D-263 | E¹⁾ | CN | H | H |
| D-264 | E¹⁾ | CN | H | OCH₃ |
| D-265 | E¹⁾ | H | CN | OCH₃ |
| D-266 | E¹⁾ | CN | H | OCH₂CH₃ |
| D-267 | E¹⁾ | H | CN | OCH₂CH₃ |
| D-268 | E¹⁾ | CN | H | O-n-butyl |
| D-269 | E¹⁾ | H | CN | O-n-butyl |
| D-270 | E¹⁾ | CN | H | O-iso-butyl |
| D-271 | E¹⁾ | H | CN | O-iso-butyl |
| D-272 | E¹⁾ | CN | H | O-2-butyl |
| D-273 | E¹⁾ | H | CN | O-2-butyl |
| D-274 | E¹⁾ | CN | H | O-2-ethylhexyl |
| D-275 | E¹⁾ | H | CN | O-2-ethylhexyl |
| D-276 | E¹⁾ | CN | H | N(CH₃)₂ |
| D-277 | E¹⁾ | H | CN | N(CH₃)₂ |
| D-278 | E¹⁾ | CN | H | NPh₂ |
| D-279 | E¹⁾ | H | CN | NPh₂ |

¹⁾ A = [acetylacetonate structure], B = [picolinate methyl ester structure], C = [salicylaldehyde N-methylimine structure], D = [8-methoxyquinoline structure], E = [di-tert-butyl acetylacetonate structure], F = [2-(2'-pyridyl)phenyl structure].

Blocking Layers

In addition to suitable hosts, an OLED device employing a phosphorescent material often requires at least one exciton or hole blocking layers to help confine the excitons or electron-hole recombination centers to the light-emitting layer comprising the host and phosphorescent material, or to reduce the number of charge carriers (electrons or holes). In one embodiment, such a blocking layer would be placed between the electron-transporting layer and the light-emitting layer. In this case, the ionization potential of the blocking layer should be such that there is an energy barrier for hole migration from the host into the electron-transporting layer, while the electron affinity should be such that electrons pass more readily from the electron-transporting layer into the light-emitting layer comprising host and phosphorescent material. It is further desired, but not absolutely required, that the triplet energy of the blocking material be greater than that of the phosphorescent material. Suitable hole-blocking materials are described in WO00/70655 and WO01/93642. Examples of useful materials are (1,3,5-tris(1-phenyl-1H-benzimidazol-2-yl)benzene) (TPBI), bathocuproine (BCP) and bis(2-methyl-8-quinolinolato)(4-phenylphenolato)aluminum(III) (BAlq). Metal complexes other than Balq are also known to block holes and excitons as described in US20030068528. US20030175553 describes the use of fac-tris(1-phenylpyrazolato-N,C2)iridium(III) (Irppz) in an electron/exciton blocking layer.

Embodiments of the invention can provide advantageous features such as operating efficiency, higher luminance, color hue, low drive voltage, and improved operating stability. Embodiments of the organometallic compounds useful in the invention can provide a wide range of hues including those useful in the emission of white light (directly or through filters to provide multicolor displays).

General Device Architecture

The compounds of the present invention can be employed in many OLED device configurations using small molecule materials, oligomeric materials, polymeric materials, or combinations thereof. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

There are numerous configurations of the organic layers. The essential requirements of an OLED are an anode, a cathode, and an organic light-emitting layer located between the anode and cathode. Additional layers may be employed as more fully described hereafter.

A typical structure, especially useful for of a small molecule device, is comprised of a substrate, an anode, a hole-injecting layer, a hole-transporting layer, a light-emitting layer, a hole- or exciton-blocking layer, an electron-transporting layer, and a cathode. These layers are described in detail below. Note that the substrate may alternatively be located adjacent to the cathode, or the substrate may actually constitute the anode or cathode. The organic layers between the anode and cathode are conveniently referred to as the organic EL element. Also, the total combined thickness of the organic layers is desirably less than 500 nm.

Substrate

The substrate can either be light transmissive or opaque, depending on the intended direction of light emission. The light transmissive property is desirable for viewing the EL emission through the substrate. Transparent glass or plastic is commonly employed in such cases. The substrate can be a complex structure comprising multiple layers of materials. This is typically the case for active matrix substrates wherein TFTs are provided below the OLED layers. It is still necessary that the substrate, at least in the emissive pixilated areas, be comprised of largely transparent materials such as glass or polymers. For applications where the EL emission is viewed through the top electrode, the transmissive characteristic of the bottom support is immaterial, and therefore can be light transmissive, light absorbing or light reflective. Substrates for use in this case include, but are not limited to, glass, plastic, semiconductor materials, silicon, ceramics, and circuit board materials. Again, the substrate can be a complex structure comprising multiple layers of materials such as found in active matrix TFT designs. It is necessary to provide in these device configurations a light-transparent top electrode.

Anode

When the desired electroluminescent light emission (EL) is viewed through the anode, the anode should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode. For applications where EL emission is viewed only through the cathode, the transmissive characteristics of the anode are immaterial and any conductive material can be used, transparent, opaque or reflective. Example conductors for this application include, but are not limited to, gold, iridium, molybdenum, palladium, and platinum. Desired anode materials are commonly deposited by any suitable means such as evaporation, sputtering, chemical vapor deposition, or electrochemical means. Anodes can be patterned using well-known photolithographic processes. Optionally, anodes may be polished prior to application of other layers to reduce surface roughness so as to minimize shorts or enhance reflectivity.

Cathode

When light emission is viewed solely through the anode, the cathode used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One useful cathode material is comprised of a Mg:Ag alloy wherein the percentage of silver is in the range of 1 to 20%, as described in U.S. Pat. No. 4,885,221. Another suitable class of cathode materials includes bilayers comprising the cathode and a thin electron-injection layer (EIL) in contact with an organic layer (e.g., an electron transporting layer (ETL)) which is capped with a thicker layer of a conductive metal. Here, the EIL preferably includes a low work function metal or metal salt, and if so, the thicker capping layer does not need to have a low work function. One such cathode is comprised of a thin layer of LiF followed by a thicker layer of Al as described in U.S. Pat. No. 5,677,572. An ETL material doped with an alkali metal, for example, Li-doped Alq, is another example of a useful EIL. Other useful cathode material sets include, but are not limited to, those disclosed in U.S. Pat. Nos. 5,059,861, 5,059,862 and 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in U.S. Pat. Nos. 4,885,211, 5,247,190, JP 3,234,963, U.S. Pat. Nos. 5,703,436, 5,608,287, 5,837,391, 5,677,572, 5,776, 622, 5,776,623, 5,714,838, 5,969,474, 5,739,545, 5,981,306, 6,137,223, 6,140,763, 6,172,459, EP1076368, U.S. Pat. Nos. 6,278,236 and 6,284,3936. Cathode materials are typically deposited by any suitable method such as evaporation, sputtering, or chemical vapor deposition. When needed, patterning can be achieved through many well known methods including, but not limited to, through-mask deposition, integral shadow masking as described in U.S. Pat. No. 5,276,380 and EP0732868, laser ablation, and selective chemical vapor deposition.

Hole-Injecting Layer (HIL)

A hole-injecting layer may be provided between anode and hole-transporting layer. The hole-injecting material can serve to improve the film formation property of subsequent organic layers and to facilitate injection of holes into the hole-transporting layer. Suitable materials for use in the hole-injecting layer include, but are not limited to, porphyrinic compounds as described in U.S. Pat. No. 4,720,432, plasma-deposited fluorocarbon polymers as described in U.S. Pat. No. 6,208,075, and some aromatic amines, for example, m-MTDATA (4,4',4"-tris[(3-methylphenyl)phenylamino]triphenylamine). Alternative hole-injecting materials reportedly useful in organic EL devices are described in EP0891121 and EP1029909. (Phthalocyanine copper complex) (CuPC) and (4,4',4"-tris(N-(naphth-2-yl)-N-phenyl-amino)triphenylamine)(2-TNATA) can advantageously be used.

Hole-Transporting Layer (HTL)

The hole-transporting layer of the organic EL device contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated in U.S. Pat. No. 3,180,730. Other suitable triarylamines substituted with one or more vinyl radicals and/or comprising at least one active hydrogen containing group are disclosed in U.S. Pat. Nos. 3,567,450 and 3,658,520. A more preferred class of aromatic tertiary amines are those which include at least two aromatic tertiary amine moieties as described in U.S. Pat. Nos. 4,720,432 and 5,061,569. Such compounds include those represented by structural formula

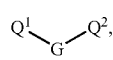

(A)

wherein $Q^1$ and $Q^2$ are independently selected aromatic tertiary amine moieties and G is a linking group such as an arylene, cycloalkylene, or alkylene group of a carbon to carbon bond. In one embodiment, at least one of $Q^1$ or $Q^2$ contains a polycyclic fused ring structure, e.g., a naphthalene. When G is an aryl group, it is conveniently a phenylene, biphenylene, or naphthalene moiety.

A useful class of triarylamines satisfying structural formula (A) and containing two triarylamine moieties is represented by structural formula

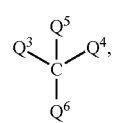

(B)

where $Q^3$ and $Q^4$ each independently represents a hydrogen atom, an aryl group, or an alkyl group or $Q^3$ and $Q^4$ together represent the atoms completing a cycloalkyl group; and $Q^5$ and $Q^6$ each independently represents an aryl group, which is in turn substituted with a diaryl substituted amino group, as indicated by structural formula

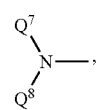

(C)

wherein $Q^7$ and $Q^8$ are independently selected aryl groups. In one embodiment, at least one of $Q^7$ or $Q^8$ contains a polycyclic fused ring structure, e.g., a naphthalene.

Another class of aromatic tertiary amines are the tetraaryldiamines. Desirable tetraaryldiamines include two diarylamino groups, such as indicated by formula (C), linked through an arylene group. Useful tetraaryldiamines include those represented by formula

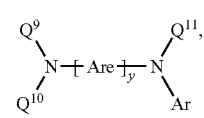

(D)

wherein each Are is an independently selected arylene group, such as a phenylene or anthracene moiety, n is an integer of from 1 to 4, and Ar, $Q^9$, $Q^{10}$, and $Q^{11}$ are independently selected aryl groups. In a typical embodiment, at least one of Ar, $Q^9$, $Q^{10}$, and $Q^{11}$ is a polycyclic fused ring structure, e.g., a naphthalene. The various alkyl, alkylene, aryl, and arylene moieties of the foregoing structural formulae (A), (B), (C), (D), can each in turn be substituted. Typical substituents include alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms, e.g. cyclopentyl, cyclohexyl, and cycloheptyl ring structures. The aryl and arylene moieties are usually phenyl and phenylene moieties.

The hole-transporting layer can be formed of a single or a mixture of aromatic tertiary amine compounds. Specifically, one may employ a triarylamine, such as a triarylamine satisfying the formula (B), in combination with a tetraaryldiamine, such as indicated by formula (D). When a triarylamine is employed in combination with a tetraaryldiamine, the latter is positioned as a layer interposed between the triarylamine and the electron injecting and transporting layer. Illustrative of useful aromatic tertiary amines are the following: 1,1-Bis(4-di-p-tolylaminophenyl)cyclohexane, 1,1-bis(4-di-p-tolylaminophenyl)-4-phenylcyclohexane, N,N,N',N'-tetraphenyl-4,4'''-diamino-1,1':4',1":4",1'''-guaterphenyl bis(4-dimethylamino-2-methylphenyl)phenylmethane, 1,4-bis[2-[4-[N,N-di(p-toly)amino]phenyl]vinyl]benzene (BD-TAPVB), N,N,N',N'-tetra-p-tolyl-4,4'-diaminobiphenyl, N,N,N',N'-tetraphenyl-4,4'-diaminobiphenyl, N,N,N',N'-tetra-1-naphthyl-4,4'-diaminobiphenyl, N,N,N',N'-tetra-2-naphthyl-4,4'-diaminobiphenyl, N-phenylcarbazole, 4,4'-bis[N-(1-naphthyl)-N-phenylamino]biphenyl (NPB), 4,4'-bis[N-(1-naphthyl)-N-(2-naphthyl)amino]biphenyl (TNB), 4,4'-bis[N-(1-naphthyl)-N-phenylamino]p-terphenyl, 4,4'-bis[N-(2-naphthyl)-N-phenylamino]biphenyl, 4,4'-bis[N-(3-acenaphthenyl)-N-phenylamino]biphenyl, 1,5-bis[N-(1-naphthyl)-N-phenylamino]naphthalene, 4,4'-bis[N-(9-anthryl)-N-phenylamino]biphenyl, 4,4'-bis[N-(1-anthryl)-

N-phenylamino]-p-terphenyl, 4,4'-bis[N-(2-phenanthryl)-N-phenylamino]biphenyl, 4,4'-bis[N-(8-fluoranthenyl)-N-phenylamino]biphenyl, 4,4'-bis[N-(2-pyrenyl)-N-phenylamino]biphenyl, 4,4'-bis[N-(2-naphthacenyl)-N-phenylamino]biphenyl, 4,4'-bis[N-(2-perylenyl)-N-phenylamino]biphenyl, 4,4'-bis[N-(1-coronenyl)-N-phenylamino]biphenyl, 2,6-bis(di-p-tolylamino) naphthalene, 2,6-bis[di-(1-naphthyl)amino]naphthalene, 2,6-bis[N-(1-naphthyl)-N-(2-naphthyl)amino]naphthalene, N,N,N',N'-tetra(2-naphthyl)-4,4''-diamino-p-terphenyl, 4,4'-bis{N-phenyl-N-[4-(1-naphthyl)-phenyl]amino}biphenyl, 2,6-bis[N,N-di(2-naphthyl)amino]fluorine, 4,4',4''-tris[(3-methylphenyl)phenylamino]triphenylamine (MTDATA), and 4,4'-Bis[N-(3-methylphenyl)-N-phenylamino]biphenyl (TPD). A hole transport layer may be used to enhance conductivity. NPD and TPD are examples of intrinsic hole transport layers. An example of a p-doped hole transport layer is m-MTDATA doped with $F_4$-TCNQ at a molar ratio of 50:1 as disclosed in U.S. Pat. No. 6,337,102 or DE10058578.

Another class of useful hole-transporting materials includes polycyclic aromatic compounds as described in EP1009041. Tertiary aromatic amines with more than two amine groups may be used including oligomeric materials. In addition, polymeric hole-transporting materials can be used such as poly(N-vinylcarbazole) (PVK), polythiophenes, polypyrrole, polyaniline, and copolymers such as poly(3,4-ethylenedioxythiophene)/poly(4-styrenesulfonate) also called PEDOT/PSS.

Fluorescent Light-Emitting Materials and Layers (LEL)

In addition to the phosphorescent materials, other light emitting materials may be used in the OLED device, including fluorescent materials. Although the term "fluorescent" is commonly used to describe any light emitting material, in this case we are referring to a material that emits light from a singlet excited state. Fluorescent materials may be used in the same layer as the phosphorescent material, in adjacent layers, in adjacent pixels, or any combination. Care must be taken not to select materials that will adversely affect the performance of the phosphorescent materials. One skilled in the art will understand that triplet excited state energies of materials in the same layer as the phosphorescent material or in an adjacent layer must be appropriately set so as to prevent unwanted quenching. As more fully described in U.S. Pat. Nos. 4,769,292 and 5,935,721, the light-emitting layer (LEL) of the organic EL element includes a luminescent fluorescent or phosphorescent material where electroluminescence is produced as a result of electron-hole pair recombination in this region. The light-emitting layer can be comprised of a single material, but more commonly consists of a host material doped with a guest emitting material or materials where light emission comes primarily from the emitting materials and can be of any color. The host materials in the light-emitting layer can be an electron-transporting material, as defined below, a hole-transporting material, as defined above, or another material or combination of materials that support hole-electron recombination. Fluorescent emitting materials are typically incorporated at 0.01 to 10% by weight of the host material. The host and emitting materials can be small non-polymeric molecules or polymeric materials such as polyfluorenes and polyvinylarylenes (e.g., poly(p-phenylenevinylene), PPV). In the case of polymers, small molecule emitting materials can be molecularly dispersed into a polymeric host, or the emitting materials can be added by copolymerizing a minor constituent into a host polymer. Host materials may be mixed together in order to improve film formation, electrical properties, light emission efficiency, lifetime, or manufacturability. The host may comprise a material that has good hole-transporting properties and a material that has good electron-transporting properties.

Host and emitting materials known to be of use include, but are not limited to, those disclosed in U.S. Pat. Nos. 4,768,292, 5,141,671, 5,150,006, 5,151,629, 5,405,709, 5,484,922, 5,593,788, 5,645,948, 5,683,823, 5,755,999, 5,928,802, 5,935,720, 5,935,721, and 6,020,078.

Metal complexes of 8-hydroxyquinoline and similar derivatives (Formula E) constitute one class of useful host compounds capable of supporting electroluminescence, and are particularly suitable for light emission of wavelengths longer than 500 nm, e.g., green, yellow, orange, and red.

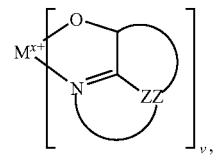

wherein M represents a metal; v is an integer of from 1 to 4; and ZZ independently in each occurrence represents the atoms completing a nucleus having at least two fused aromatic rings. From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such aluminum or gallium, or a transition metal such as zinc or zirconium. Generally any monovalent, divalent, trivalent, or tetravalent metal known to be a useful chelating metal can be employed. ZZ completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:

CO-1: Aluminum trisoxine [alias, tris(8-quinolinolato)aluminum(III)]

CO-2: Magnesium bisoxine [alias, bis(8-quinolinolato)magnesium(II)]

CO-3: Bis[benzo{f}-8-quinolinolato]zinc(II)

CO-4: Bis(2-methyl-8-quinolinolato)aluminum(III)-µ-oxo-bis(2-methyl-8-quinolinolato)aluminum(III)

CO-5: Indium trisoxine [alias, tris(8-quinolinolato)indium]

CO-6: Aluminum tris(5-methyloxine) [alias, tris(5-methyl-8-quinolinolato) aluminum(III)]

CO-7: Lithium oxine [alias, (8-quinolinolato)lithium(I)]

CO-8: Gallium oxine [alias, tris(8-quinolinolato)gallium (III)]

CO-9: Zirconium oxine [alias, tetra(8-quinolinolato)zirconium(IV)]

Useful fluorescent emitting materials include, but are not limited to, derivatives of anthracene, tetracene, xanthene, perylene, rubrene, coumarin, rhodamine, and quinacridone, dicyanomethylenepyran compounds, thiopyran compounds, polymethine compounds, pyrilium and thiapyrilium compounds, fluorene derivatives, periflanthene derivatives, indenoperylene derivatives, bis(azinyl)amine boron compounds, bis(azinyl)methane compounds, and carbostyryl compounds. Illustrative examples of useful materials include, but are not limited to, compounds L1 to L52 described in U.S. Pat. No. 7,090,930B2.

Electron-Transporting Layer (ETL)

Preferred thin film-forming materials for use in forming the electron-transporting layer of the organic EL devices of this invention are metal chelated oxinoid compounds, including chelates of oxine itself (also commonly referred to as 8-quinolinol or 8-hydroxyquinoline). Such compounds help to inject and transport electrons and exhibit both high levels of performance and are readily fabricated in the form of thin films. Exemplary of contemplated oxinoid compounds are those satisfying structural formula (E), previously described. Other electron-transporting materials include various butadiene derivatives as disclosed in U.S. Pat. No. 4,356,429 and various heterocyclic optical brighteners as described in U.S. Pat. No. 4,539,507. Benzazoles satisfying structural formula (G) are also useful electron transporting materials. Triazines are also known to be useful as electron transporting materials. Doping may be used to enhance conductivity. Alq$_3$ is an example of an intrinsic electron transport layer. An example of an n-doped electron transport layer is BPhen doped with Li at a molar ratio of 1:1, as disclosed in U.S. Pat. No. 6,337,102.

Deposition of Organic Layers

The organic materials mentioned above are suitably deposited by any means suitable for the form of the organic materials. In the case of small molecules, they are conveniently deposited through thermal evaporation, but can be deposited by other means such as from a solvent with an optional binder to improve film formation. If the material is soluble or in oligomeric/polymeric form, solution processing is usually preferred e.g. spin-coating, ink-jet printing. Dendrimer substituents may be used to enhance the ability of small molecules to undergo solution processing. Patterned deposition can be achieved using shadow masks, integral shadow masks (U.S. Pat. No. 5,294,870), spatially-defined thermal dye transfer from a donor sheet (U.S. Pat. Nos. 5,688,551, 5,851, 709 and 6,066,357) and inkjet method (U.S. Pat. No. 6,066, 357).

Encapsulation

Most OLED devices are sensitive to moisture or oxygen, or both, so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as SiO$_x$, Teflon, and alternating inorganic/polymeric layers are known in the art for encapsulation.

Devices fabricated in accordance with embodiments of the invention may be incorporated into a wide variety of consumer products, including flat panel displays, computer monitors, televisions, billboards, lights for interior or exterior illumination and/or signalling, fully transparent displays, flexible displays, laser printers, cell phones, personal digital assistants (PDAs), laptop computers, digital cameras, camcorders, viewfinders, micro-displays, vehicles, theatre or stadium screen, or a sign. Various control mechanism may be used to control devices fabricated in accordance with the present invention, including passive matrix and active matrix.

Various features and aspects of the present invention are illustrated further in the examples that follow. While these examples are presented to show one skilled in the art how to operate within the scope of this invention, they are not to serve as a limitation on the scope of the invention where such scope is only defined in the claims. Unless otherwise indicated in the following examples and elsewhere in the specification and claims, all parts and percentages are by weight, temperatures are in degrees centigrade and pressures are at or near atmospheric.

EXAMPLES

Example 1

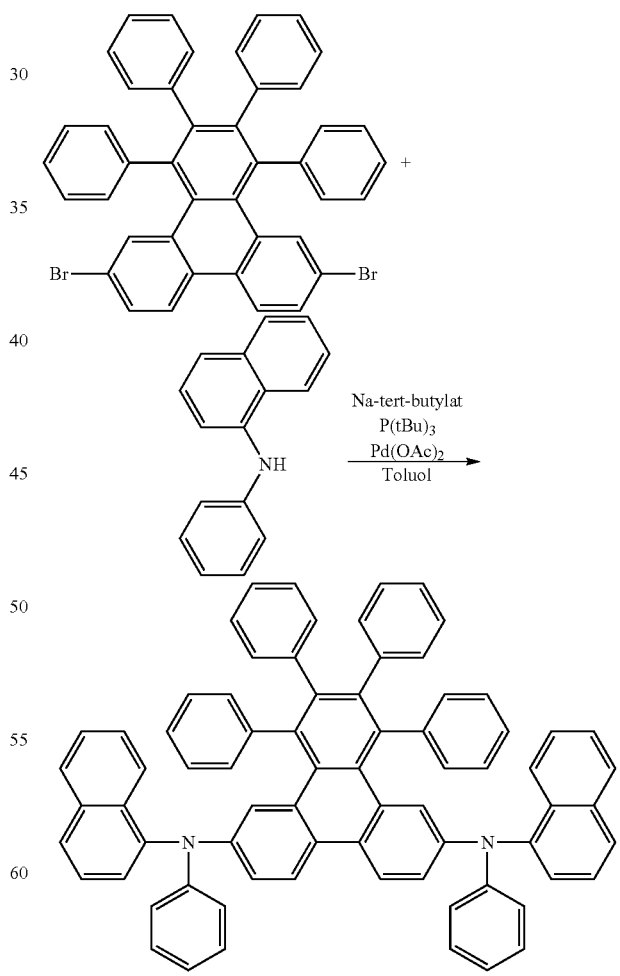

6,11-Dibromo-1,2,3,4-tetraphenyl-triphenylene can be prepared as described in example 1 of PCT/EP2007/057408.

1.80 g (2.61 mmol) 6,11-dibromo-1,2,3,4-tetraphenyl-triphenylene and 540 mg (5.60 mmol) sodium tert-butoxide are dissolved in 40 ml toluene. The reaction mixture is degassed with argon and 29 mg (0.13 mmol) palladium(II) acetate are added. Then 105 mg (0.520 mmol) tri-tert-butylphosphine are added. A degassed solution of 1.77 g (8.08 mmol) naphthalen-1-yl-phenyl-amine in 15 ml toluene is added and the reaction mixture is heated at 90° C. for 3 h.

20 ml of a 1% sodium cyanide solution are added to the reaction mixture and the reaction mixture is refluxed for 1 h. The reaction mixture is extracted with diethylether and then dichloromethane. The organic phase is dried with magnesium sulfate. The solvent is removed in vacuum. The product is purified by chromatography on silica gel with toluene/cyclohexane (1/4). $^1$H-NMR 300 MHz (CDCl$_3$) δ=6.50-6.90 (m, 22H), 7.00-7.50 (m, 20H), 7.65-7.25 (m, 4H), 8.85 (d, J=8.1 Hz, 2H) 8.18 (d, J=8.8 Hz, 2H)

Example 2

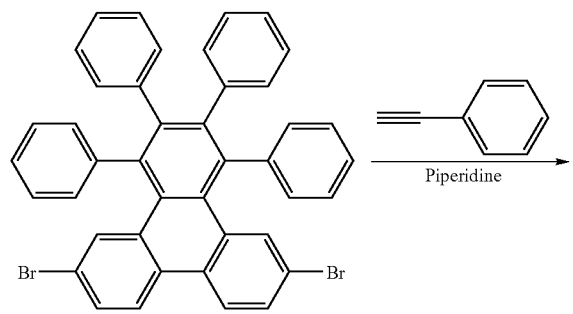

-continued

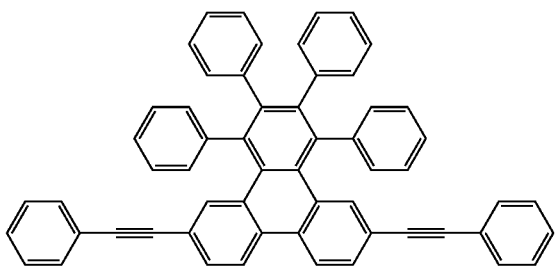

a.) 4.44 g (43.5 mmol) ethynyl-benzene, 280 mg (1.45 mmol) copper(I)iodide and 340 mg (0.29 mmol) terakis(triphenylphosphine) palladium(0) are added to 10.0 g (14.5 mmol) 6,11-dibromo-1,2,3,4-tetraphenyl-triphenylene in 200 ml piperidine. The reaction mixture is stirred for 22 h at 130° C. under argon. The solids are filtered off. The filtrate contains the target product and the monocoupling product. 2.96 g (26.6 mmol) ethynyl-benzene, 130 mg (0.725 mmol) copper(I)iodide and 170 mg (0.145 mmol) terakis(triphenylphosphine) palladium(0) are added to the filtrate in piperidine, The reaction mixture is stirred for 48 h at 130° C. under argon. The solids are filtered off. The solvent is removed in vacuum and the product is decocted 2 times with n-hexane.

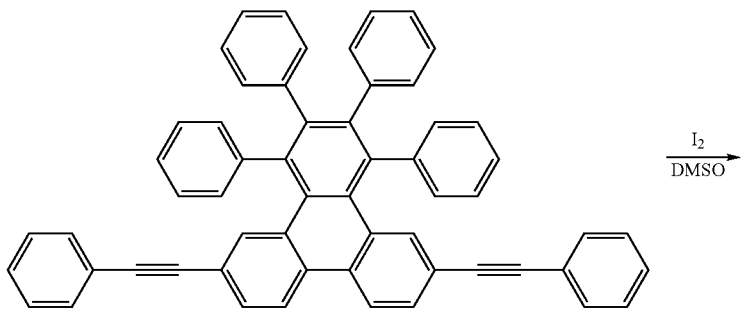

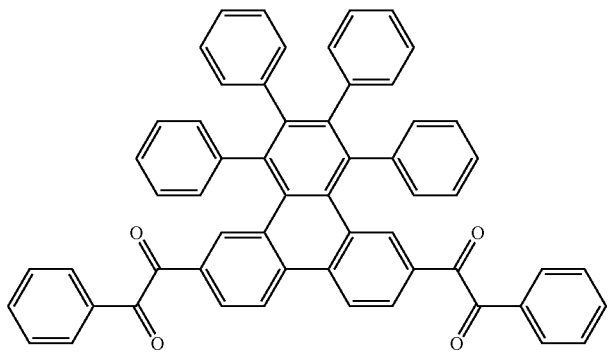

b) A mixture of 3.00 g (4.09 mmol) of the product of example 2a and 16.6 g (65.5 mmol) iodine are dissolved in 50 ml dimethyl sulfoxide (DMSO). The reaction mixture is stirred for 21 h at 160° C. and poured into water and the water phase is extracted with dichloromethane. The organic phase is washed with a 10% sodium thiosulfate solution. The organic phase is dried with sodium sulfate and the solvent is removed in vacuum. The product is isolated by column chromatography on silica gel with toluene.

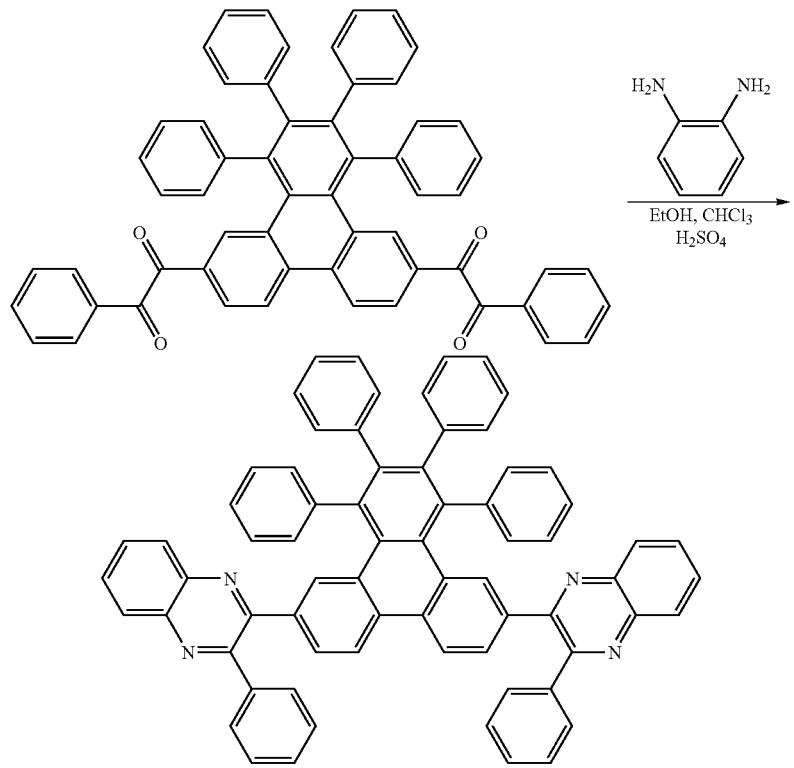

c) 540 mg (5.00 mmol) benzene-1,2-diamine are added to 2.00 g (2.51 mmol) of the product of example 2b in 80 ml ethanol and 40 ml chloroform. 12 drops sulfuric acid are added and the reaction mixture is refluxed for 4 days. The product is filtered off, washed with ethanol and 20% hydrochloric acid and soxhlet extracted with chloroform. Melting point: 288° C.

Example 3

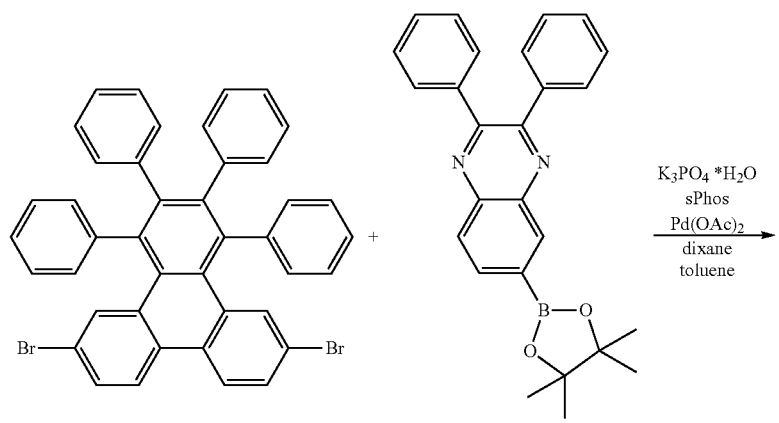

-continued

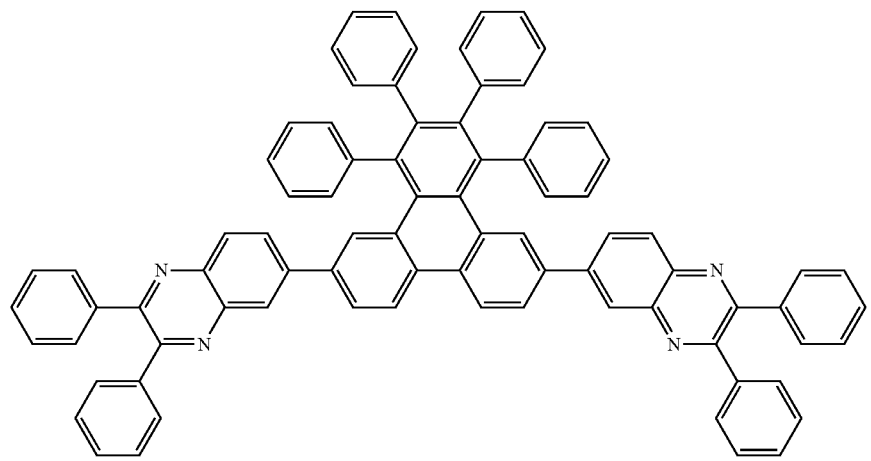

3.00 g (4.35 mmol) 6,11-dibromo-1,2,3,4-tetraphenyl-triphenylene and 3.90 g (9.56 mmol) 2,3-diphenyl-6-(4,4,5,5-tetramethyl-1,3,2-dioxaborolan-2-yl)-guinoxaline (example 5b of PCT/EP2008/053251) are dissolved in a mixture of 20 ml dioxane and 80 ml toluene. The solution is degassed with argon. 107 mg (0.261 mmol) dicyclohexyl-(2',6'-dimethoxy-biphenyl-2-yl)-phosphane and 9.8 mg (0.043 mmol) palladium(II) acetate are added. The solution is degassed with argon. A degassed solution of 5.27 g (21.7 mmol) potassium phosphate tribasic monohydrate ($K_3PO_4 \cdot H_2O$) in 16 ml water is added. The reaction mixture is stirred under argon for 18 h at 90° C. The product is filtered off, washed with toluene, dissolved in dichloromethane and is filtered on silica gel. Melting point: 367° C.

Example 4

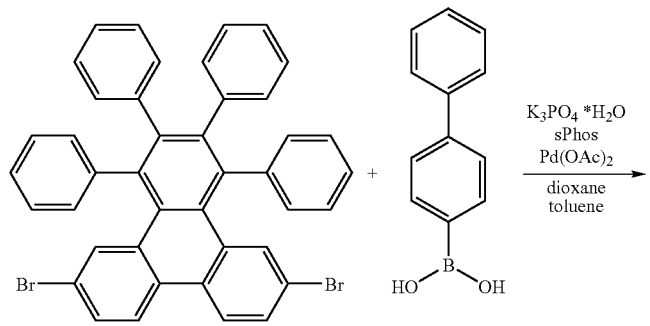

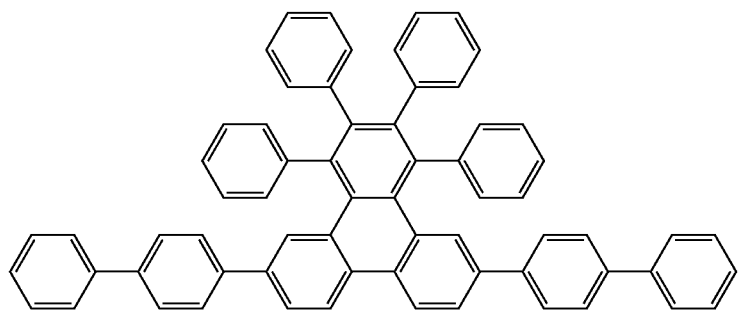

A mixture of 20 ml dioxane and 80 ml toluene is added to 3.00 g (4.35 mmol) 6,11-dibromo-1,2,3,4-tetraphenyl-triphenylene and 1.89 g (9.56 mmol) 3-biphenyl boronic acid. The mixture is degassed with argon. 107 mg (0.261 mmol) dicyclohexyl-(2',6'-dimethoxy-biphenyl-2-yl)-phosphene and 9.8 mg (0.043 mmol) palladium(II) acetate are added. The solution is degassed with argon. A degassed solution of 5.27 g (21.7 mmol) potassium phosphate tribasic monohydrate ($K_3PO_4 \cdot H_2O$) in 16 ml water is added. The reaction mixture is stirred under argon for 18 h at 90° C. The product is filtered off, washed with toluene and soxhlet extracted with dichloromethane. Melting point: 334° C.

Example 5

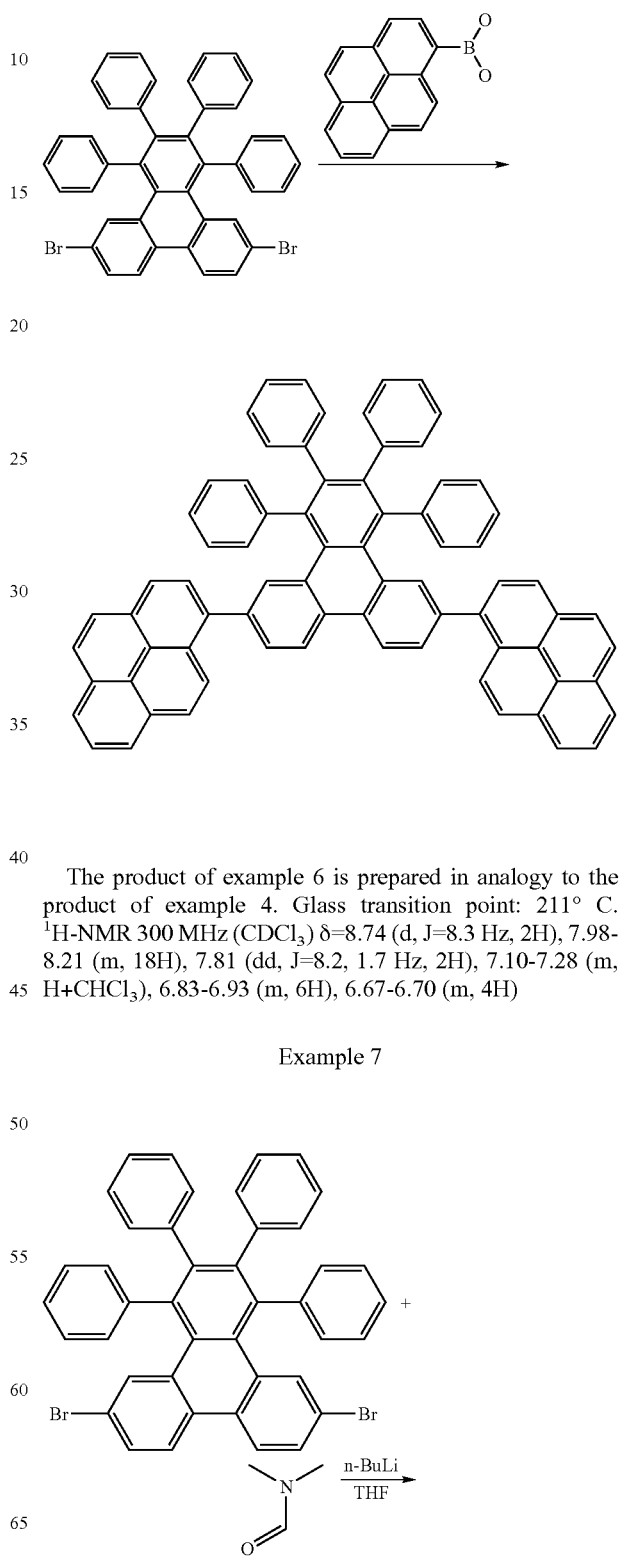

The product of example 5 is prepared in analogy to the product of example 1. Xylene is used instead of toluene as solvent. Melting point: 336° C.

Example 6

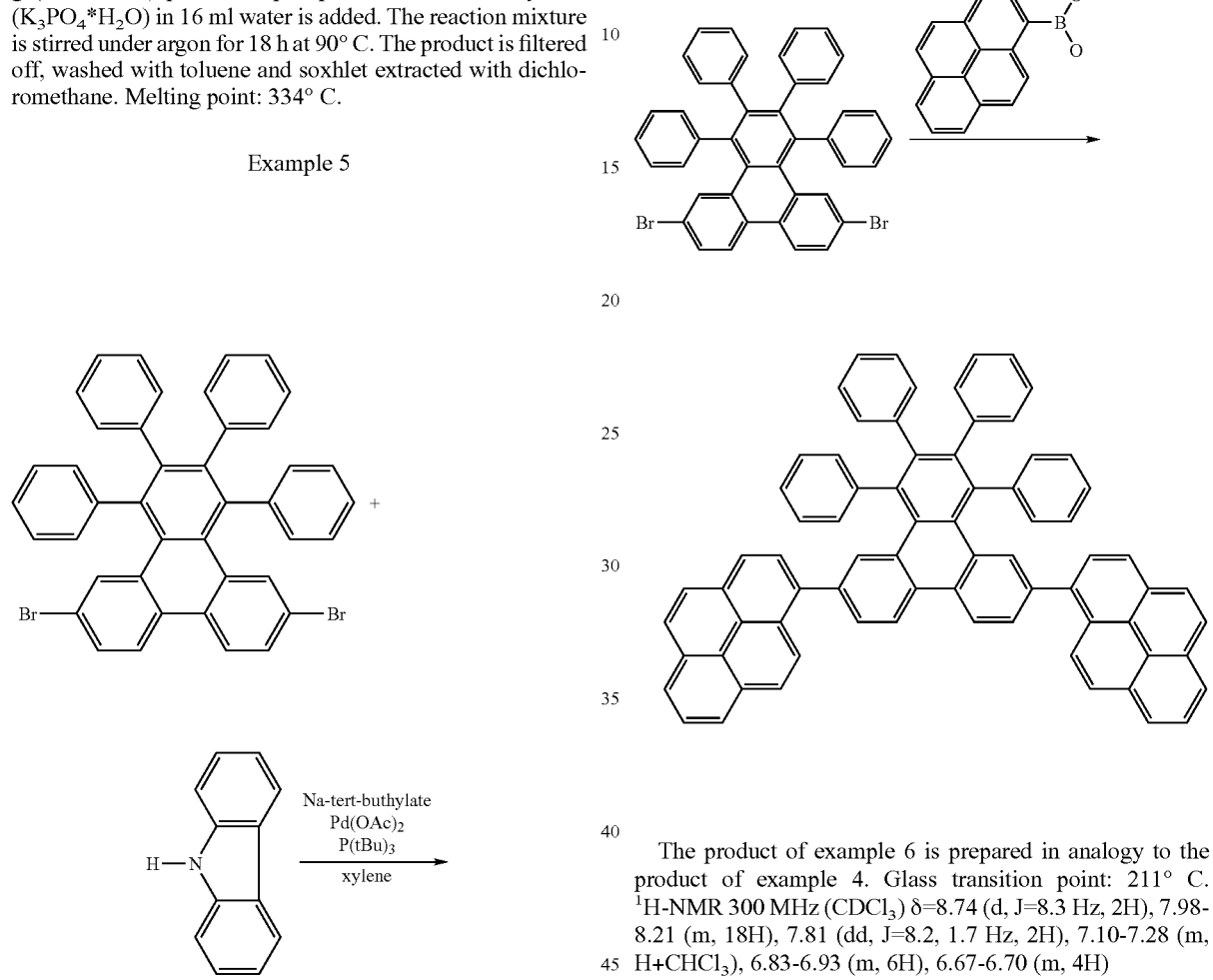

The product of example 6 is prepared in analogy to the product of example 4. Glass transition point: 211° C. $^1$H-NMR 300 MHz ($CDCl_3$) δ=8.74 (d, J=8.3 Hz, 2H), 7.98-8.21 (m, 18H), 7.81 (dd, J=8.2, 1.7 Hz, 2H), 7.10-7.28 (m, H+$CHCl_3$), 6.83-6.93 (m, 6H), 6.67-6.70 (m, 4H)

Example 7

-continued

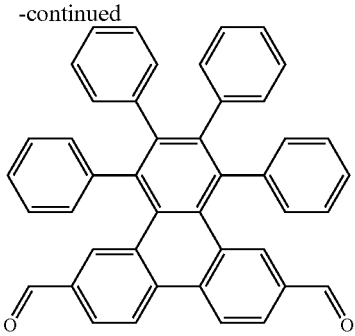

a.) 5.00 g (7.24 mmol) 6,11-dibromo-1,2,3,4-tetraphenyl-triphenylene are dissolved in 30 ml water free THF (tetrahydrofurane) under argon. 6.4 ml (15.9 mmol) n-butyl lithium solution (2.5 M in hexane) are slowly added to this mixture at −78° C. After adding the n-butyl lithium solution the reaction mixture is stirred for 10 minutes. 5.29 g (72.4 mmol) DMF (N,N-dimethyl-formamide) are added. The reaction mixture is stirred for 10 min at −78° C. and is then warmed up to 25° C. The reaction mixture is poured into water and the water phase is extracted with dichloromethane. The organic phase is dried with sodium sulfate and the solvent is removed in vacuum. After a column chromatography on silica gel with toluene/hexane 1/1 the product is isolated.

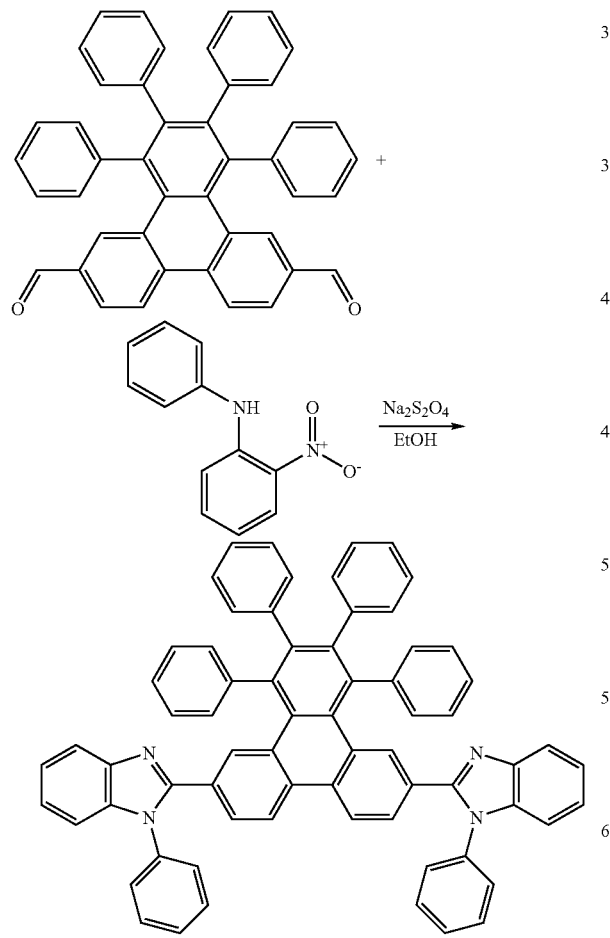

b.) 800 mg (3.74 mmol) (2-nitro-phenyl)-phenyl-amine and 1.77 g (10.2 mmol) sodium dithionite are added to 1.00 g (1.70 mmol) of the product of example 7a in 40 ml ethanol, under argon. The reaction mixture is refluxed under argon for 48 h, poured into water and the water phase is extracted with dichloromethane. The solvent was removed in vacuum. The dried product contains a mixture of target product and the monobenzoimidazole intermediate. 400 mg (1.87 mmol) (2-nitro-phenyl)-phenyl-amine and 900 mg (5.1 mmol) sodium dithionite are added to the crude product in 40 ml ethanol under argon. The reaction mixture is refluxed under argon for 48 h, cooled to 25° C., the product is filtered off and isolated after a column chromatography on silica gel with toluene/ethanol 6/1. Melting point: 361° C.

Example 8

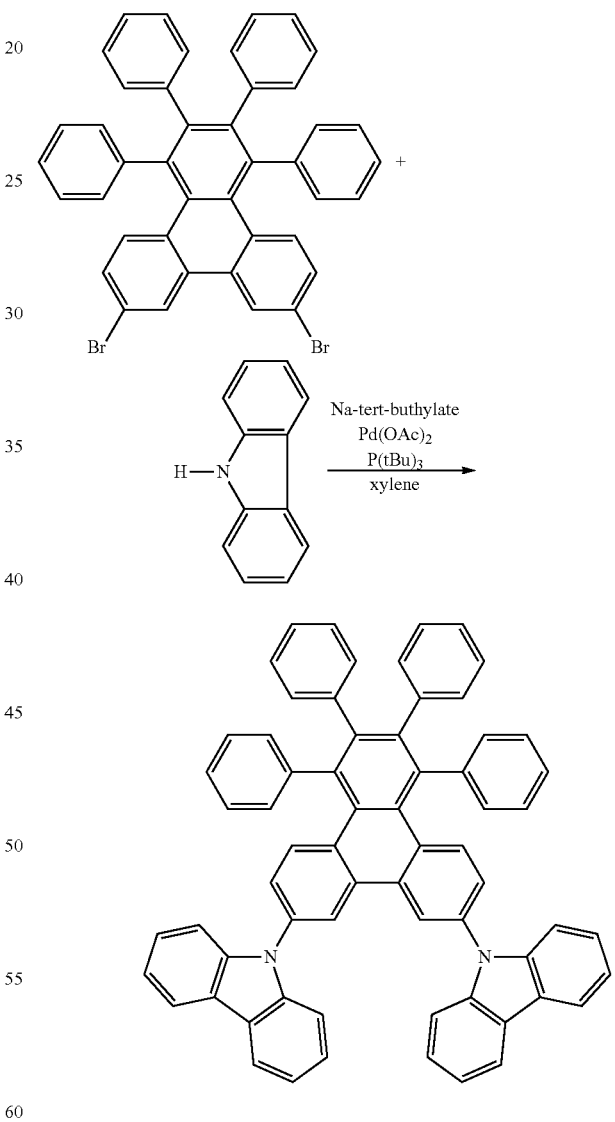

6,11-Dibromo-1,2,3,4-tetraphenyl-triphenylene can be prepared according to example 1 of PCT/EP2007/057408. The product of example 8 is prepared in analogy to the product of example 5. Melting point: 375° C.

Comparative Example 1

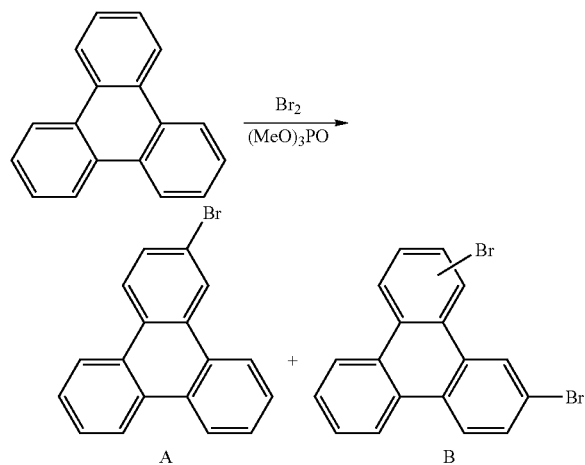

a) 21.0 g (0.131 mol) bromine in 30 ml phosphoric acid trimethyl ester are added to 10 g (43.8 mmol) triphenylene in 150 ml phosphoric acid trimethyl ester at 25° C. under nitrogen. The reaction mixture is stirred at 85° C. under nitrogen for 5 h, cooled to 25° C. and the solids are filtered off. The filtrate is left over night at 25° C. The formed precipitate is filtered off. The precipitate contains mostly bisbromid (mixture of isomers) B and lower quantities of mono bromide A.

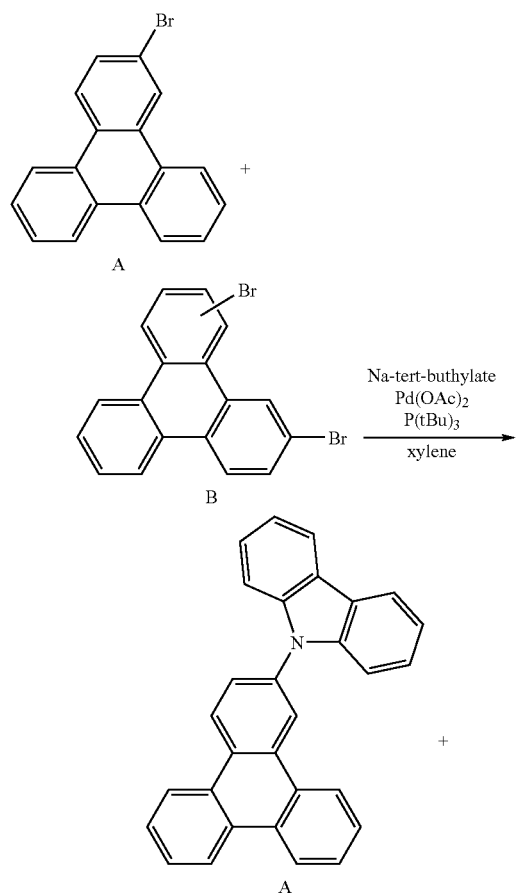

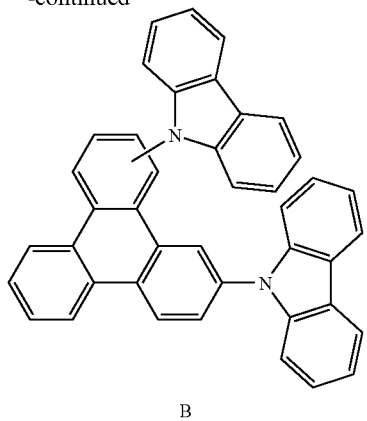

b) The product of comparative example 1a is reacted with carbazole in analogy to example 5. The products of this example are separated by column chromatography on silica gel with n-hexane/toluene 8/2. Product A is isolated as a single isomer. Product B is a mixture of inseparable isomers. Melting point of product A: 217° C.

As evident from the table below the glass transition points of the compounds of the present invention are higher than those of the prior art compounds, which fact indicates that the compounds of the present invention have a higher device stability (life time) than the prior art compounds.

| Example | $T_g$ |
|---|---|
| Example 5 | 193° C. |
| Example 8 | 202° C. |
| Comparison Example 1 Product A | 91° C. |
| Comparison Example 1 Product B | 129° C. |

DEVICE FABRICATION AND APPLICATION EXAMPLES

Devices are fabricated by thermal evaporation in high vacuum (<10$^{-6}$ mbar). The anode consists of ca. 1200 Å of indium tin oxide (ITO) previously deposited on a glass substrate. The cathode consists of 10 Å of LiF followed by 1000 Å of Al. All devices are tested immediately after preparation, without encapsulation, in the nitrogen atmosphere of a glove box (<1 ppm of H$_2$O and O$_2$). All materials used are of sublimed quality.

Application Example 1

The organic stack consists sequentially, from the ITO surface, of 600 Å of 2-TNATA (4,4',4"-tris(N-(naphth-2-yl)-N-phenyl-amino)triphenylamine) as the hole injection layer (HIL), 300 Å of 4,4'-bis[N-(1-naphtyl)-N-phenylamino]biphenyl (α-NPD) as the hole transport layer. The emissive layer consists of 300 Å of material from Example 5, Example 8, Product A and Product B, respectively (as host, Application Example 1a, 1b, 1c and 1d in the table below), in all cases doped with 10% of red emitter bis(1-(phenyl)isoquinoline) iridium (III) acetylanetonate ((abbreviation: Ir(piq)$_2$(acac), guest), followed by 10 nm of TPBI (1,3,5-tris(1-phenyl-1H-benzimidazol-2-yl)benzene) as the hole blocking layer and 30 nm of Alq$_3$ (tris-(8-hydroxy-chinolinato)-aluminium) as the electron transport layer.

Current efficiency, along with the onset voltage (C at 1000 cd/m²), CIE values and maximum luminance measured for devices prepared as above is reported in the table below:

| Appl. Example | HOST | C. Eff/1000 cd/m² | V/1000 cd/m² | CIE (x, y) | Max Lum/ cd/m² |
|---|---|---|---|---|---|
| 1a | Cpd. of Example 5 | 1.8 | 10.2 | 0.67, 0.31 | 2600 |
| 1b | Cpd. of Example 8 | 5.6 | 8.3 | 0.67, 0.31 | 8900 |
| 1c | Product A | 3.4 | 9.9 | 0.67, 0.31 | 3100 |
| 1d | Product B | 0.2 | 17.0 | 0.67, 0.31 | 300 |

As reported in the table above, the devices of Application Example 1a and 1b comprising the compounds of Example 5 and 8 show improved current efficiency in respect to the devices of Application Example 1c and 1d comprising comparative products A and B. In particular, onset voltage of the device of Application Example 1b comprising the Compound of Example 8 is only 8.3 V, which is a quite low value, unmatched by the devices of Application Examples 1c and d using comparative products A and B in a similar device set-up.

Application Example 2

The organic stack consists sequentially, from the ITO surface, of 600 Å of 2-TNATA (4,4',4"-tris(N-(naphth-2-yl)-N-phenyl-amino)triphenylamine) as the hole injection layer (HIL), 300 Å of 4,4'-bis[N-(1-naphtyl)-N-phenylamino]biphenyl (α-NPD) as the hole transport layer. The emissive layer consists of 300 Å of material from Example 5, Example 8, Product A and Product B, respectively (as host, Application Example 2a, 2b, 2c and 2d in the table below), in all cases doped with 10% of red emitter (acetylanetonato)bis(2,3,5-triphenylpyrazinato)iridium(III) (abbreviation: Ir(tppr)$_2$(acac); guest), followed by 10 nm of TPBI (1,3,5-tris(1-phenyl-1H-benzimidazol-2-yl)benzene) as the hole blocking layer and 30 nm of Alq$_3$ (tris-(8-hydroxy-chinolinato)-aluminium) as the electron transport layer.

Current efficiency, along with the onset voltage (C at 1000 cd/m²), CIE values and maximum luminance measured for devices prepared as above is reported in the table below:

| Appl. Example | HOST | C. Eff@1000 cd/m² | V@1000 cd/m² | CIE (x, y) | Max Lum/ cd/m² |
|---|---|---|---|---|---|
| 2a | Cpd. of Example 5 | 4.9 | 9.4 | 0.64, 0.34 | 5300 |
| 2b | Cpd. of Example 8 | 6.1 | 8.7 | 0.64, 0.34 | 7800 |
| 2c | Product A | 4 | 10.0 | 0.64, 0.34 | 3000 |
| 2d | Product B | 0.7 | 14.2 | 0.64, 0.34 | 850 |

As reported in the table above, the devices of Application Example 2a and 2b comprising the compounds of Example 5 and 8 show improved current. efficiency and maximal luminance in respect to the devices of Application Example 2c and 2d comprising comparative products A and B. In particular, onset voltage of the devices of Application Example 2a and 2b comprising the compounds of Example 5 and 8, respectively is much lower than that of the devices of Application Examples 2c and 2d comprising the comparative products A and B.

Application Example 3

The organic stack consists sequentially, from the ITO surface, of 100 Å of CuPC (Phthalocyanine copper complex) as the hole injection layer (HIL), 300 Å of 4,4'-bis[N-(1-naphtyl)-N-phenylamino]biphenyl (α-NPD) as the hole transport layer. The emissive layer consists of 300 Å of material from Example 5, Example 8, and product A respectively (as host, Application Examples 3a, 3b and 3c in the table below), in all cases doped with 6% of green emitter tris(2-phenyl-pyridyl)iridium complex (guest), followed by 10 nm of BAlq (bis(2-methyl-8-quinolinolato)-4-(phenyl-phenolato)aluminium-(III) as the hole blocking layer and 30 nm of Alq$_3$ (tris-(8-hydroxy-chinolinato)-aluminium) as the electron transport layer.

Current efficiency, along with the onset voltage (C at 1000 cd/m²), CIE values and maximum luminance measured for devices prepared as above is reported in the table below:

| Appl. Example | HOST | C. Eff@1000 cd/m² | V@1000 cd/m² | CIE (x, y) | Max Lum/ cd/m² |
|---|---|---|---|---|---|
| 3a | Cpd. of Example 5 | 14.8 | 9.8 | 0.32, 0.60 | 3100 |
| 3b | Cpd. of Example 8 | 5.1 | 8.0 | 0.32, 0.60 | 7500 |
| 3c | Product A | 2.5 | 10.4 | 0.32, 0.60 | 3000 |

As reported in the table above, the devices of Application Example 3a and 3b comprising the materials from Example 5 and 8 show improved current efficiency and maximal luminance in respect to the device of Application Example 3c comprising comparative product A, along with lower onset voltage. In particular, the device of application Example 3a comprising the compound of Example 5, shows a current efficiency of 14.8 Cd/A at 1000 Cd/m², which is significantly higher than the current efficiency of the device of Application Example 3c comprising comparative product A.

The invention claimed is:

1. An electroluminescent (EL) device, comprising a compound of the formula

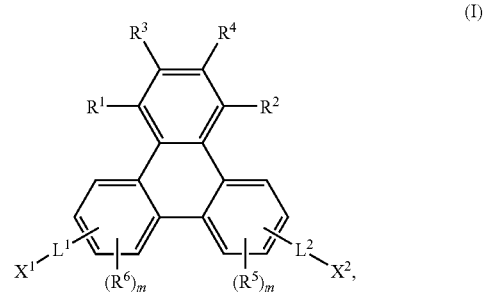

(I)

selected from the group consisting of

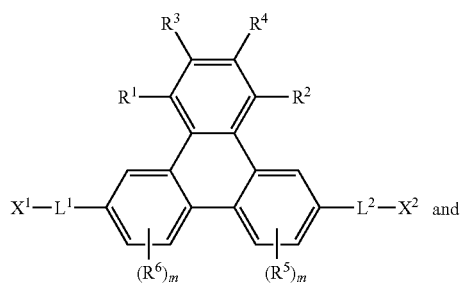 (II)

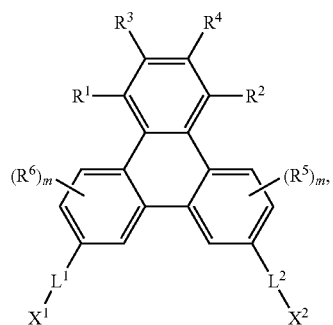 (III)

wherein m can be the same or different at each occurrence and is 0, 1, 2, or 3, $R^1$ and $R^2$ are a group of formula

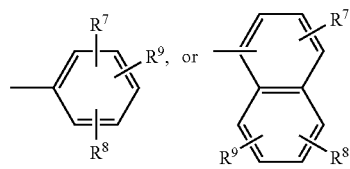

and $R^3$ is hydrogen and $R^4$ is a $C_1$-$C_{25}$alkyl group, or a group of formula

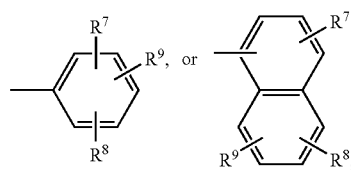

or $R^3$ and $R^4$ are a group of formula

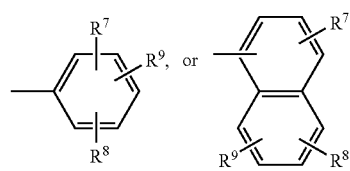

wherein $R^7$, $R^8$ and $R^9$ are independently of each other H, $C_1$-$C_{18}$alkyl, $C_1$-$C_{18}$alkoxy, or $C_1$-$C_{18}$alkyl which is interrupted by O, $R^5$ and $R^6$ are independently of each other halogen, or an organic substituent, or $R^5$ and $R^6$, which are adjacent to each other, together form an aromatic, or heteroaromatic ring, or ring system, which can optionally be substituted, and -$L^1$-$X^1$ and -$L^2$-$X^2$ are independently of each other a group of formula -$NA^1A^{1'}$ or a group

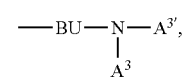

wherein $A^1$, $A^{1'}$, $A^3$ and $A^{3'}$ are independently of each other a $C_6$-$C_{24}$aryl group, or a $C_2$-$C_{30}$ heteroaryl group, which can optionally be substituted, selected from the group consisting of phenyl, naphthyl, anthryl, biphenylyl, 2-fluorenyl, phenanthryl, and perylenyl, which can optionally be substituted, said groups being selected from the group consisting of

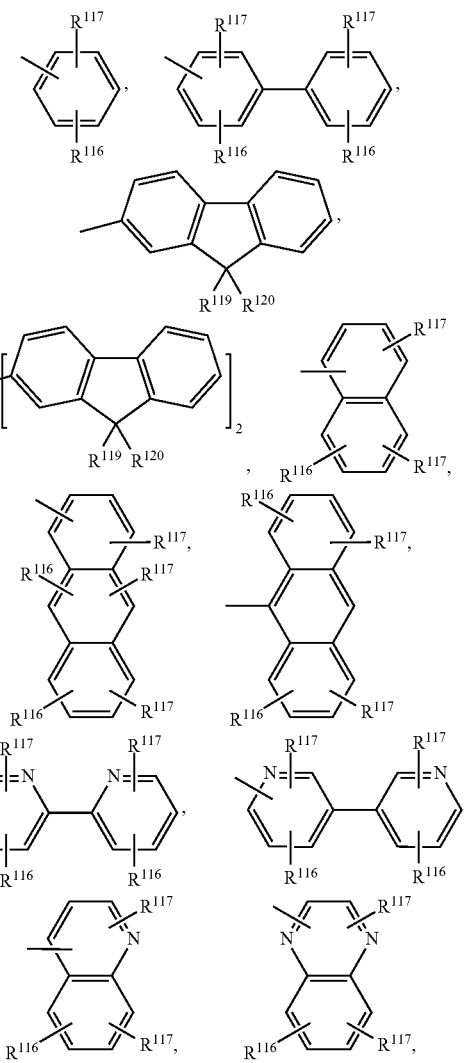

-continued

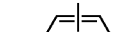

or $A^1$ and $A^{1'}$, or $A^3$ and $A^{3'}$ together with the nitrogen atom to which they are bonded form a heteroaromatic ring, or ring system, selected from the group consisting of

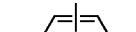

wherein m' is 0, 1, or 2;
m1 can be the same or different at each occurence and is 0, 1, 2, 3, or 4;
$R^{116}$, $R^{117}$ and $R^{117'}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$ heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{127}$, —C(=O)O$R^{127}$, or —C(=O)N$R^{127}R^{126}$, or
substituents $R^{116}$, $R^{117}$ and $R^{117'}$, which are adjacent to each other, can form a ring,
$R^{119}$ and $R^{120}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$ heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or
$R^{119}$ and $R^{120}$ together form a group of formula =$CR^{121}R^{122}$, wherein
$R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, $C_2$-$C_{20}$heteroaryl which is substituted by G, or
$R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—$R^{127}$, $R^{126}$ and $R^{127}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—,
BU is

wherein $R^{41}$ can be the same or different at each occurrence and is Cl, F, CN, $NR^{45}R^{45'}$, a $C_1$-$C_{25}$alkyl group, a $C_4$-$C_{18}$cycloalkyl group, a $C_1$-$C_{25}$alkoxy group, in which one or more carbon atoms which are not adjacent to each other could be replaced by —$NR^{45}$—, —O—, —S—, —C(=O)—O—, or —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, or
two or more groups $R^{41}$ form a ring system;
$R^{45}$ and $R^{45'}$ are independently of each other a $C_1$-$C_{25}$alkyl group, a $C_4$-$C_{18}$cycloalkyl group, in which one or more carbon atoms which are not adjacent to each other could be replaced by —$NR^{45''}$—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$,
$R^{45'}$ is a $C_1$-$C_{25}$alkyl group, or a $C_4$-$C_{18}$cycloalkyl group, and m1 can be the same or different at each occurrence and is 0, 1, 2, 3 or 4; or -$L^1$-$X^1$ and -$L^2$-$X^2$ are independently of each other a group

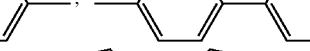

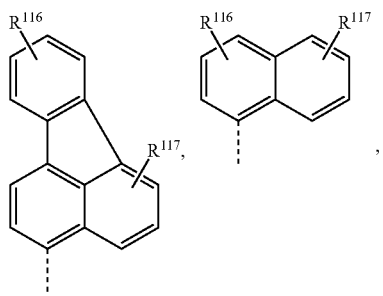
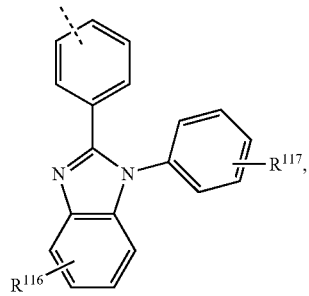
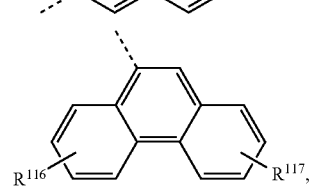
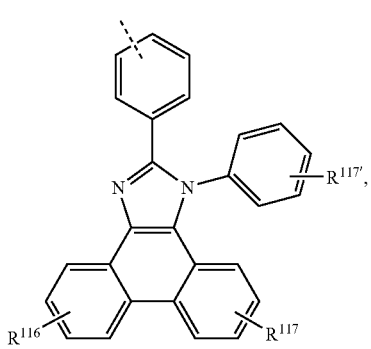
wherein
$R^{116}$, $R^{116'}$, $R^{117}$ and $R^{117'}$ are as defined above,
D is —CO—, —COO—, —S—, —SO—, —SO$_2$—, —O—, —NR$^{65}$—, —SiR$^{70}$R$^{71}$—, —POR$^{72}$—, —CR$^{63}$=CR$^{64}$—, or —C≡C—, and
E is –OR$^{69}$, —SR$^{69}$, —NR$^{65}$R$^{66}$, —COR$^{68}$, —COOR$^{67}$, —CONR$^{65}$R$^{66}$, —CN, or halogen,
G is E, or C$_1$-C$_{18}$alkyl; or -L$^1$-X$^1$ and -L$^2$-X$^2$ are independently of each other a group
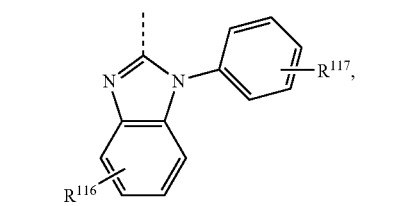
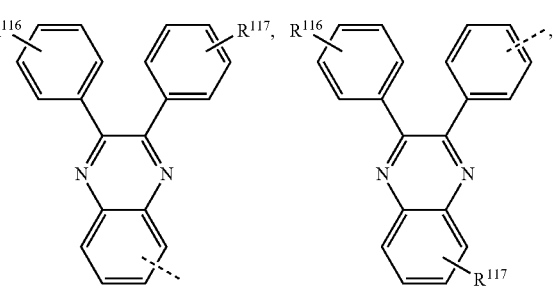
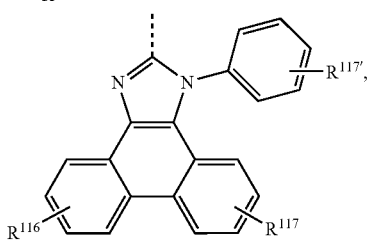
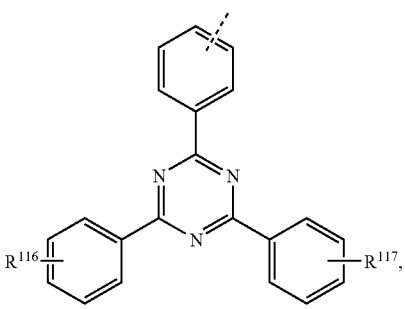
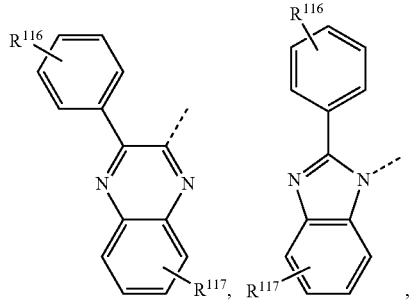
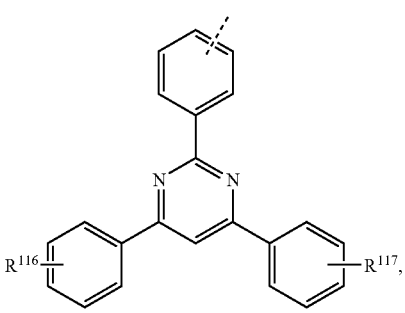

-continued

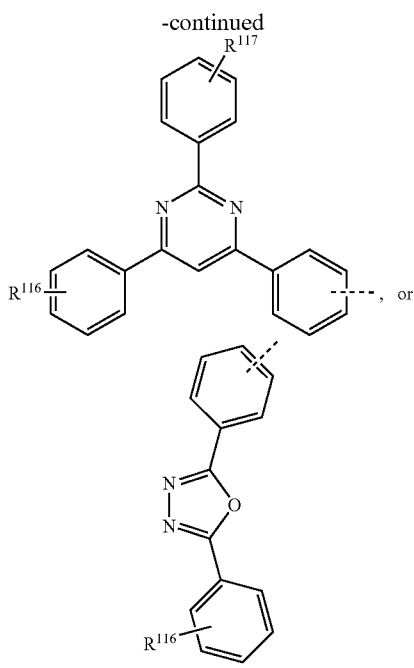

wherein $R^{116}$, $R^{117}$ and $R^{117'}$ are as defined above.

2. The EL device according to claim 1, comprising a compound of the formula (I), wherein -$L^1$-$X^1$ and -$L^2$-$X^2$ are independently of each other a group of formula

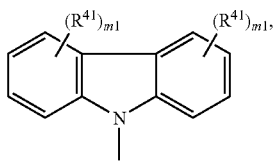

-$NA^1A^{1'}$, or a group

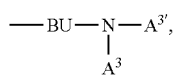

wherein $A^1$, $A^{1'}$, $A^3$ and $A^{3'}$ are independently of each other

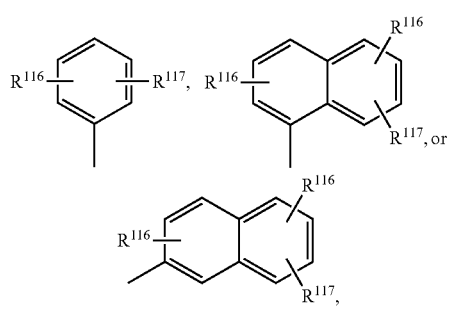

or $A^3$ and $A^{3'}$ together with the nitrogen atom to which they are bonded form a group of formula

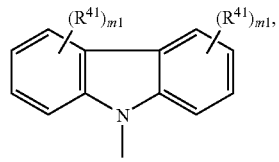

$R^{116}$ and $R^{117}$ are independently of each other $C_1$-$C_{25}$alkyl, which may optionally be interrupted by —O—, or $C_1$-$C_{25}$alkoxy;

Bu is

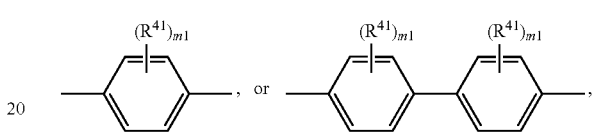

wherein $R^{41}$ can be the same or different at each occurence and is $C_1$-$C_{25}$alkyl, which may optionally be interrupted by —O—, or $C_1$-$C_{25}$alkoxy; and m1 is 0, 1, or 2.

3. The EL device according to claim 1, comprising a compound selected from

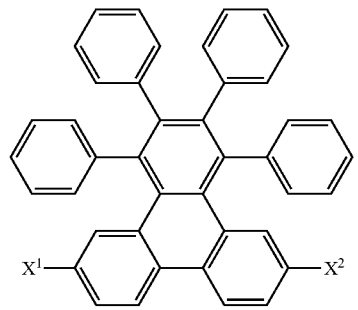

| Compound | $X^1 = X^2$ |
|---|---|
| A1 | HE-1 |
| A2 | HE-2 |
| A3 | HE-3 |
| A4 | HE-4 |
| A5 | HE-5 |
| A6 | HE-6 |
| A7 | HE-7 |
| A8 | HE-8 |
| A9 | HE-9 |
| A10 | AR-1 |
| A11 | AR-2 |
| A12 | AR-3 |
| A13 | AR-4 |
| A14 | AM-1 |
| A15 | AM-2 |
| A17 | AM-3 |
| A18 | AM-4 |
| A19 | AM-5 |
| A20 | AM-6 |
| A21 | AM-7 |

| Compound | $X^1 = X^2$ |
|---|---|
| B1 | HE-1 |
| B2 | HE-2 |
| B3 | HE-3 |
| B4 | HE-4 |
| B5 | HE-5 |
| B6 | HE-6 |
| B7 | HE-7 |
| B8 | HE-8 |
| B9 | HE-9 |
| B10 | AR-1 |
| B11 | AR-2 |
| B12 | AR-3 |
| B13 | AR-4 |
| B14 | AM-1 |
| B15 | AM-2 |
| B17 | AM-3 |
| B18 | AM-4 |
| B19 | AM-5 |
| B20 | AM-6 |
| B21 | AM-7 |
| Compound | $X^1 = X^2$ |
|---|---|
| C1 | HE-1 |
| C2 | HE-2 |
| C3 | HE-3 |
| C4 | HE-4 |
| C5 | HE-5 |
| C6 | HE-6 |
| C7 | HE-7 |
| C8 | HE-8 |
| C9 | HE-9 |
| C10 | AR-1 |
| C11 | AR-2 |
| C12 | AR-3 |
| C13 | AR-4 |
| C14 | AM-1 |
| C15 | AM-2 |
| C17 | AM-3 |
| C18 | AM-4 |
| C19 | AM-5 |
| C20 | AM-6 |
| C21 | AM-7 |
| Compound | $X^1 = X^2$ |
|---|---|
| D1 | HE-1 |
| D2 | HE-2 |
| D3 | HE-3 |
| D4 | HE-4 |
| D5 | HE-5 |
| D6 | HE-6 |
| D7 | HE-7 |
| D8 | HE-8 |
| D9 | HE-9 |
| D10 | AR-1 |
| D11 | AR-2 |
| D12 | AR-3 |
| D13 | AR-4 |
| D14 | AM-1 |
| D15 | AM-2 |
| D17 | AM-3 |
| D18 | AM-4 |
| D19 | AM-5 |
| D20 | AM-6 |
| D21 | AM-7 |
wherein HE-1 is 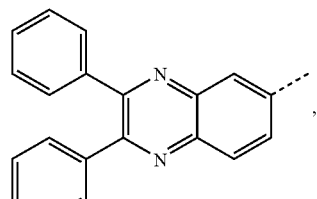,
HE-2 is 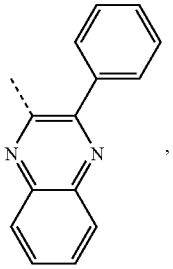,

| 85 -continued | 86 -continued |
|---|---|
| 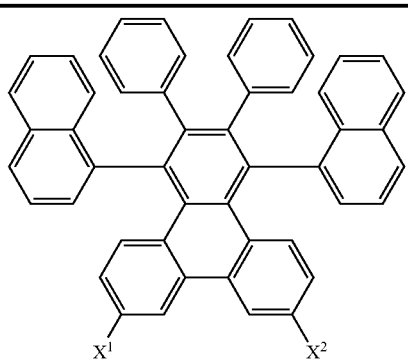 | 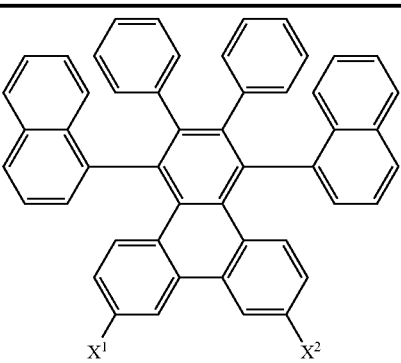 |
| Compound    X¹ = X² | Compound    X¹ = X² |

-continued

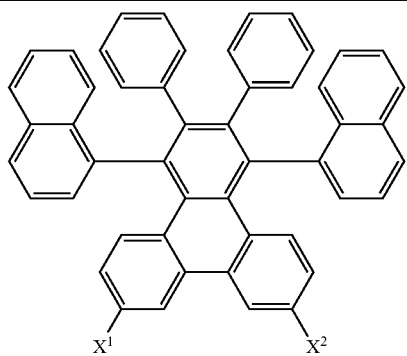

| Compound | X¹ = X² |
|---|---|
| AM-1 is | 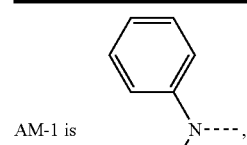 |
| AM-2 is | 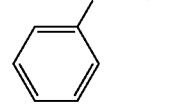 |
| AM-3 is | 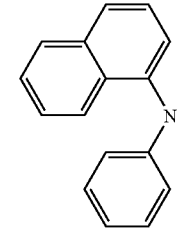 |
| AM-4 is | 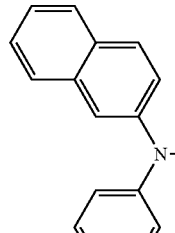 |
| AM-5 is | 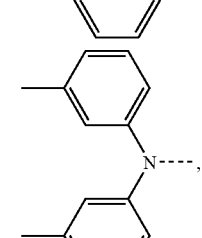 |

-continued

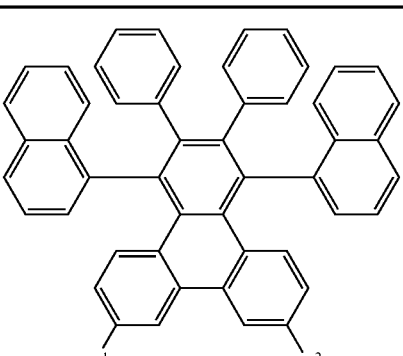

| Compound | X¹ = X² |
|---|---|
| AM-6 is | 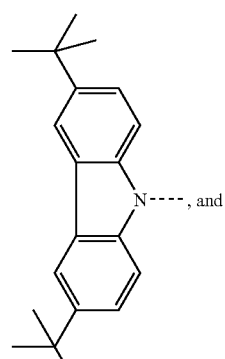, and |
| AM-7 is | 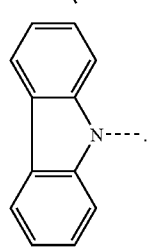 |

4. The electroluminescent device according to claim 1, comprising a cathode, an anode, and therebetween a light emitting layer containing a host material and a phosphorescent light-emitting material, wherein the host material is a compound of formula I.

5. A compound of the formula

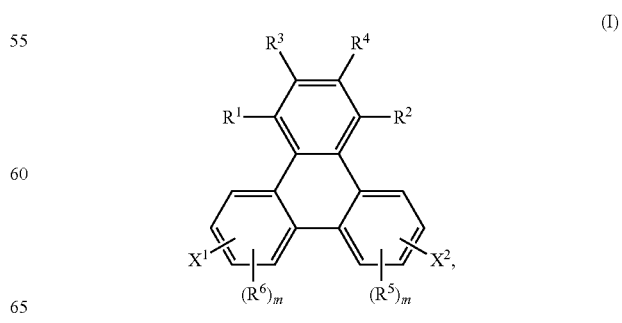

selected from the group consisting of

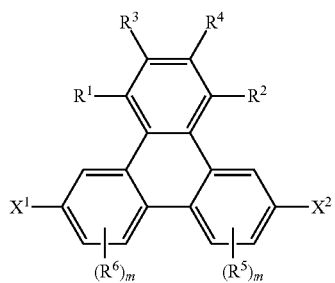
(II)

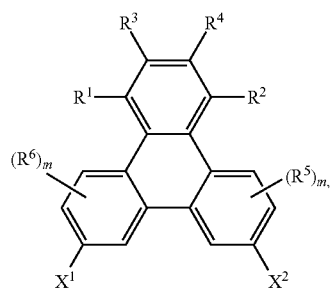
(III)

wherein m can be the same or different at each occurrence and is 0, 1, 2, or 3, $R^1$ and $R^2$ are a group of formula

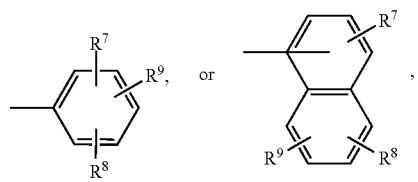

and $R^3$ is hydrogen and $R^4$ is a $C_1$-$C_{25}$alkyl group, or a group of formula

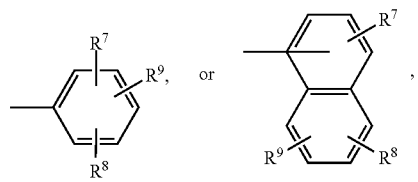

$R^3$ is hydrogen and $R^4$ is a $C_1$-$C_{25}$alkyl group, or a group of formula

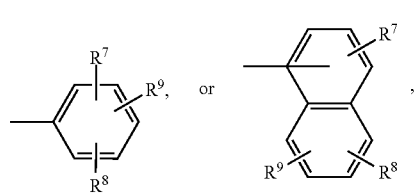

or $R^3$ and $R^4$ are a group of formula

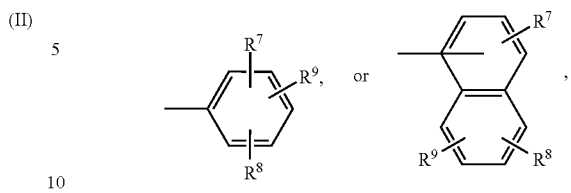

wherein $R^7$, $R^8$ and $R^9$ are independently of each other H, $C_1$-$C_{18}$alkyl, $C_1$-$C_{18}$alkoxy, or $C_1$-$C_{18}$alkyl which is interrupted by O, $R^5$ and $R^6$ are independently of each other halogen, or an organic substituent, or $R^5$ and $R^6$, which are adjacent to each other, together form an aromatic, or heteroaromatic ring, or ring system, which can optionally be substituted, and -$L^1$-$X^1$ and -$L^2$-$X^2$ are independently of each other a group of formula -$NA^1A^{1'}$, or a group

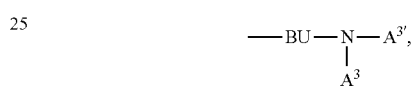

wherein $A^1$, $A^{1'}$, $A^3$ and $A^{3'}$ are independently of each other a $C_6$-$C_{24}$aryl group, or a $C_2$-$C_{30}$heteroaryl group, which can optionally be substituted, selected from the group consisting of phenyl, naphthyl, anthryl, biphenylyl, 2-fluorenyl, phenanthryl, and perylenyl, which can optionally be substituted, said groups being selected from the group consisting of

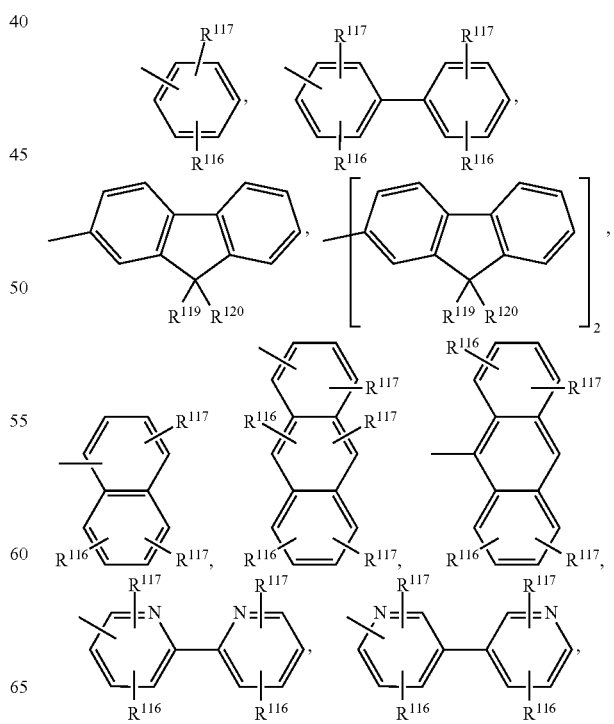

-continued

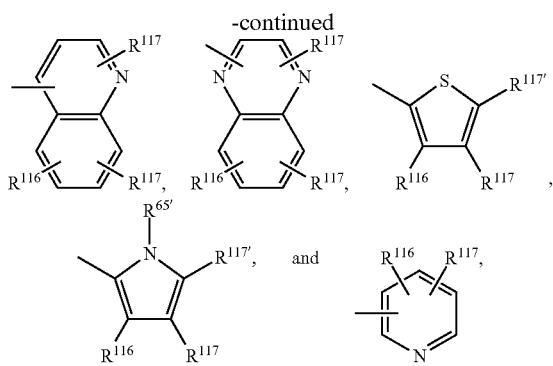

or A$^1$ and A$^{1'}$, or A$^3$ and A$^{3'}$ together with the nitrogen atom to which they are bonded form a heteroaromatic ring, or ring system, selected from the group consisting of

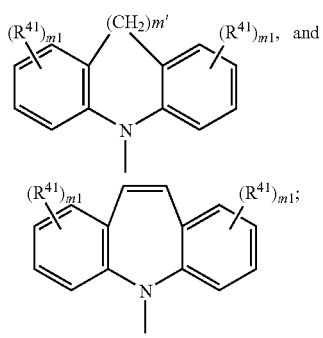

of wherein m' is 0, 1, or 2;
m1 can be the same or different at each occurrence and is 0, 1, 2, 3, or 4;
R$^{116}$, R$^{117}$ and R$^{117'}$ are independently of each other H, halogen, —CN, C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, C$_2$-C$_{20}$ heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, C$_7$-C$_{25}$aralkyl, —C(=O)—R$^{127}$, —C(=O)OR$^{127}$, or —C(=O)NR$^{127}$R$^{126}$, or
substituents R$^{116}$, R$^{117}$ and R$^{117'}$, which are adjacent to each other, can form a ring,
R$^{119}$ and R$^{120}$ are independently of each other C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, C$_2$-C$_{20}$ heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, or C$_7$-C$_{25}$aralkyl, or
R$^{119}$ and R$^{120}$ together form a group of formula =CR$^{121}$R$^{122}$, wherein
R$^{121}$ and R$^{122}$ are independently of each other H, C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, or C$_2$-C$_{20}$ heteroaryl, or C$_2$-C$_{20}$heteroaryl which is substituted by G, or
R$^{119}$ and R$^{120}$ together form a five or six membered ring, which optionally can be substituted by C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, C$_7$-C$_{25}$aralkyl, or —C(=O)—R$^{127}$, R$^{126}$ and R$^{127}$ are independently of each other H; C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—,
BU is

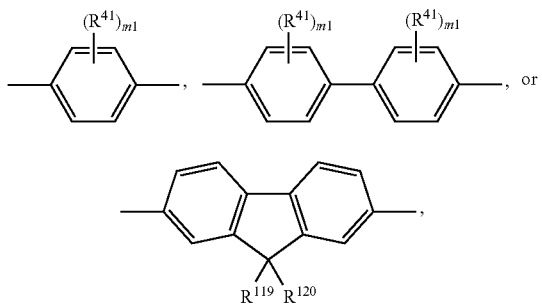

wherein R$^{41}$ can be the same or different at each occurrence and is Cl, F, CN, NR$^{45}$R$^{45'}$, a C$_1$-C$_{25}$alkyl group, a C$_4$-C$_{18}$cycloalkyl group, a C$_1$-C$_{25}$alkoxy group, in which one or more carbon atoms which are not adjacent to each other could be replaced by —NR$^{45}$—, —O—, —S—, or —O—C(=O)—O—, and/or wherein one or more hydrogen atoms can be replaced by F, a C$_6$-C$_{24}$aryl group, or a C$_6$-C$_{24}$aryloxy group, wherein one or more carbon atoms can be replaced by O, S, or N, and/or which can be substituted by one or more non-aromatic groups R$^{41}$, or
two or more groups R$^{41}$ form a ring system;
R$^{45}$ and R$^{45'}$ are independently of each other a C$_1$-C$_{25}$alkyl group, a C$_4$-C$_{18}$cycloalkyl group, in which one or more carbon atoms which are not adjacent to each other could be replaced by —NR$^{45''}$—, —O—, —S—, —C(=O)—O—, or, —O—C(=O)—O—, and/or wherein one or more hydrogen atoms can be replaced by F, a C$_6$-C$_{24}$aryl group, or a C$_6$-C$_{24}$aryloxy group, wherein one or more carbon atoms can be replaced by O, S, or N, and/or which can be substituted by one or more non-aromatic groups R$^{41}$,
R$^{45''}$ is a C$_1$-C$_{25}$alkyl group, or a C$_4$-C$_{18}$cycloalkyl group, and m1 can be the same or different at each occurrence and is 0, 1, 2, 3 or 4; or -L$^1$-X$^1$ and -L$^2$-X$^2$ are independently of each other a group

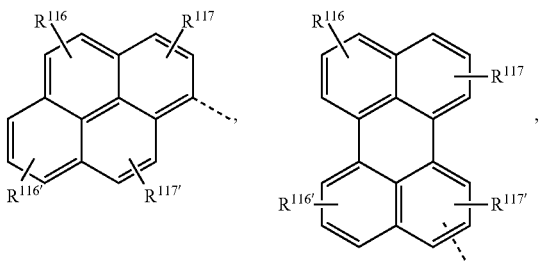

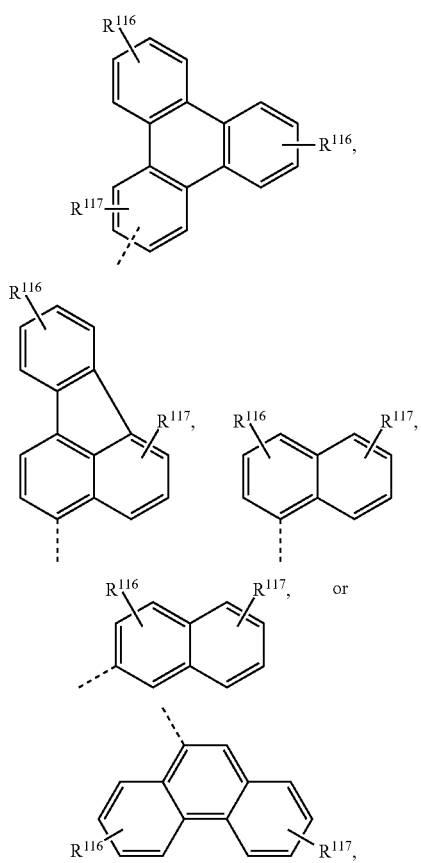
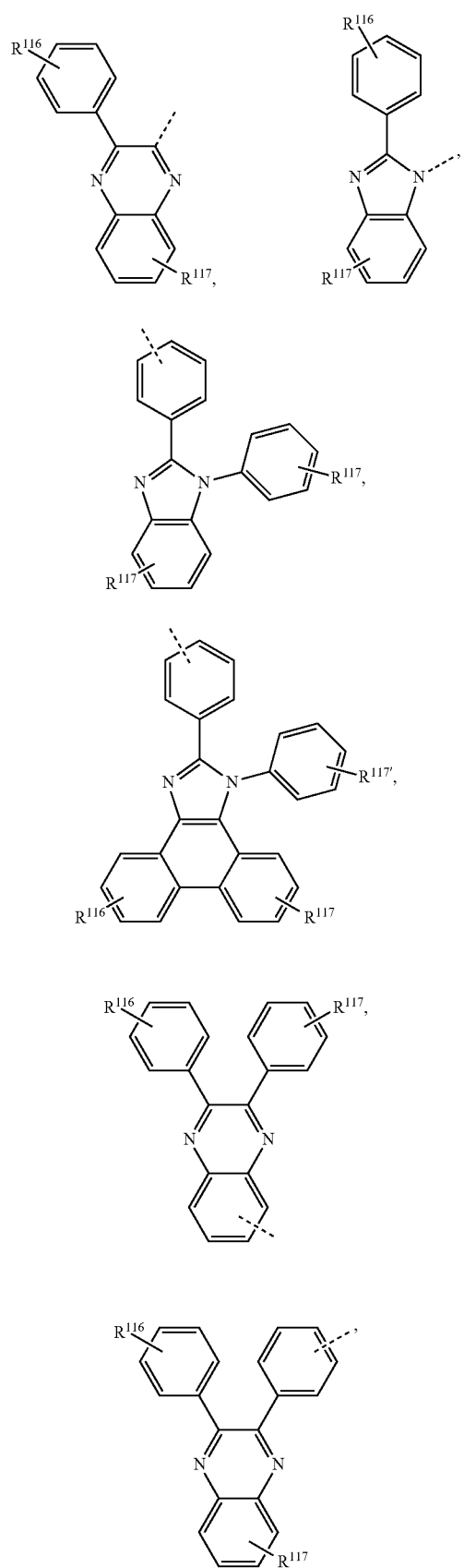
wherein
$R^{116}$, $R^{116'}$, $R^{117}$ and $R^{117'}$ are as defined above,
D is —CO—, —COO—, —S—, —SO—, —SO$_2$—, —O—, —NR$^{65}$—, —SiR$^{70}$R$^{71}$, —POR$^{72}$—, —CR$^{63}$=CR$^{64}$—, or —C≡C—, and
E is —OR$^{69}$, —SR$^{69}$, —NR$^{65}$R$^{66}$, —COR$^{68}$, —COOR$^{67}$, —CONR$^{65}$R$^{66}$, —CN, or halogen,
G is E, or C$_1$-C$_{18}$alkyl; or -L$^1$-X$^1$ and -L$^2$-X$^2$ are independently of each other a group -continued

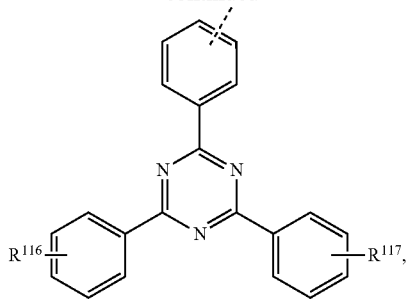

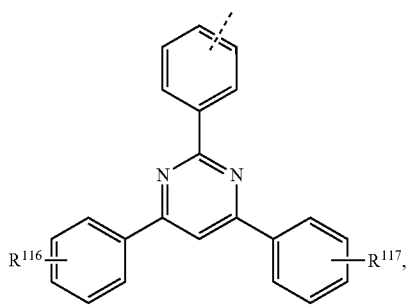

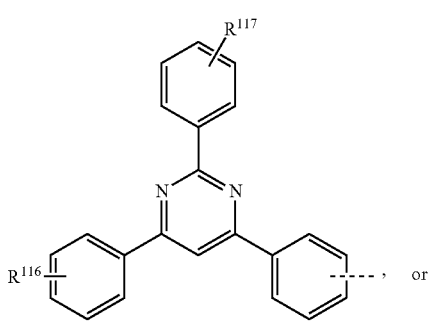

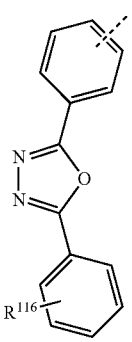

wherein $R^{116}$, $R^{117}$ and $R^{117'}$ are as defined above.

6. A process for the preparation of compounds of the formula I according to claim 5, wherein $X^1$ and $X^2$ are independently of each other —$NA^1A^{1'}$,

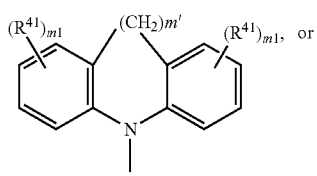

-continued

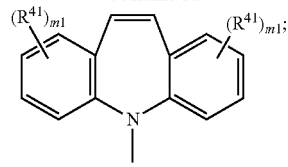

m' is 0, 1, or 2; which comprises reacting a compound of formula (XX)

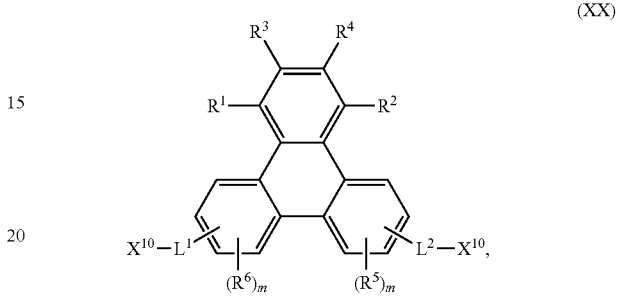

wherein $X^{10}$ stands for a halogen, selected from the group consisting of bromo, and iodo,
with a compound of formula $HNA^1A^{1'}$,

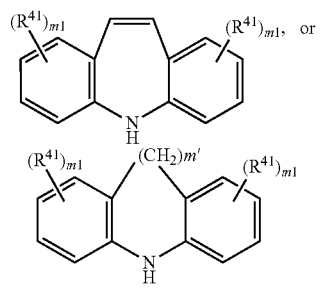

in the presence of a base and a catalyst in a solvent,
wherein $A^1$ and $A^{1'}$ are independently of each other a $C_6$-$C_{24}$ aryl group, a $C_2$-$C_{30}$ heteroaryl group, which can optionally be substituted, or $A^1$ and $A^{1'}$ together with the nitrogen atom to which they are bonded from a heteroaromatic ring, or ring system selected from the group consisting of

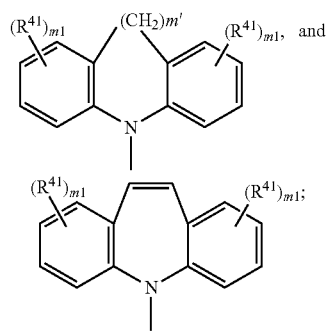

wherein m' is 0, 1, or 2;
m1 can be the same or different at each occurrence and is 0, 1, 2, 3, or 4,
$R^{41}$ can be the same or different at each occurrence and is Cl, F, CN, $NR^{45}R^{45'}$, a $C_1$-$C_{23}$ alkyl group, a $C_4$-$C_{18}$ cycloalkyl group, a $C_1$-$C_{25}$ alkoxy group, in which one or more carbon atoms which are not in neighborhood to each other could be replaced by —$NR^{45}$—, —O—, —S—, —C(=O)—O—, or —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, or two or more groups $R^{41}$ form a ring system;

$R^{45}$ and $R^{45'}$ are independently of each other a $C_1$-$C_{25}$alkyl group, a $C_4$-$C_{18}$cycloalkyl group, in which one or more carbon atoms which are not in neighborhood to each other could be replaced by —$NR^{45''}$—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N and/or which can be substituted by one or more non-aromatic groups $R^{41}$, and $R^{45''}$ is a $C_1$-$C_{25}$ alkyl group, or a $C_4$-$C_{18}$ cycloalkyl group.

\* \* \* \* \*